United States Patent [19]

Novacek et al.

[11] Patent Number: 5,462,531

[45] Date of Patent: Oct. 31, 1995

[54] SAFETY SYRINGE NEEDLE DEVICE WITH INTERCHANGEABLE AND RETRACTABLE NEEDLE PLATFORM

[75] Inventors: Laurel A. Novacek; Fraser R. Sharp; Donald A. McLean, all of Vancouver, Canada

[73] Assignee: Inviro Medical Devices Ltd., Barbados, Br. Indian Ocean Ter.

[21] Appl. No.: 361,227

[22] Filed: Dec. 21, 1994

Related U.S. Application Data

[63] Continuation-in-part of Ser. No. 128,694, Sep. 30, 1993, Pat. No. 5,415,638, which is a continuation-in-part of Ser. No. 909,385, Jul. 9, 1992, Pat. No. 5,263,933, which is a continuation-in-part of Ser. No. 800,849, Nov. 29, 1991, Pat. No. 5,205,827, which is a division of Ser. No. 687,108, Apr. 18, 1991, Pat. No. 5,112,318, which is a continuation-in-part of Ser. No. 607,127, Oct. 3, 1990, Pat. No. 5,122,124, which is a continuation-in-part of Ser. No. 410,318, Sep. 21, 1989, Pat. No. 5,030,208, which is a continuation-in-part of Ser. No. 327,344, Mar. 22, 1989, abandoned, which is a continuation-in-part of Ser. No. 285,012, Dec. 14, 1988, abandoned.

[51] Int. Cl.⁶ ............................................. A61M 5/00
[52] U.S. Cl. ............................................. 604/110; 604/195
[58] Field of Search ............................. 604/110, 187, 604/195, 198, 263, 218, 220

[56] References Cited

U.S. PATENT DOCUMENTS

| | | |
|---|---|---|
| 2,688,325 | 9/1954 | Lockhart . |
| 2,722,215 | 11/1955 | Dahlgren . |
| 2,880,725 | 4/1959 | Kendall . |
| 2,888,923 | 6/1959 | Cunha Reis . |
| 3,306,290 | 2/1967 | Weltman . |
| 3,354,882 | 11/1967 | Coanda . |
| 3,356,089 | 12/1967 | Francis . |
| 3,487,834 | 1/1970 | Smith, Jr. et al. . |
| 3,527,216 | 9/1970 | Snyder . |
| 3,884,230 | 5/1975 | Wulff . |
| 3,930,492 | 1/1976 | Hatsuno et al. . |
| 4,026,287 | 5/1977 | Haller . |
| 4,085,737 | 4/1978 | Bordow . |

(List continued on next page.)

FOREIGN PATENT DOCUMENTS

| | | |
|---|---|---|
| 157409 | 5/1991 | China . |
| 191355 | 9/1992 | China . |
| 225161 | 6/1994 | China . |
| 0278493 | 8/1988 | European Pat. Off. . |
| 0327061 | 8/1989 | European Pat. Off. . |
| 0347742 | 12/1989 | European Pat. Off. . |
| 1150980 | 5/1969 | United Kingdom . |
| WO89/08468 | 9/1989 | WIPO . |
| WO89/12475 | 12/1989 | WIPO . |
| WO90/11099 | 10/1990 | WIPO . |

*Primary Examiner*—John D. Yasko
*Attorney, Agent, or Firm*—Nixon & Vanderhye

[57] ABSTRACT

The syringe includes a barrel, a plunger, and an adapter for mounting the needle in the distal end of the barrel. The adapter includes a protrusion projecting away from the needle end and into the barrel defining an annular space between the barrel and the protrusion. The plunger and protrusion have complementary surfaces whereby the plunger may grip the adapter for removal of the adapter into the interior of the barrel after use. These complementary surfaces afford initial resistance to further axial movement of the plunger toward the adapter, signalling the user that further axial pressure will permanently lock the plunger and adapter to one another whereby, upon application of full axial pressure on the plunger, the complementary surfaces of the plunger and adapter permanently lock to one another to enable joint unitary movement of the plunger and adapter together with the needle carried by the adapter into the barrel. The adapter includes vent passages communicating between the central passage through the adapter and the annular space whereby air can be vented from the barrel after receiving fluid within the barrel and prior to injection. Thus, the syringe may be oriented in a vertical position needle end uppermost with the vent passages forming the most superior portion of the barrel interior whereby air may be vented.

33 Claims, 29 Drawing Sheets

U.S. PATENT DOCUMENTS

| | | |
|---|---|---|
| 4,139,009 | 2/1979 | Alvarez . |
| 4,258,713 | 3/1981 | Wardlaw . |
| 4,266,543 | 5/1981 | Blum . |
| 4,266,544 | 5/1981 | Wardlaw . |
| 4,425,120 | 1/1984 | Sampson et al. . |
| 4,459,997 | 7/1984 | Sarstedt . |
| 4,507,117 | 3/1985 | Vining et al. . |
| 4,542,749 | 9/1985 | Caselgrandi et al. . |
| 4,562,844 | 1/1986 | Carpenter et al. . |
| 4,573,976 | 3/1986 | Sampson et al. . |
| 4,592,744 | 6/1986 | Jagger et al. . |
| 4,631,057 | 12/1986 | Mitchell . |
| 4,650,468 | 3/1987 | Jennings, Jr. . |
| 4,655,751 | 4/1987 | Harbaugh . |
| 4,675,005 | 6/1987 | DeLuccia . |
| 4,692,156 | 9/1987 | Haller . |
| 4,695,274 | 9/1987 | Fox . |
| 4,710,170 | 12/1987 | Haber et al. . |
| 4,747,830 | 5/1988 | Gloyer et al. . |
| 4,770,655 | 9/1988 | Haber et al. . |
| 4,774,964 | 10/1988 | Bonaldo . |
| 4,790,822 | 12/1988 | Haining . |
| 4,790,828 | 12/1988 | Dombrowski et al. . |
| 4,795,443 | 1/1989 | Permenter et al. . |
| 4,804,370 | 2/1989 | Haber et al. . |
| 4,810,248 | 3/1989 | Masters et al. . |
| 4,813,426 | 3/1989 | Haber et al. . |
| 4,813,936 | 3/1989 | Schroeder . |
| 4,832,695 | 5/1989 | Rosenberg et al. . |
| 4,838,870 | 6/1989 | Haber et al. . |
| 4,861,338 | 8/1989 | Mathiesen et al. . |
| 4,874,383 | 10/1989 | McNaughton . |
| 4,883,471 | 11/1989 | Braginetz et al. . |
| 4,929,232 | 5/1990 | Sweeney et al. . |
| 4,946,441 | 8/1990 | Laderoute . |
| 4,950,241 | 8/1990 | Ranford . |
| 4,955,870 | 9/1990 | Ridderheim et al. . |
| 4,978,340 | 12/1990 | Terrill et al. . |
| 4,986,813 | 1/1991 | Blake, III et al. . |
| 4,997,423 | 3/1991 | Okuda et al. . |
| 5,030,208 | 7/1991 | Novacek et al. . |
| 5,112,318 | 5/1992 | Novacek et al. . |
| 5,122,124 | 6/1992 | Novacek et al. . |
| 5,152,750 | 10/1992 | Haining . |
| 5,205,827 | 4/1993 | Novacek et al. . |
| 5,242,400 | 9/1993 | Blake, III et al. . |
| 5,256,151 | 10/1993 | Chul . |
| 5,263,933 | 11/1993 | Novacek et al. . |
| 5,308,329 | 5/1994 | Mazur et al. ............ 604/110 |
| 5,328,475 | 7/1994 | Chen . |
| 5,342,323 | 8/1994 | Haining ................... 604/195 |
| 5,360,404 | 11/1994 | Novacek et al. . |
| 5,393,301 | 2/1995 | Goldberg ............ 604/263 X |
| 5,395,337 | 3/1995 | Clemens et al. ......... 604/110 |
| 5,401,246 | 3/1995 | Mazur et al. ............ 604/110 |

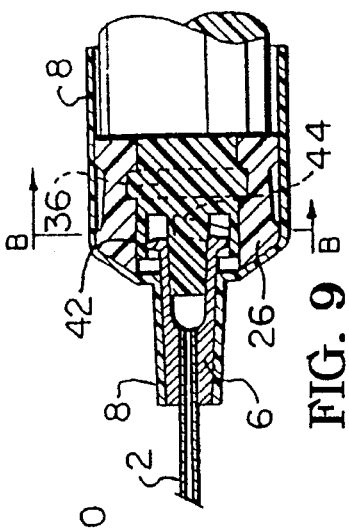
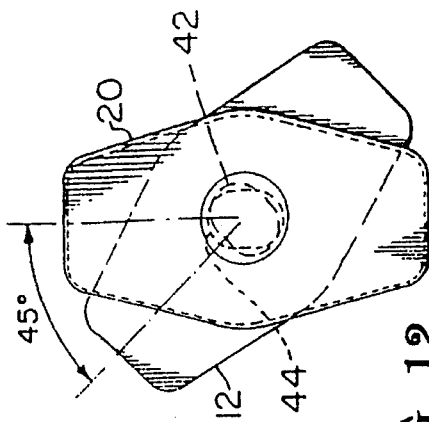
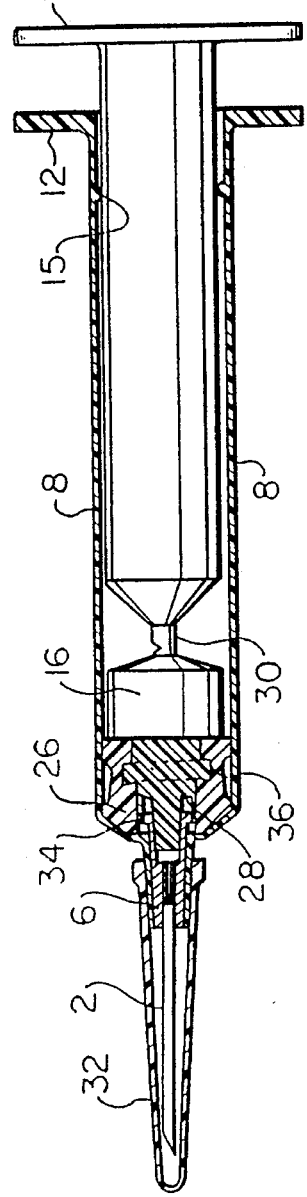
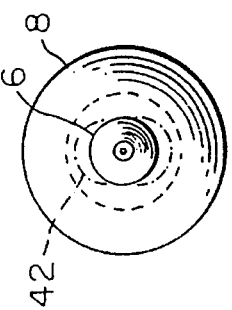
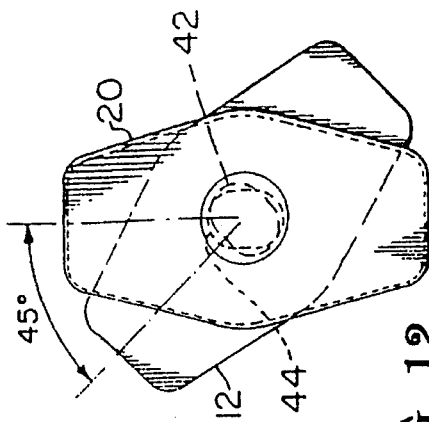

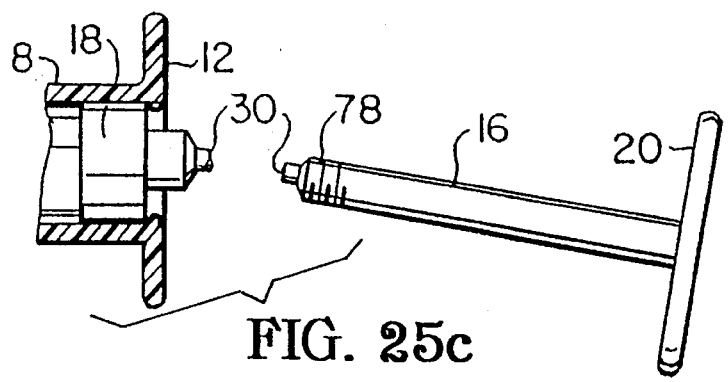
FIG. 25c
FIG. 25d
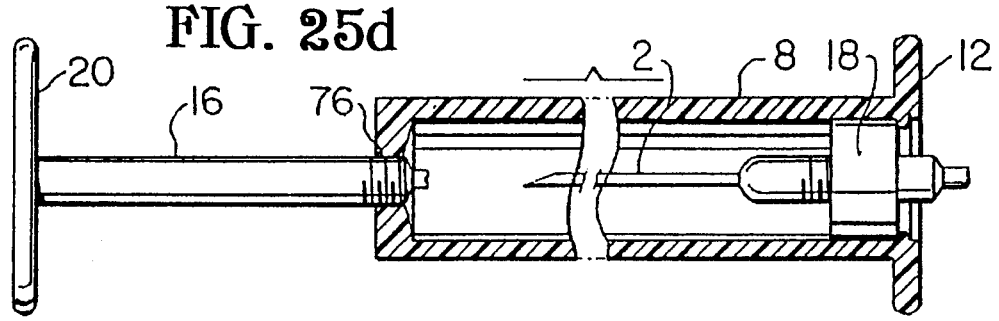
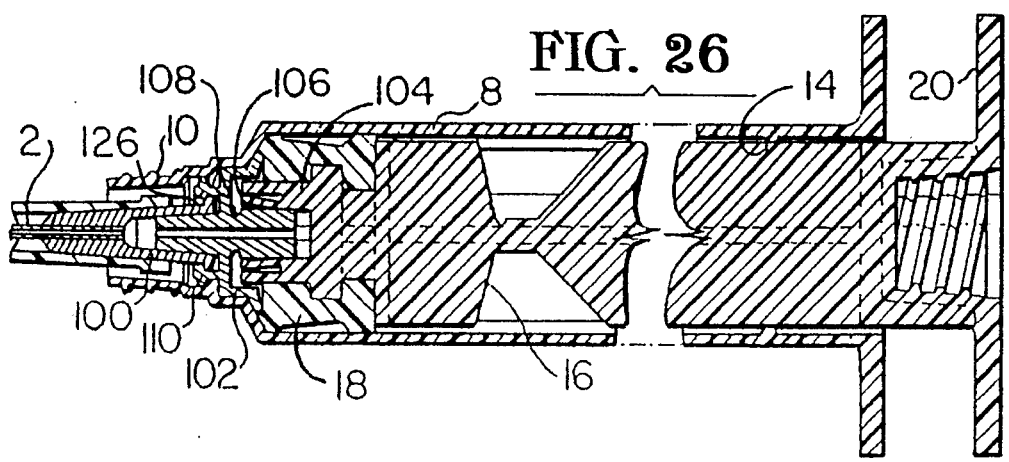
FIG. 26
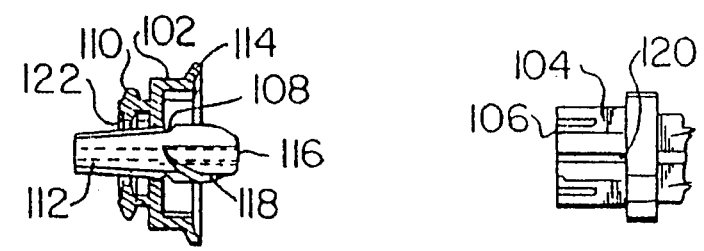
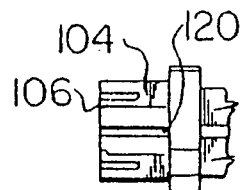
FIG. 27        FIG. 28

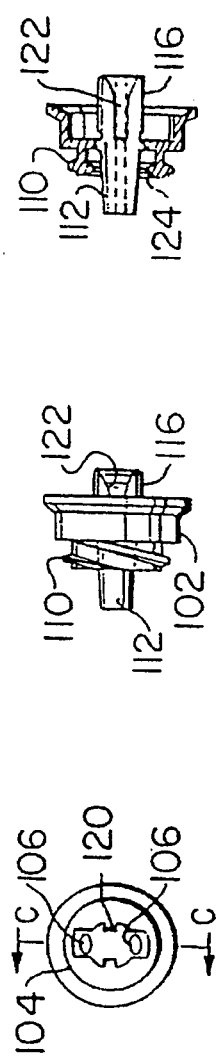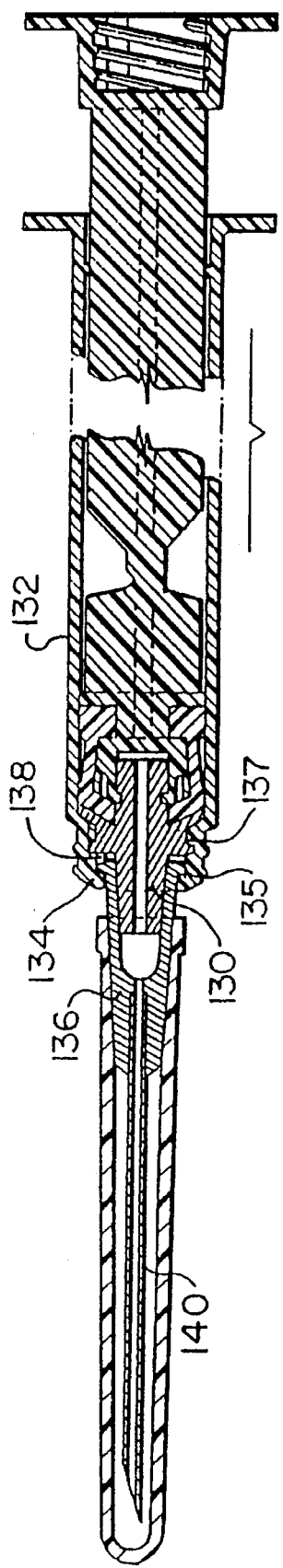
FIG. 29　FIG. 30　FIG. 31　FIG. 32

FIG. 35
FIG. 37
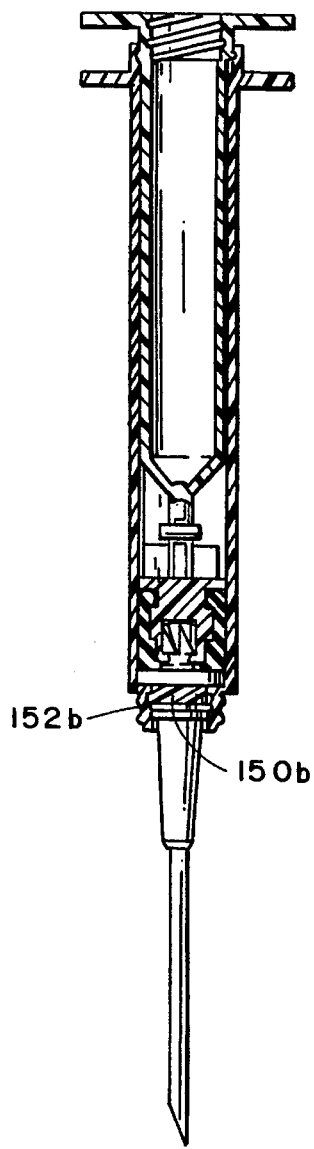
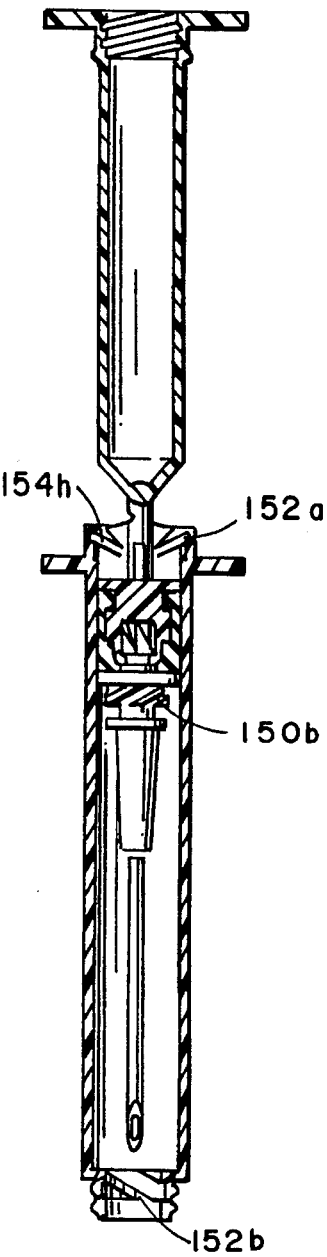
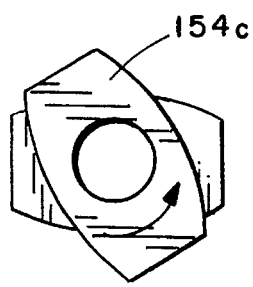
FIG. 36

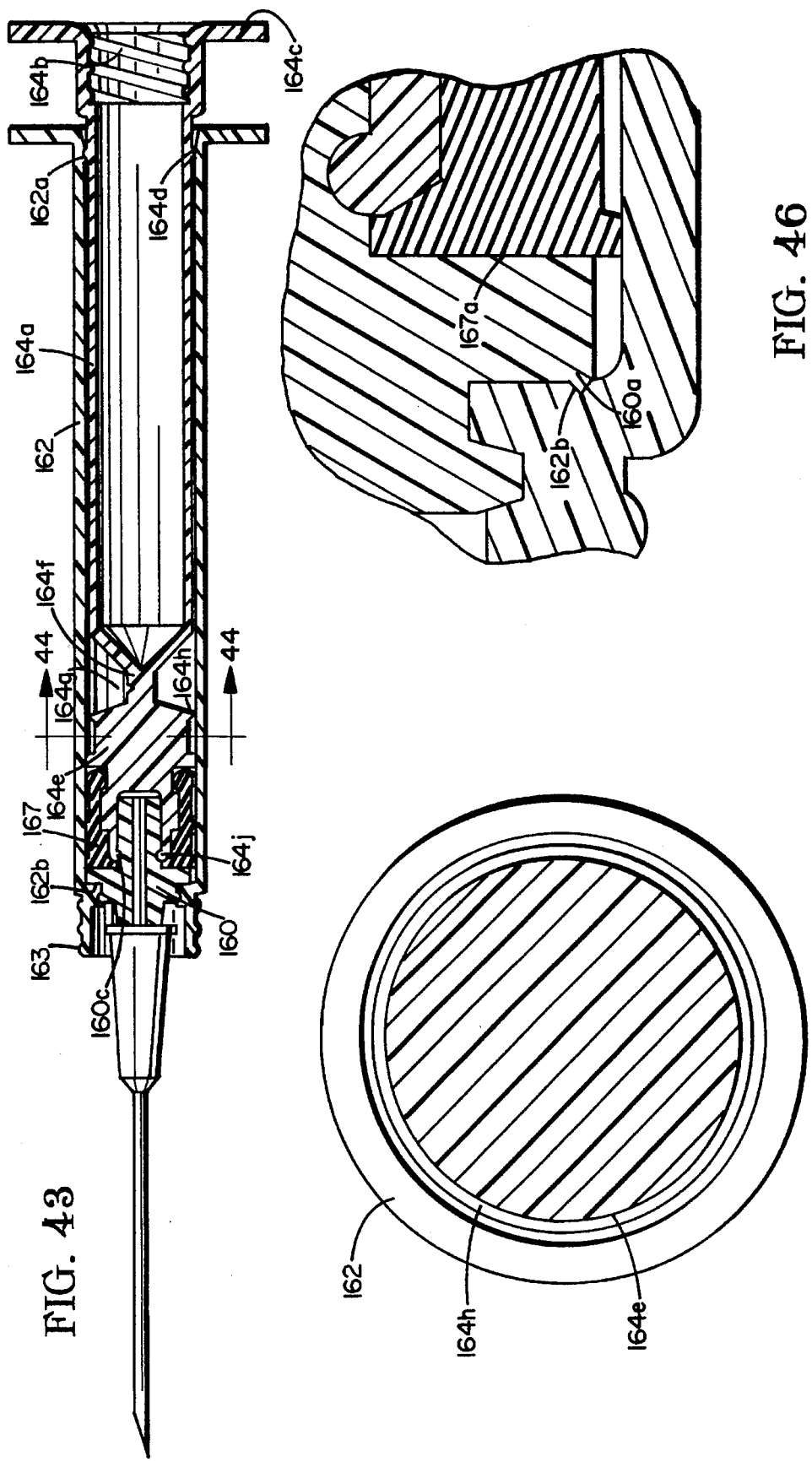

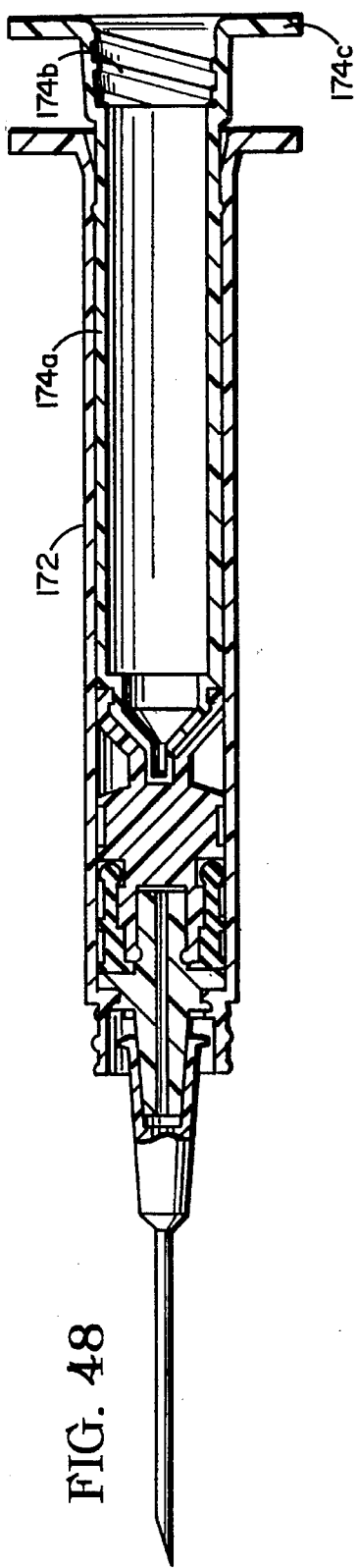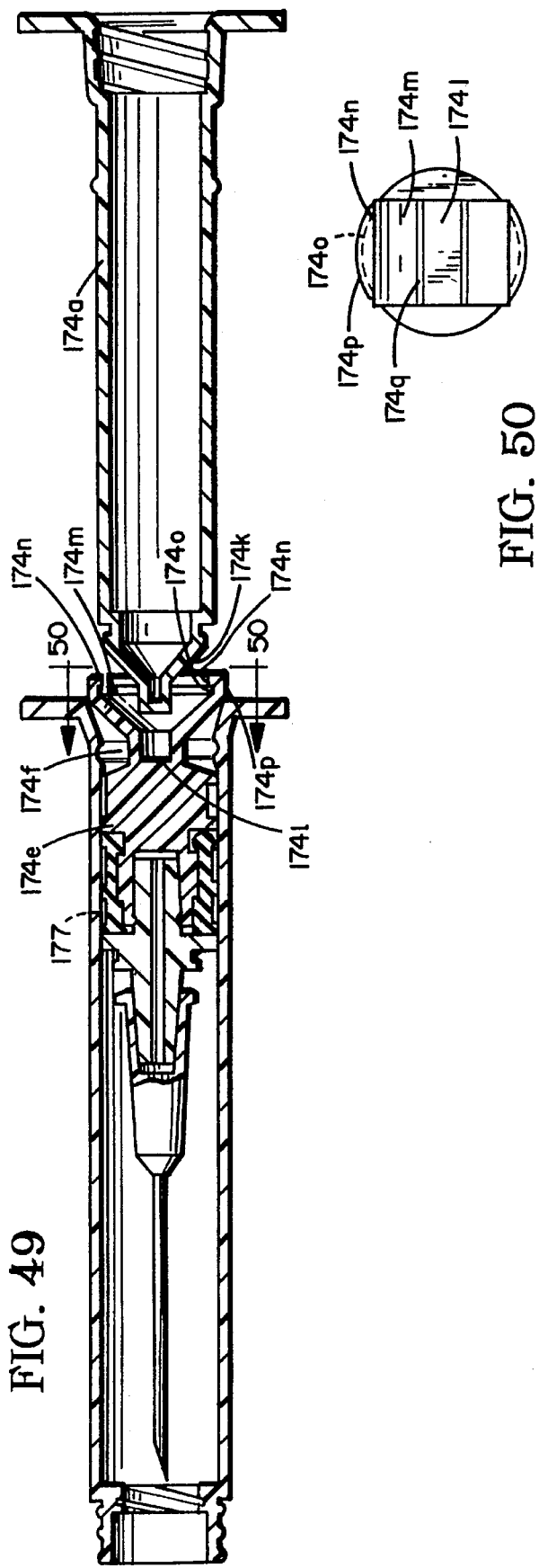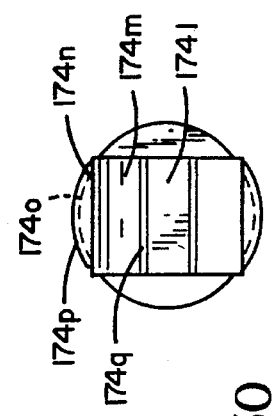
FIG. 48
FIG. 49
FIG. 50

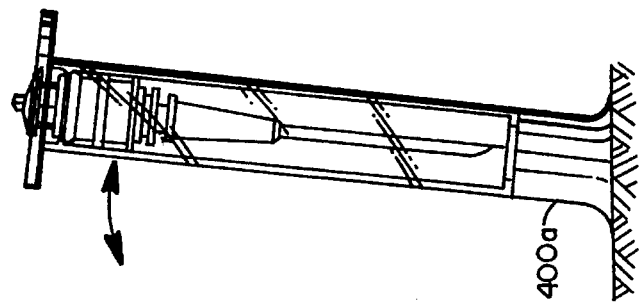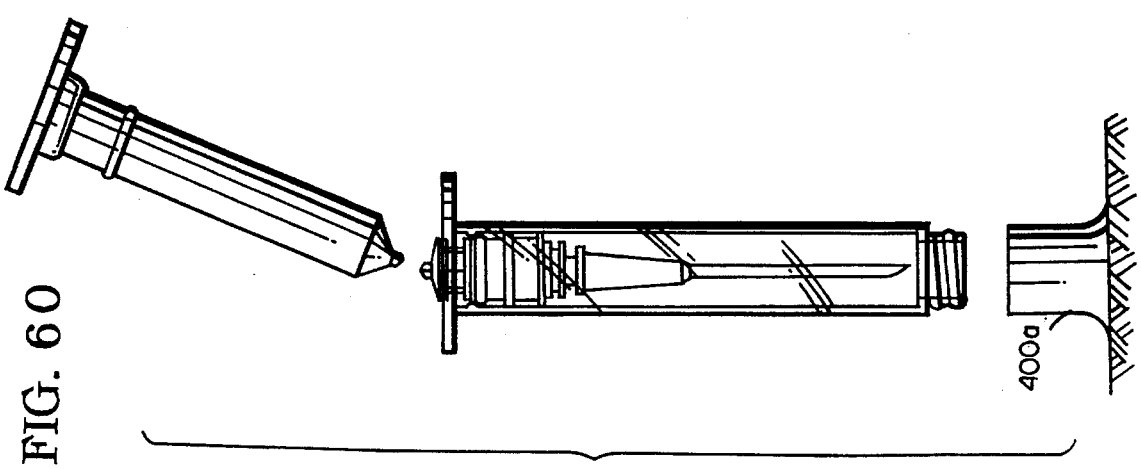
FIG. 62
FIG. 61
FIG. 60

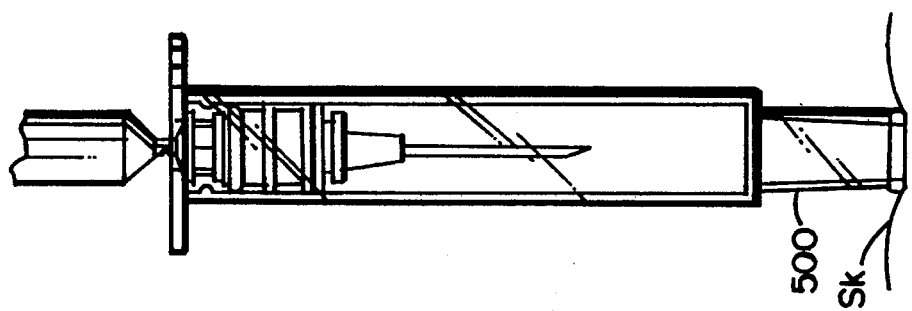
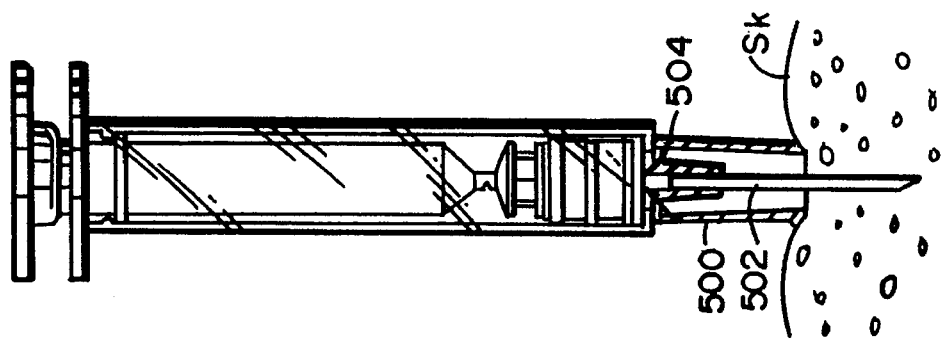

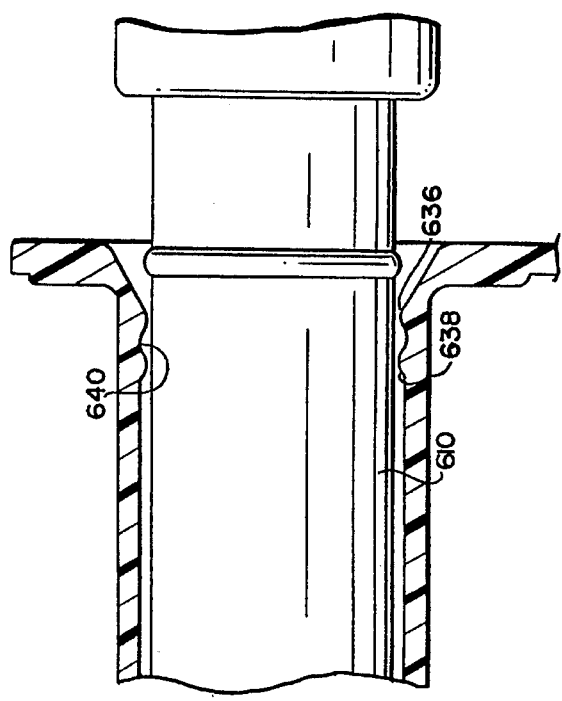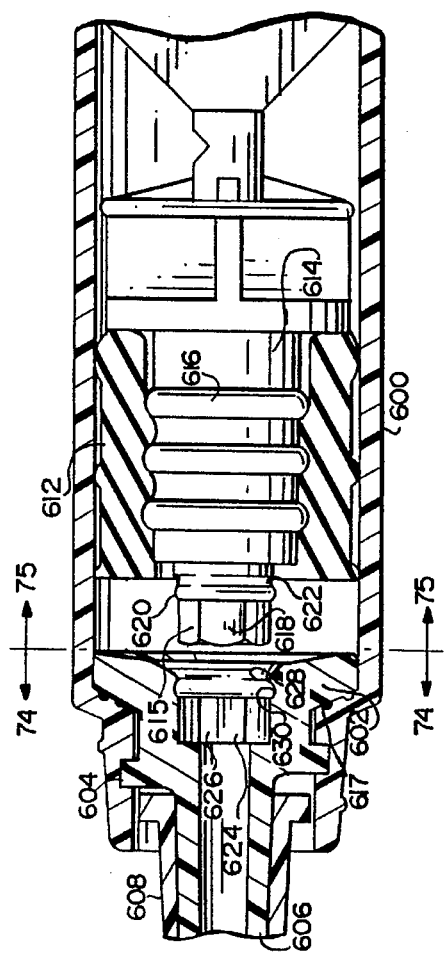
FIG. 65
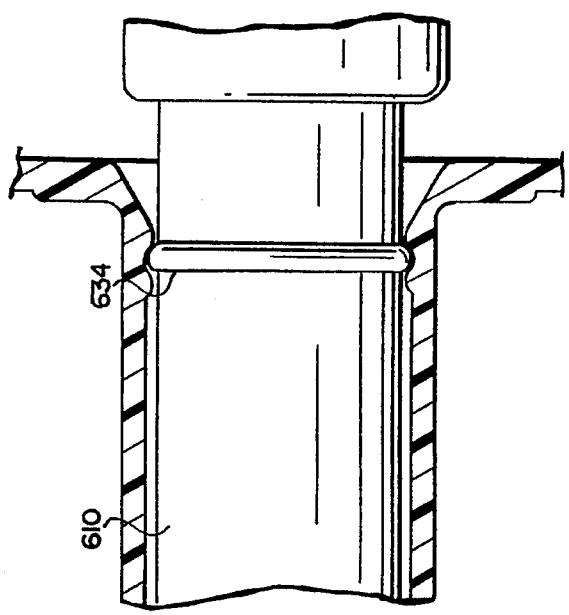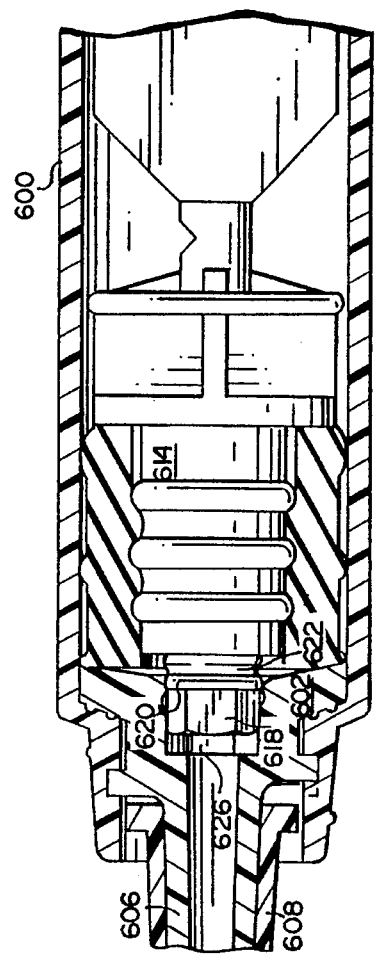
FIG. 66

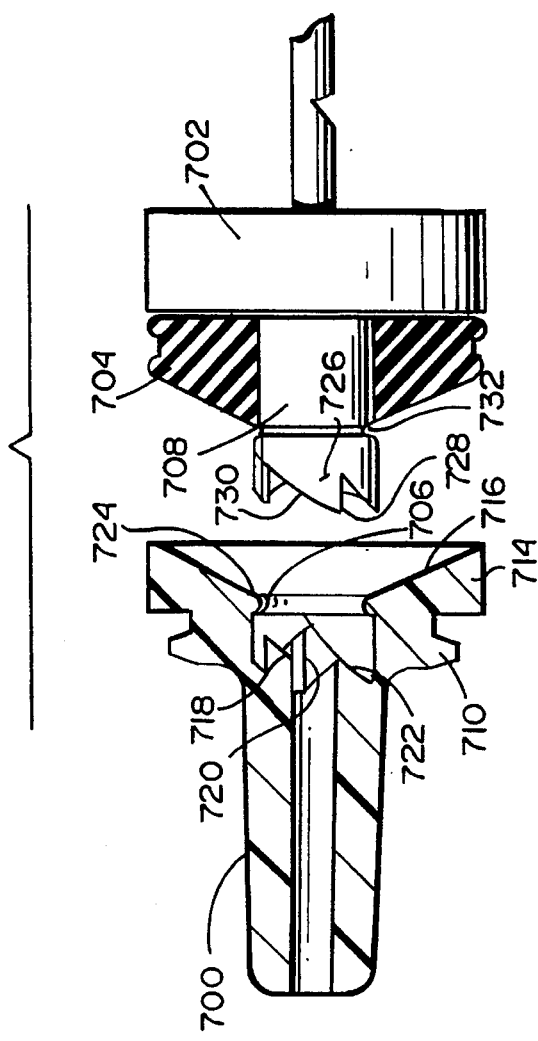

SAFETY SYRINGE NEEDLE DEVICE WITH INTERCHANGEABLE AND RETRACTABLE NEEDLE PLATFORM

RELATED APPLICATIONS

This application is a continuation-in-part application of application Ser. No. 08/128,694, filed Sep. 30, 1993 now U.S. Pat. No. 5,415,638, which in turn is a continuation-in-part application of application Ser. No. 07/909,385, filed Jul. 9, 1992, now U.S. Pat. No. 5,263,933, which, in turn, is a continuation-in-part of application Ser. No. 07/800,849, filed Nov. 29, 1991, now U.S. Pat. No. 5,205,827, issued Apr. 27, 1993, which is a divisional of application Ser. No. 07/687,108, filed Apr. 18, 1991, now U.S. Pat. No. 5,112,318, issued May 12, 1992, which is a continuation-in-part of application Ser. No. 607,127, filed Oct. 3, 1990, now U.S. Pat. No. 5,122,124, issued Jun. 16, 1992, which is a continuation-in-part of application Ser. No. 07/410,318, filed Sep. 21, 1989, now U.S. Pat. No. 5,030,208, issued Jun. 9, 1991, which was a continuation-in-part of application Ser. No. 07/327,344, filed Mar. 22, 1989, now abandoned, which was a continuation-in-part of application Ser. No. 07/285,012, filed Dec. 14, 1988, now abandoned, the disclosures of which are incorporated herein by reference.

FIELD OF THE INVENTION

This invention relates to a novel safety disposal syringe needle device which has medical and industrial application. More particularly, this invention pertains to a syringe which, after being used by a person to inject medication or fluid into a patient, or withdraw fluids from a patient after sampling or exposure to toxic materials, or the like, can be transformed by the person to withdraw the needle into the barrel of the syringe for disposal purposes, thereby eliminating needle stick injuries among such persons.

BACKGROUND OF THE INVENTION

Needle stick injuries among medical personnel such as health care workers are of growing concern because of disease transmission, particularly the deadly virus known as HIV-1 (AIDS) and Hepatitis B. The AIDS virus for which there is no known cure is estimated to infect more than twenty million people worldwide and is spreading rapidly. Although in 1985 medical publications stated that no health care workers had become infected with the AIDS virus, it is now known that there is a significant risk to health care workers. A report in the New England Journal of Medicine, Aug. 14, 1988, indicates that the risk of acquiring HIV-1 infection is 0.35–0.74% per needle stick injury. The reported incidence of needle stick injuries to medical staff has been reported at 25.3 per 100 beds annually. In one New York hospital, at least 7% of house doctors have sustained needle stick injuries while caring for AIDS patients.

Transmission rates of Hepatitis B after needle stick exposure are much higher than that occurring with the HIV virus and may be 6–30%. The Center for Disease Control has estimated 200–300 health care workers die annually in the U.S.A. from occupationally acquired Hepatitis B.

With presently used syringes with projecting needles, potentially dangerous needle stick injuries are commonplace and most often occur between the time the medication is injected into the patient and the time the syringe is disposed of. Most injuries occur while recapping the needle or when disposing of it into a disposal container. However, maintenance personnel who handle disposed materials are also subject to needle stick injuries.

At present, there is no reason to believe that the AIDS epidemic will come to a quick end. Canada's frequency rate at the present time is 100.2 cases per 1,000,000. The United States is a frightening 377.1 cases per 1,000,000. In Canada, according to current data projections, the incidence of AIDS rate at least doubles every eighteen months.

A number of patents disclose syringes or the like having needle protecting features. In spite of this there are no syringes which allow withdrawal and safe entrapment of needles currently on the market. This suggests difficulties with manufacture of prior patent designs. The syringe which is the subject of this patent application is manufacturable and commercially viable. In addition, after proper medical use the syringe cannot be reused and any toxic substances or infections contained within the barrel are not accessible without physical breakage of the syringe. U.S. Pat. No. 4,592,744, Jagger et al., Jun. 3, 1986, illustrates a disposable medical needle apparatus with a self-sheathing safety needle assembly. The self-sheathing safety needle has a case with a small closed end and a large open end. A needle assembly is located within the case with the needle projecting through the small closed end. A hub is connected to the needle assembly inside the case. The connector on the hub cooperates with a receiver on the small end to hold the needle assembly in the case. A flange on the hub cooperates with an inward projection in the case based from the small end to prevent movement of the needle out of the case when the needle is withdrawn from the opening in the small end. The nozzle of a syringe pushed into the hub withdraws the needle when the syringe is withdrawn. A rubber stopper on a vacuum tube withdraws the needle after the rubber stopper turns the flange to release the connector from the receiver.

U.S. Pat. No. 4,804,370, granted Feb. 14, 1989, Haber et al., discloses a disposable disease control syringe which reduces the frequency of accidental needle strikes to health care workers and prevents health-threatening reuse of the needle cannula by drug abusers. The syringe includes a cylinder having an open proximal end, a substantially closed distal end, and a retractable needle projecting through the distal end. A piston assembly having a detachable stem and a needle capturing receptacle moves axially and distally through the syringe cylinder to expulse fluid medication and to selectively engage the needle at the most distal aspect of the cylinder. The piston assembly is then withdrawn proximally through the cylinder, whereby to relocate the needle from the distal end to the proximal cylinder end. The needle capturing receptacle is locked at the proximal end of the syringe cylinder with the needle cannula retracted within and completely shielded by the cylinder. The stem is then detached from the piston assembly and discarded, thereby creating a disposal cartridge with the needle cannula rendered permanently irretrievable therewithin. Alternatively, the piston assembly can be driven distally through the cylinder for correspondingly moving the needle into contact with a puncture resistant shield located at the distal end of the cylinder, whereby the needle is axially collapsed and destroyed within the cylinder.

U.S. Pat. Nos. 4,542,749, Caselgrandi et al., and 3,306,290, Weltman, disclose syringes with protected needle designs.

U.S. Patent No. 4,631,057, Mitchell, discloses a syringe which has on the body of the syringe a needle guard which can be moved from a position which shields the needle, to a retracted position which exposes the needle. U.S. Pat. No. 4,425,120, Sampson, granted Jan. 10, 1984, also discloses a shielded hypodermic syringe with a needle guard mounted on the barrel which may be extended or retracted to protect or expose the needle. U.S. Pat. No. 4,573,976, Sampson et al., also discloses a shielded needle syringe comprising a needle guard which can be retracted or extended relative to the body of the syringe, means being provided for releasably retaining the guard in the retracted position. U.S. Pat. No. 3,884,230, Wulff, granted May 20, 1975, discloses a flexible needle guard and device for a hypodermic syringe. This design appears to be directed mainly to avoiding breakage of the needle when the syringe is being used.

U.S. Pat. No. 4,258,713, Wardlaw, discloses an automatic disposable hypodermic syringe which has means for driving the hypodermic needle from a retracted position within the housing of the syringe to an injecting position whereby a portion of the needle protrudes from the housing. This device does not disclose a feature whereby the needle can be protected or retracted after use. U.S. Pat. No. 4,085,737 discloses a blood sampling syringe which includes an apparatus for protecting the open end of the needle of the syringe. The device is intended for minimizing risk of contamination of the needle tip after a blood sample has been taken. U.S. Pat. No. 4,266,543, Blum, granted May 12, 1981, discloses a hypodermic needle protection means which is designed so that the needle can be slidably moved to the interior of the needle support means upon application of pressure.

U.S. Pat. No. 4,266,544, Wardlaw, granted May 12, 1981, discloses an improved disposable syringe wherein retracting means movably mounted on the housing of the syringe is adapted to pull the needle from its projecting position to a safe position whereby the needle is covered by a portion of the syringe. U.S. Pat. No. 4,139,009, Alvarez, discloses a hypodermic needle assembly with a retractable needle cover, the needle cover comprising a plurality of elastically resilient arms extending between a hub portion and a slide member, the arms acting as a restoring force for urging the slide member back over the needle forward portion when the syringe is withdrawn from contact with the skin of a patient.

U.S. Pat. No. 4,774,964 discloses a device which is designed to withdraw blood from a patient. It is not a syringe per se. It is not used for injecting fluids into a patient. However, the device has the capacity to withdraw the needle into the barrel housing.

SUMMARY OF THE INVENTION

This invention relates to a safety disposable syringe. More particularly, this invention pertains to a syringe which after being used by a health care person to inject medication or fluid into a patient or withdraw fluids from a patient, can be transformed by that person to withdraw the needle into the barrel of the syringe for disposal purposes, thereby eliminating the occurrence of needle sticking injuries among such health care persons. This syringe can also be used in industrial processes for sampling or adding substances which may be toxic. After such function, the needle is withdrawn into the barrel to prevent contamination at any further point in the process or during disposal. The syringe and retractable needle feature is adapted to be used with a variety of interchangeable needles of different diameter and length utilizing a universal Luer or Luer lock coupling mechanism.

The invention pertains to a syringe comprising: (a) a hollow elongated barrel means; (b) penetration means which is adapted to removably engage with an end of the barrel means; (c) plunger means adapted to fit within and move axially in the hollow barrel means; the plunger means causing a pumping action within the interior of the barrel means between the plunger means and the end of the barrel means when the plunger means is pushed into the interior of the barrel means in the direction of the end of the barrel means; and (d) engaging means at the end of the plunger means proximate to the penetration means, the engaging means being adapted to engage the penetration means when the plunger means is fully inserted into the interior the barrel means in the direction of the end of the barrel means and cause the penetrating means to part from the barrel means and to be withdrawn into the interior of the barrel when the plunger means is withdrawn away from the end of the barrel meads.

In the syringe, the penetrating means can be a hollow needle which is pointed at one end thereof, and at the end opposite to the pointed end is formed to mate with the penetration means engaging end of the barrel means. An abutting means can be positioned within the interior of the barrel means and permits the plunger to be inserted into the interior of the barrel means through one end but deters the plunger means from being withdrawn from the interior of the barrel means. Alternatively, the barrel means may have two abutting means in the interior of the barrel means, the two abutting means being adapted to trap the plunger means between them when the plunger means is partially withdrawn from the barrel means.

In the syringe as defined, the engaging means may be a hook. The needle engaging means may be a female and male thread combination which is engaged by rotating the plunger relative to the barrel and penetrating means. Alternatively, the engaging means may be a cam-lock combination, the cam on the base of the needle penetrating means engaging with a receiving groove formed in the needle proximate end of the plunger, the cam-lock means engaging by rotating the plunger relative to the barrel.

In another version of the syringe, the end of the plunger proximate the penetrating means can be formed with a snap-over attachment, and the end of the penetrating means proximate the plunger can be formed with a projection which is adapted to receive and be secured by the snap-over attachment.

In a further embodiment of the syringe, the penetration means at the end proximate the plunger may be bent radially, and mate with a groove formed in the end of the plunger proximate to the bent end of the penetration means, the bent end of the penetration means and the groove in the plunger being engaged by rotating the plunger relative to the barrel of the syringe.

The needle engaging means in the syringe can be a dual female thread combination, the dual threads being formed in opposite ends of the engaging means, and a male thread means being formed on the exterior of the engaging means outside one of the female threads, the exterior male thread means being of opposite thread rotation to the dual female thread means. The end of the needle proximate to the engaging means can have a male thread removably engageable with the proximate female thread of the engaging means. The plunger proximate to the engaging means can have a male thread engageable with the female thread of the engaging means opposite to the female thread engaging the male thread of the needle means.

The invention also relates to an adapter for a syringe having a piston and a needle base fitting in the end of the syringe comprising: (a) a protrusion formed at one end of the adapter for fitting inside the hollow of a base affixed to a syringe needle; (b) releasable engagement means formed in the exterior of the adapter and being adapted to releasably engage with the interior of the needle receiving end of a syringe barrel; and (c) an engagement means formed in the end of the adapter opposite the protrusion, said engagement means being adapted to engage with the piston end of a syringe plunger.

The piston engaging means of the adapter can be a spiral thread and the releasable engagement means can be a male thread. The penetration means of the syringe can be releasably engaged with the end of the barrel means by means of an adapter, and the adapter means can be adapted to engage with the engaging means at the end of the plunger means proximate to the penetration means by rotating the plunger means. The adapter means can be releasably connected to the end of the barrel means by a female-male thread combination, and the means of the adapter means adapted to engage the engaging means of the plunger means can be a spiral thread combination with locking means.

The penetration means of the syringe can be a needle which is fitted with a Luer lock, the Luer lock being engaged with the adapter means. The needle-Luer lock combination and the adapter can be disengaged from the end of the barrel means by latch means which engages with the adapter when the plunger means is pushed to the needle end of the barrel and rotated to minimally withdraw and activate the engagement means.

The adapter can protrude partially from the penetration means end of the hollow barrel means and can have a thread direction which is the same as or opposite to the thread direction of the barrel means engaging the penetration means. The adapter can be designed to protrude partially from the penetration end of a syringe barrel.

In a further embodiment of the syringe the plunger is hollow and is a circular cylinder in cross section with a fastening means such as threads at the finger press end of the plunger. The plunger additionally includes a narrowed weakened break point whereby the hollow cylindrical portion of the plunger upon being withdrawn from the barrel may be broken away and fastened to the opposite end of the barrel whether or not the needle assembly has been withdrawn into the interior. Such construction allows for redundant manners of sheathing the needle assembly through the use of a needle guard or the cylindrical portion of the plunger. Both include threaded ends of the same size for attachment to the barrel and are relatively larger and more safely used than prior devices. Some additional features improve syringe function, for example, by enhancing the readability of calibration markings and thus improving the accuracy of the syringe.

In a still further embodiment of the invention, the needle guard and the hollow cylindrical portion of the plunger are the same element. That is to say, the circular cylinder portion of the plunger includes at a narrowed intermediate point a reusable connection means in lieu of a break point. Such construction allows this portion of the plunger to be disconnected from the needle end portion of the plunger and used as a needle guard. Subsequently, this portion may be removed from the end of the barrel and reconnected to the needle end portion of the plunger. Moreover, such construction allows the interior of the syringe body to be sealed at both ends when the needle end portion of the plunger is withdrawn and the hollow cylindrical portion is in place on the barrel as a needle guard.

Additional features found in the further exemplary embodiments are the use of colored material for the plunger, which due to its close proximity to the inner surface of the barrel provides a less distorted or clearer background for viewing the barrel calibration markings. Still further, the inclusion of a radially linear surface on the interior far end of the plunger bung, as well as using bung material of the same color as the plunger, presents a single flat interface which dramatically improves the visualization of the calibration markings and the alignment of the end of the plunger with such markings. More accurate filling and delivery of contents is then possible.

Still further beneficial features of the disclosed exemplary embodiments include the use of annular ridges on the interior of the barrel and/or on the exterior of the plunger whereby the sealing ridges in combination with a needle guard attached to the opposite end of the syringe maintains sterile conditions in the syringe interior prior to use and after use seals bacteria or other material within the body of the syringe.

Additional features to be found in the exemplary embodiments include a cup-like annular lip or resilient pronged projections on the plunger adjacent the portion at the break point which are used in combination with the interior ridges of the barrel at the finger press end to deter the needle assembly from being completely withdrawn from the interior of the barrel means. Such elements also retain the needle assembly at the finger press end of the barrel. As an additional feature of the exemplary embodiments, the needle assembly includes an adapter-plunger connection which is designed to allow unidirectional torque only so as to prevent re-attachment of the adapter to the barrel means without the use of a special tool. Thus, subsequent use of the needle once the adapter and barrel have separated is prevented in the absence of special tools or extraordinary measures.

A further feature of the present invention resides in the provision of a venting structure in the adapter for venting air from the interior of the barrel once the barrel has been substantially filled with fluid to be injected and prior to injection. As well know, it is important that air be expelled entirely from the barrel so that air may not be injected with the fluid. In certain embodiments hereof, the hub or adapter, which releasably secures the needle to the distal end of the barrel and is adapted to be withdrawn with the needle from the distal end of the barrel into the interior of the barrel, has a connective structure which enables the plunger to grasp the adapter and withdraw the adapter and needle into the interior of the barrel. This connective structure protrudes toward the interior of the barrel, forming an annular space between it and the side walls of the barrel at the barrel's distal end. When the axially extending fluid passage passes entirely through the adapter opening into the interior of the barrel at a location spaced from the distal end of the barrel, there is the danger that air can be trapped in such annular space notwithstanding movement of the plunger toward the distal end to vent the air. That is, the fluid in the barrel may occlude the central passage, and prevent the air trapped in the annular space from venting.

Therefore, in accordance with another aspect of the present invention the adapter is provided with one or more vent passages which open into the annular space at the most superior portion of the hollow barrel when the syringe is oriented substantially vertically with the needle uppermost. Consequently, after the fluid has been withdrawn into the interior of the barrel and the syringe oriented vertically needle end up, air is expelled through the vent passage into the central passage by moving the plunger toward the distal end of the barrel. The central passage may extend wholly through the adapter whereby the vent passage forms one or more branch passages of the central passage. Alternatively, the central passage may terminate within the adapter with more vent passages serving not only as air vents but passages for flowing the fluid through the needle during injection. To ensure that the vent passage(s) opens at the superior position in the interior of the barrel, the face of the radially enlarged portion of the adapter facing oppositely of the distal end of the barrel may be tapered radially inwardly toward the distal end of the barrel. Additionally, radial grooves may extend in the tapered adapter face and constitute continuations of the vent passages. Further, one or more annular grooves may be disposed in the tapered adapter face in communication with the radial grooves and vent passages, all to ensure venting of air from the syringe prior to use.

A further desirable feature of a syringe is that it may be packaged and sterilized in bulk and not necessarily in individual packages. However, this leaves open the possibility of tampering or inadvertent disruption of seals and contamination. It is important, therefore, that the syringe hereof embody tamperproof features. To that end, in one embodiment hereof, tamperproofing can be accomplished by applying a strip of paper tape having adhesive along one side along the side of the syringe covering both the junctures of the needle guard and body of the syringe and the proximal end of the barrel and plunger. Thus, if the tape has been broken or is twisted or otherwise removed from the syringe, it would be evident that the seals at the opposite ends of the syringe have possibly been disrupted. Similarly, in another embodiment hereof, a tight shrink-wrap of plastic material may be provided about these junctures. Again, removal of the shrink-wrapped plastic material or a twisting or severing thereof would indicate a possible disruption of or tampering with the seals. In a further form of the invention, the syringe may be dipped into a plastic material in liquid form whereby a thin-film coating is applied to and solidified about the entire outer surface of the syringe, including the needle guard and projecting portion of the plunger. Consequently, sterility may be maintained, provided the thin-film plastic coating is not broken, while at the same time, disruption of or tampering with the seals at the aforementioned junctures is readily evident.

In a preferred embodiment according to the present invention, there is provided a syringe comprising (a) a hollow, axially elongated barrel, (b) an adapter carried by the barrel adjacent a distal end thereof and removable therefrom in response to rotation relative to the barrel, the adapter carrying a needle and providing fluid communication with the interior of the hollow barrel, (c) a plunger axially movable in the barrel and (d) an adapter engagement structure disposed at the distal end of the plunger and engageable with a mating connection engagement structure on the adapter, the structures having respective drive and connective engagement surfaces, the drive surfaces being engageable with one another in response to axial movement of the plunger toward the distal end of the barrel and jointly movable upon engagement to enable rotation of the adapter relative to the barrel in response to relative rotation of the plunger and barrel to cause the adapter to part from the distal end of the barrel, the connective surfaces being engageable with one another to connect the plunger and adapter one with the other and enable the adapter, when parted from the end of the barrel in response to joint rotation of the adapter and the plunger relative to the barrel, to be withdrawn with the needle into the interior of the barrel in response to joint axial movement of the plunger and the adapter in a direction away from the distal end of the barrel.

In a further preferred embodiment according to the present invention, there is provided a syringe comprising (a) a hollow, axially elongated barrel, (b) an adapter carried by the barrel adjacent a distal end thereof and removable therefrom in response to rotation relative to the barrel, the adapter having a hub for carrying a needle and providing fluid communication with the interior of the hollow barrel, (c) a plunger axially movable in the barrel and (d) an adapter engagement structure disposed at the distal end of the plunger and engageable with a mating connection engagement structure on the adapter, the structures having respective drive and connective engagement surfaces, the drive surfaces being engageable with one another in response to axial movement of the plunger toward the distal end of the barrel and jointly movable upon engagement to enable rotation of the adapter relative to the barrel in response to relative rotation of the plunger and barrel to cause the adapter to part from the distal end of the barrel, the connective surfaces being engageable with one another to connect the plunger and adapter one with the other and enable the adapter, when parted from the end of the barrel in response to joint rotation of the adapter and the plunger relative to the barrel, to be withdrawn with any needle carried thereby into the interior of the barrel in response to joint axial movement of the plunger and the adapter in a direction away from the distal end of the barrel.

In a still further preferred embodiment according to the present invention, there is provided a syringe comprising (a) a hollow, axially elongated barrel having distal and proximal ends, the barrel at the distal end having interior female threads, (b) an adapter carried by the barrel adjacent a distal end thereof and having male threads for threaded engagement with the female threads, the adapter being unthreadable and removable from the distal end of the barrel in response to rotation of the adapter relative to the barrel, the adapter having a central fluid opening and carrying a needle for providing fluid communication with the interior of the hollow barrel, (c) a plunger axially movable in the barrel and projecting from the proximal end thereof terminating in a finger press external of the barrel and (d) an adapter engagement structure disposed at a distal end of the plunger and engageable with a mating plunger engagement structure on the adapter, the structures having respective drive and connective engagement surfaces, the drive surfaces being engageable with one another and jointly movable when engaged to enable rotation of the adapter relative to the barrel in response to relative rotation of the plunger and barrel to cause the adapter to unthread from the distal end of the barrel, the connective surfaces comprising a respective rib and groove engageable with one another in response to axial movement of the plunger toward the adapter to connect the plunger and adapter one with the other and enable the adapter, when unthreaded from the distal end of the barrel in response to joint rotation of the adapter and the plunger relative to the barrel, to be withdrawn with the needle into the interior of the barrel upon joint axial movement of the plunger and the adapter in a direction away from the distal end of the barrel.

In a still further preferred embodiment according to the present invention, there is provided a syringe comprising (a) a hollow, axially elongated barrel, (b) an adapter carried by the barrel adjacent a distal end thereof and removable therefrom in response to rotation relative to the barrel, the adapter carrying a needle and providing fluid communication with the interior of the hollow barrel, (c) a plunger axially movable in the barrel, (d) adapter engagement structure disposed at the distal end of the plunger and engageable with a mating connection engagement structure on the adapter, the structures having respective drive and connective engagement surfaces, the drive surfaces being engageable with one another and jointly movable when engaged to enable rotation of the adapter relative to the barrel in response to relative rotation of the plunger and barrel to cause the adapter to part from the distal end of the barrel, the connective surfaces being engageable with one another to connect the plunger and adapter one with the other and enable the adapter, when parted from the end of the barrel in response to joint rotation of the adapter and the plunger relative to the barrel, to be withdrawn with the needle into the interior of the barrel in response to joint axial movement of the plunger and the adapter in a direction away from the distal end of the barrel and (e) the plunger having a first portion projecting from the proximal end of the barrel and a second portion within the barrel when the adapter and needle are withdrawn into the barrel, the first portion being removable from the second portion, barrel including a catch for preventing removal of the second portion of the plunger from the proximal end of the barrel when the adapter and needle are withdrawn into the barrel, a proximal end of the first portion of the plunger and the distal end of the barrel having surfaces engageable with one another upon removal of the first plunger portion from the second plunger portion and engagement of those surfaces with one another to close the distal end of the barrel after withdrawal of the adapter and needle from the distal end of the barrel.

DRAWINGS

In the drawings which illustrate specific embodiments of the invention, but which should not be construed as restricting the spirit or scope of the invention in any way:

FIG. 8 illustrates a side elevation partial-section view of a second embodiment of the syringe with a screw-lock plunger-needle hub connection;

FIG. 9 illustrates a detailed side elevation partial-section view taken along section A—A of FIG. 11 of a first design of a plunger with a right-hand or left-hand cam-lock rotation to secure the plunger to the needle hub for withdrawing the needle into the barrel of the syringe;

FIG. 10 illustrates a detailed side elevation partial-section view taken along section A—A of FIG. 11 of a second design of a plunger with a right-hand or left-hand cam-lock rotation to secure the plunger to the needle hub and a second right-hand or left-hand rotation locking means which provides a double locking action between the plunger and needle hub;

FIG. 11 illustrates an end elevational view of the needle end of the syringe illustrated in FIG. 8;

FIG. 12 is a section view taken along section line B—B of FIG. 9 showing the syringe barrel handle and syringe plunger handle at a 45° angle to one another to activate the right-hand rotation cam locking action;

Figure 14:
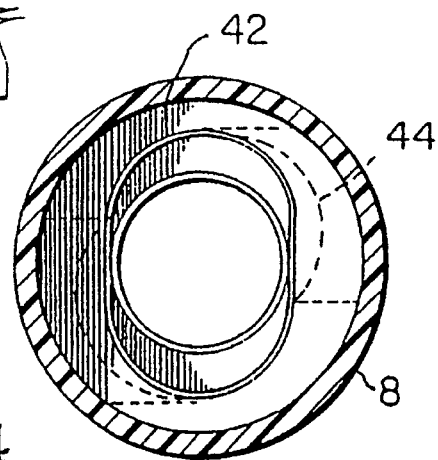
Figure 15:
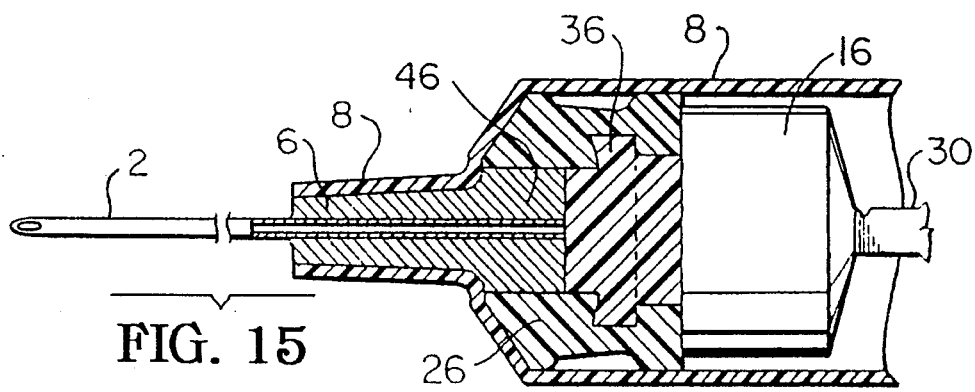
Figure 16:
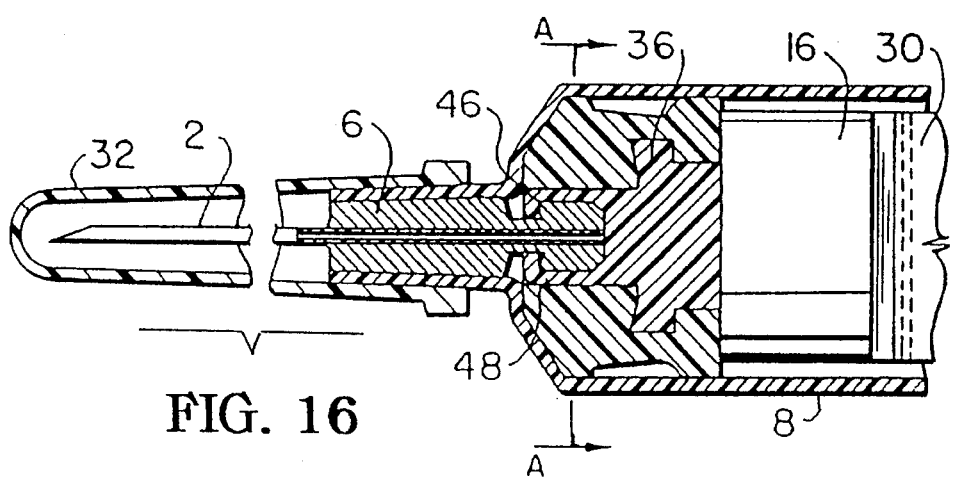
Figure 17:
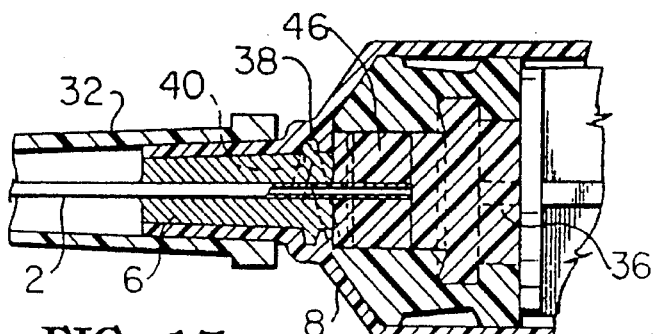
Figure 18:
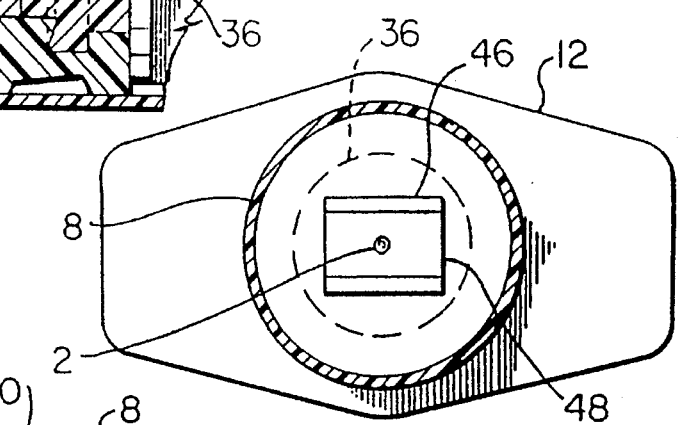
Figure 19:
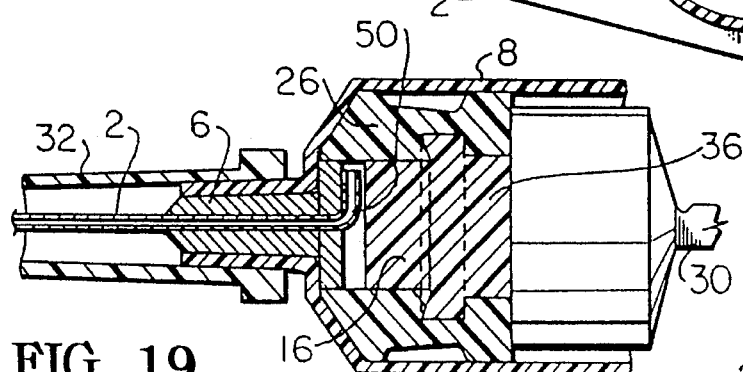
Figure 20:
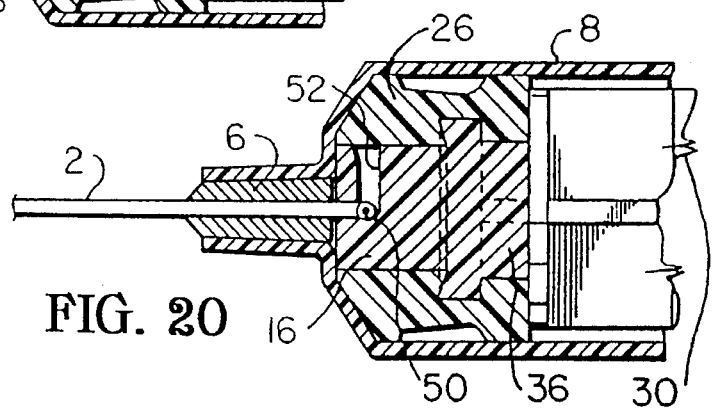
Figure 21:
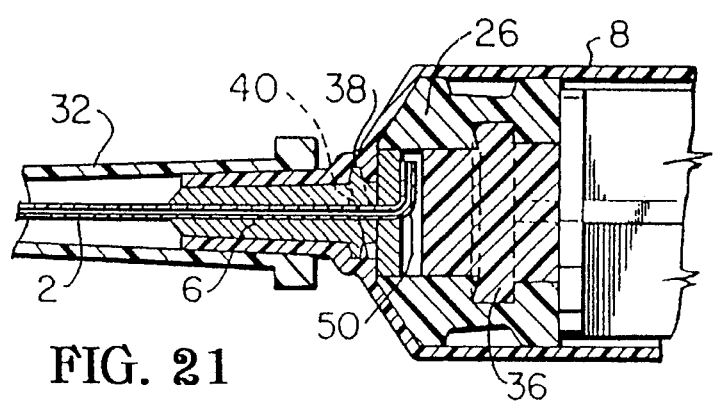
Figure 22:
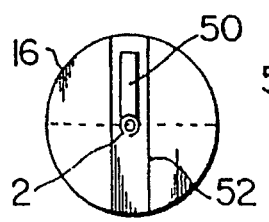
Figure 23:
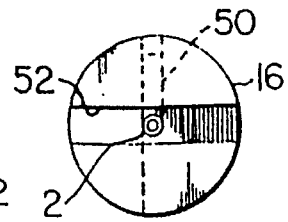
Figure 24:
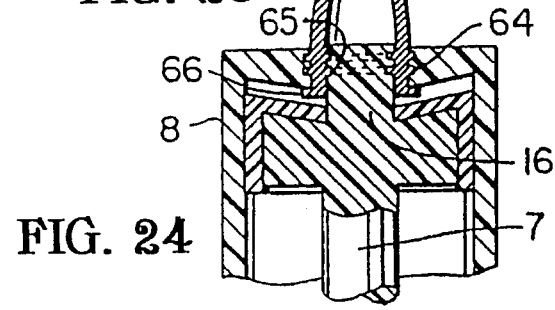
Figure 25A:
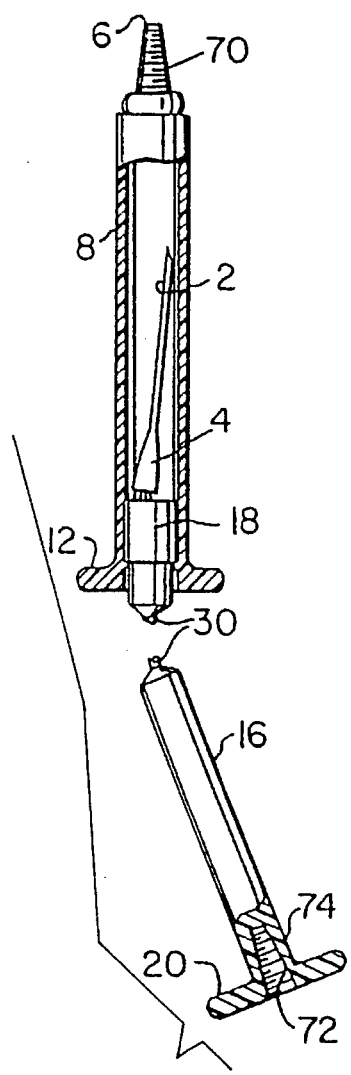
Figure 25B:
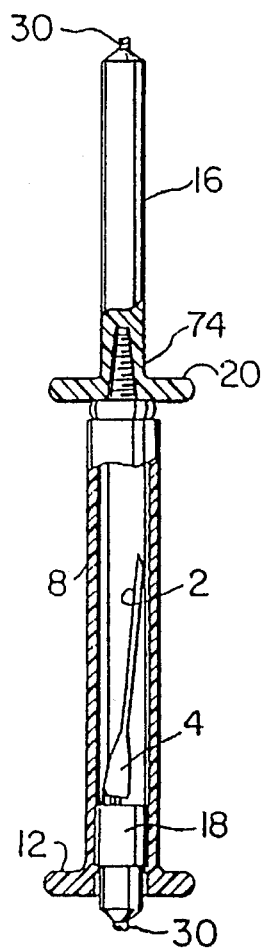
Figure 33:
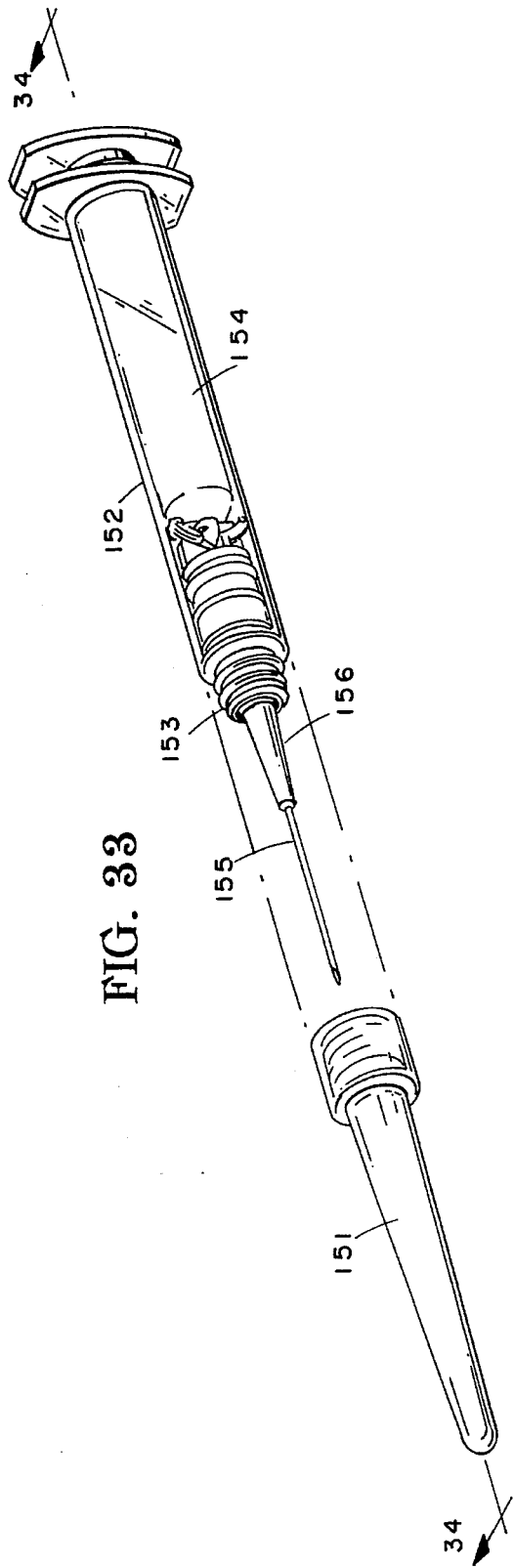
Figure 34:
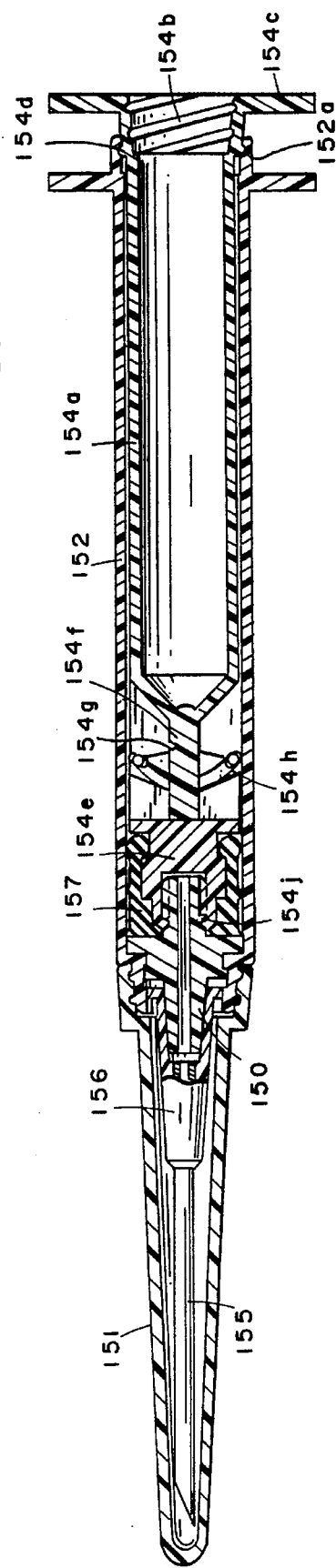
Figure 38:
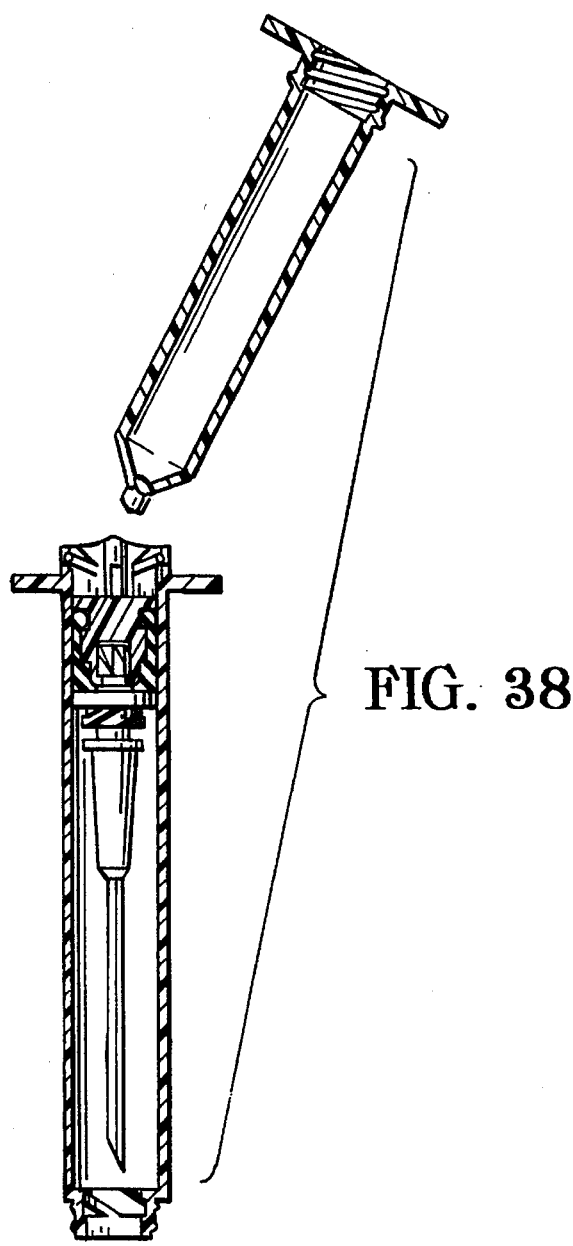
Figure 39:
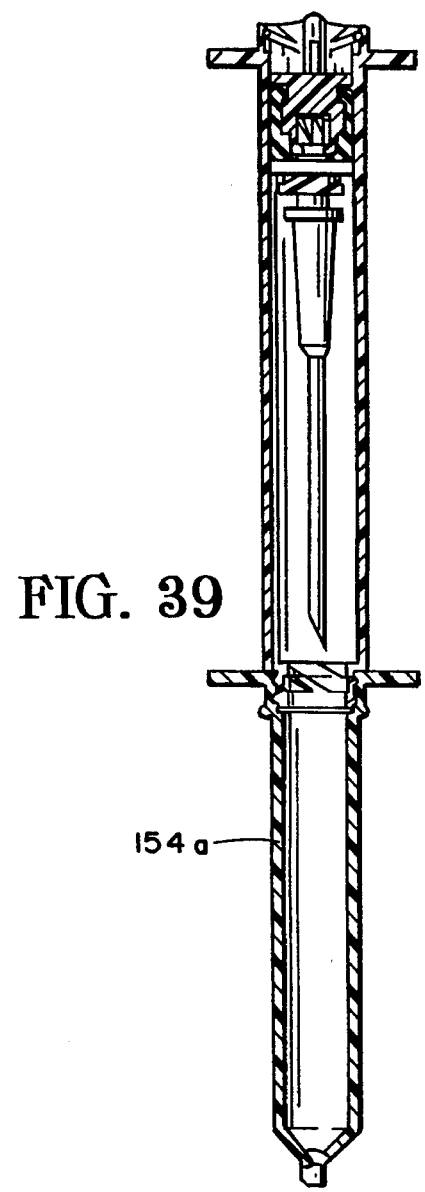
Figure 40:
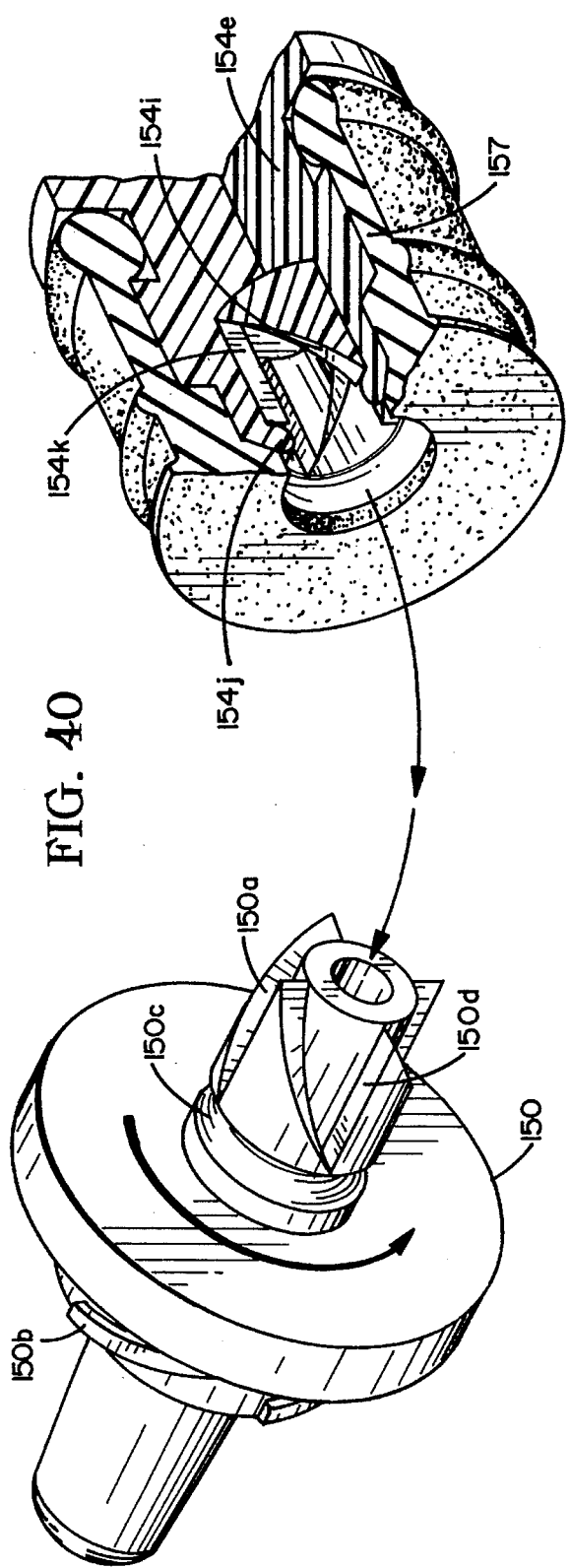
Figure 42:
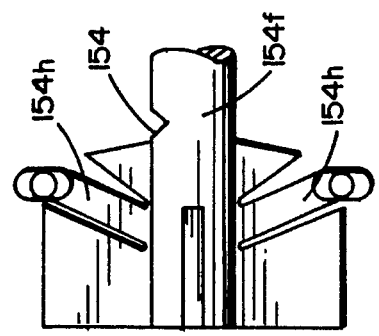
Figure 41:
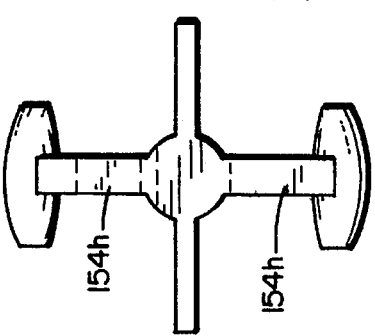
Figure 45:
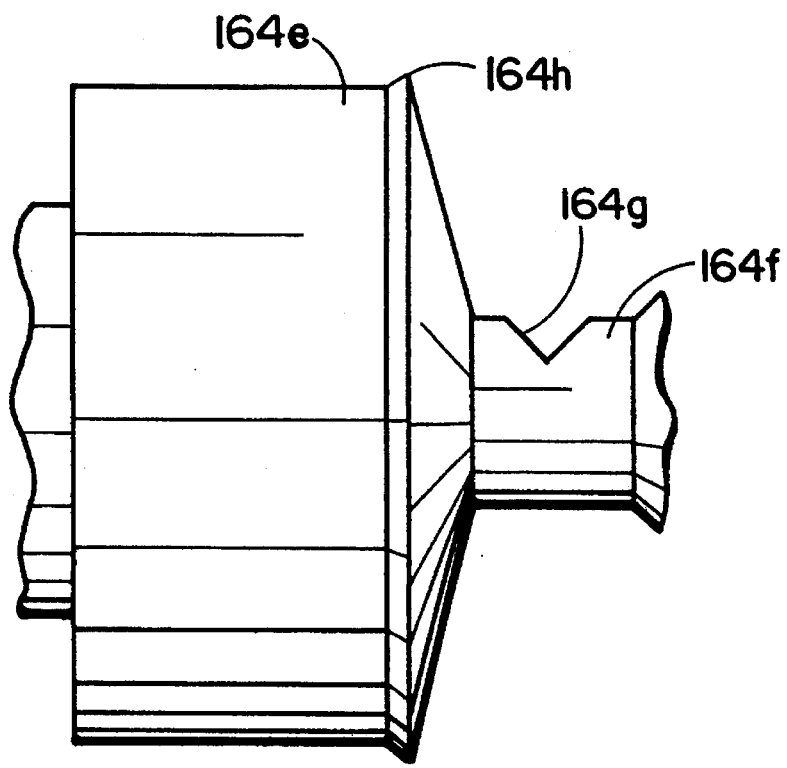
Figure 47:
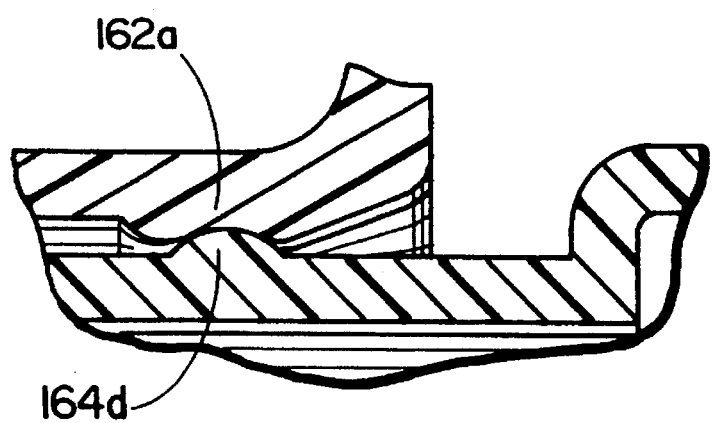
Figure 51:
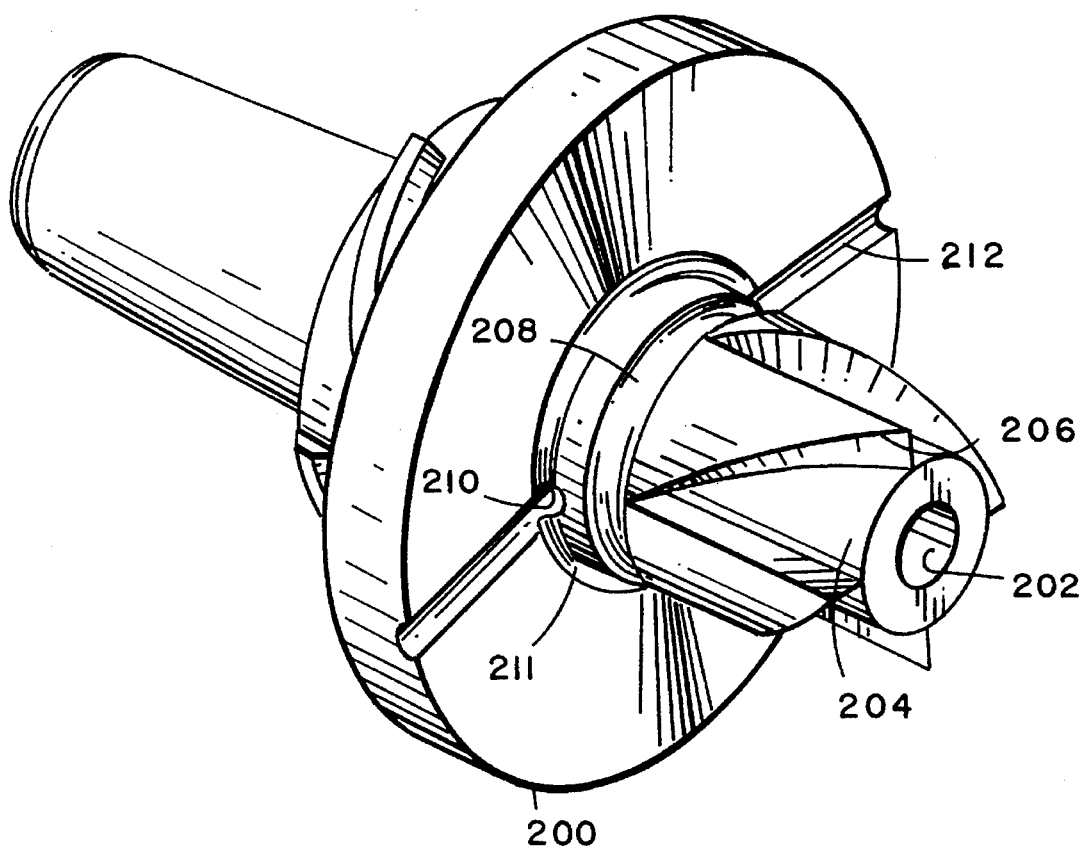
Figure 52:
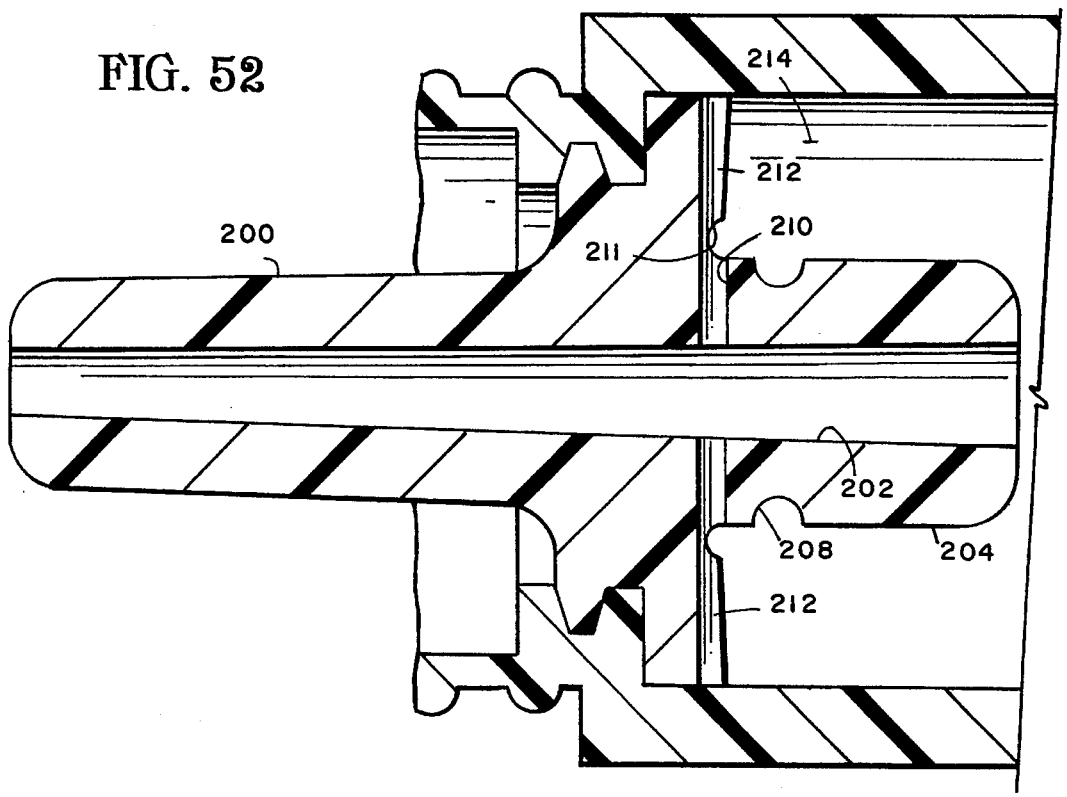
Figure 53:
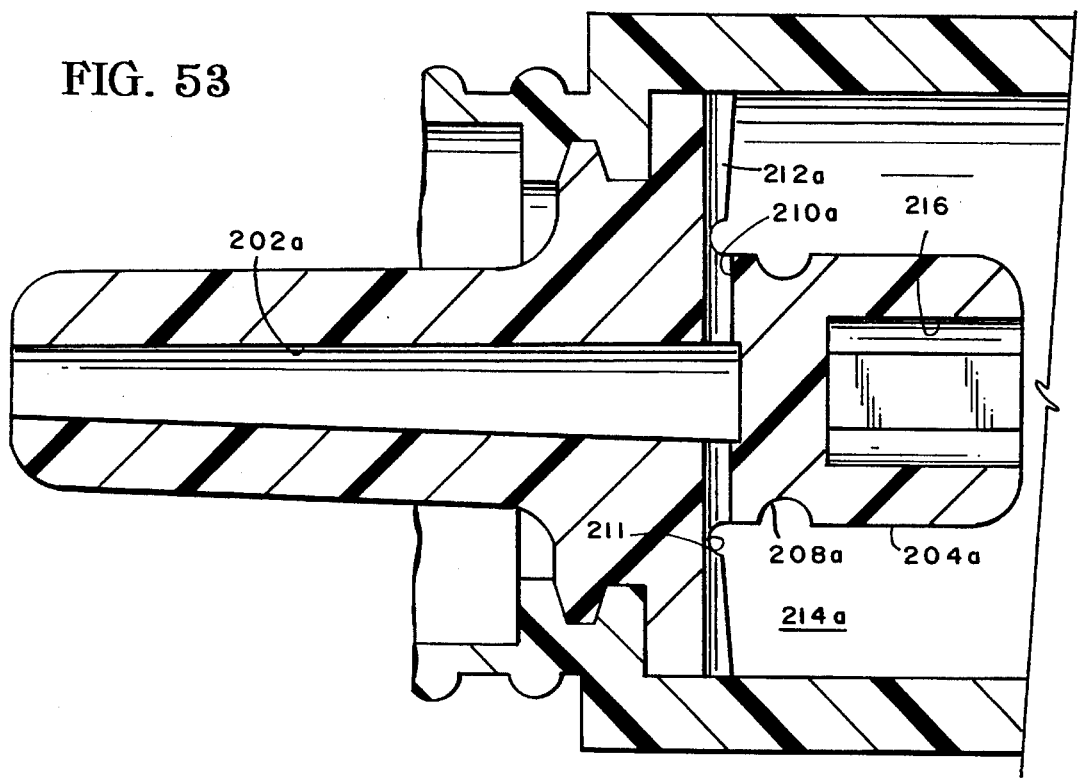
Figure 54:
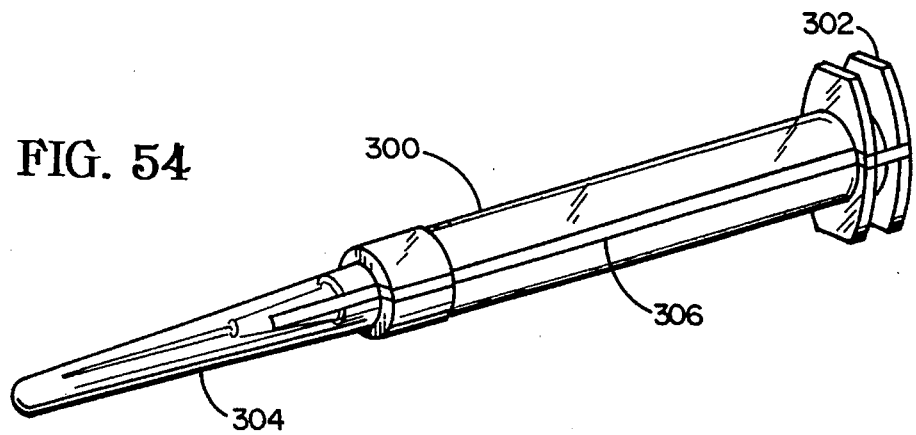
Figure 55:
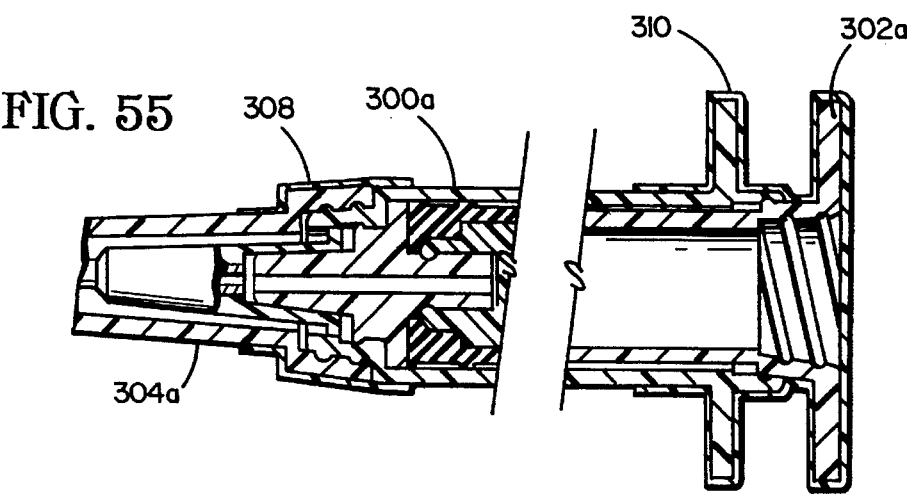
Figure 56:
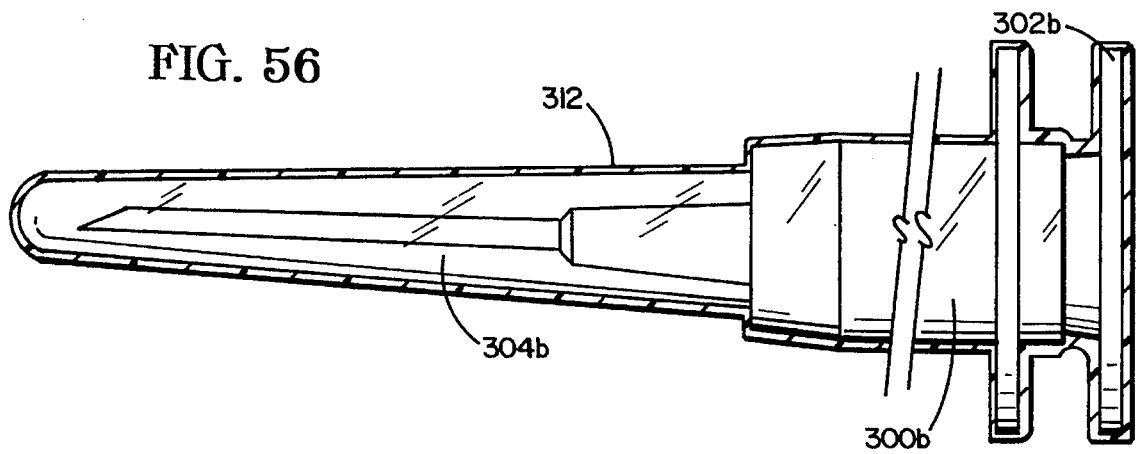
Figure 58:
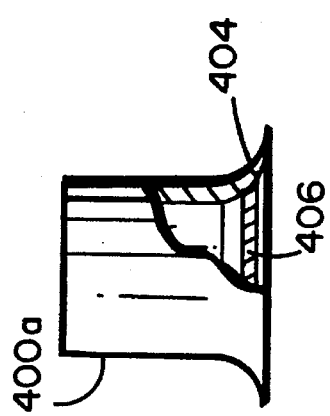
Figure 59:
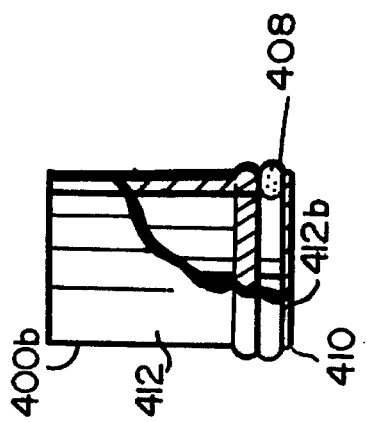
Figure 57:
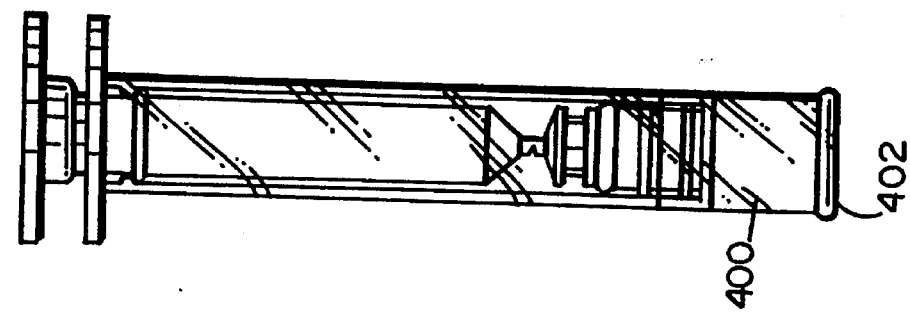

FIG. 14, which appears on the same sheet as FIG. 11, illustrates a detailed end elevation view of the cam lock mechanism of the embodiment of the syringe illustrated in FIG. 9;

FIG. 15 illustrates a top elevation partial-section view of a plunger with a snap-on socket type needle hub connection;

FIG. 16 illustrates a side elevation partial-section view of a plunger with a snap-on socket type needle hub connection;

FIG. 17 illustrates a top elevation partial-section view of a plunger with a snap-on socket type needle hub connection combined with a right-hand rotation option;

FIG. 18 illustrates a section view taken along section line A—A of FIG. 16;

FIG. 19 illustrates a side elevation partial-section view of a bent needle embodiment of a needle hub connection;

FIG. 20 illustrates a top elevation partial-section view of a bent needle embodiment of a needle hub connection;

FIG. 21 illustrates a side elevation partial-section view of a bent needle embodiment of a needle hub connection coupled with a right-hand rotation option;

FIG. 22 illustrates a detailed end view of the diagonal slot in the end of the piston-plunger with the bent needle end fitted in the slot;

FIG. 23 illustrates a detailed end view of the diagonal slot in the end of the piston-plunger rotated in the slot to grip the bent end of the needle;

FIG. 24 illustrates a side elevation partial-section view of an embodiment of the syringe wherein the needle and hub are rotatably detachable from the barrel and the plunger threadedly engages the interior of the hub;

FIG. 25a illustrates a side elevation partial-section view of the syringe with the needle and hub drawn within the interior of the barrel and the remote end of the plunger that is broken away, formed with a hollow threaded cap-like opening;

FIG. 25b illustrates a side elevation partial-section view of the syringe with the broken away plunger portion threadedly engaged with the male threaded end of the hub at the top of the barrel;

FIGS. 25c and 25d illustrate sequential side elevation views of an alternative design of syringe where the part of the plunger adjacent the break away weak point is threaded and is screwed into the opening in the end of the barrel vacated by the needle and hub when pulled into the barrel;

FIG. 26 illustrates a side elevation partial-section view of an embodiment of the syringe wherein the piston is adapted with a latch which snaps into place in an adapter after the piston is fully depressed and rotated;

FIG. 27 illustrates a side elevation partial section view of an adapter which mates with the needle platform;

FIG. 28 illustrates a side elevation section view taken along section line C—C of FIG. 2g;

FIG. 29 illustrates an end view of the latch mechanism of the piston depicted in FIG. 26;

FIG. 30 illustrates a side elevation view of an alternative design of adapter;

FIG. 31 illustrates a side elevation partial section view of the alternative design of adapter;

FIG. 32 illustrates a side elevation partial section view of an embodiment of the syringe wherein an adapter is mounted allowing Luer locked needles to be used and interchanged but permitting subsequent withdrawal of a used needle and adapter into the barrel;

FIG. 33 illustrates a perspective view partially in phantom of a still further embodiment of a syringe, a needle guard and the threaded connection therebetween;

FIG. 34 shows a side elevation view partially in section of the syringe embodiment of FIG. 33;

FIG. 35 illustrates a different side elevation view of the embodiment of FIG. 33 in partial section view and with the needle guard removed;

FIG. 36 illustrates a manner in which the plunger may be rotated with respect to the barrel in order to disconnect the needle assembly from the barrel for withdrawal of the assembly into the barrel;

FIG. 37 is a side sectional view similar to that illustrated in FIG. 34 but with the needle assembly unfastened from the distal end of the barrel and with the assembly withdrawn into the barrel;

FIG. 38 is a side sectional view similar to that illustrated in FIG. 37 but with the hollow cylindrical portion of the plunger broken away at the break point;

FIG. 39 is a side elevational view partially in section with the hollow cylindrical plunger portion fastened to the distal end of the barrel after the cylindrical plunger portion has been broken away at the break point;

FIG. 40 is a perspective view partially in section of the adapter and the distal end of the plunger illustrating the mating relationship of the noted elements;

FIG. 41 is an axial view illustrating a pair of resilient prongs used to engage a groove at the finger press distal end of the barrel for retaining the needle assembly in the retracted position in the barrel;

FIG. 42 is a partial side view of the pronged latching device of FIG. 41;

FIG. 43 is a side elevational view partially in section of a still further exemplary and presently preferred embodiment of the invention;

FIG. 44 illustrates a section view of a portion of the plunger taken along section line 44—44 of FIG. 43;

FIG. 45 is a detailed partial side elevation view of a portion of the plunger including the narrowed portion of the plunger which contains the break point as illustrated in FIG. 43;

FIG. 46 is an enlarged sectional view illustrating a portion of the radially linear interface between the adapter and the plunger bung;

FIG. 47 is an enlarged partial sectional view of ridges and an intervening groove on the inside surface of the barrel at the distal end and a corresponding annular ridge on the exterior surface of the hollow portion of the plunger which cooperates with the annular barrel ridges for locking and sealing purposes;

FIG. 48 is a side elevational view partially in section of a still further embodiment of the invention which represents a modification of the embodiment of FIG. 43;

FIG. 49 is a side elevational view partially in section of the embodiment of FIG. 48 illustrating the cylindrical plunger portion disconnected from the needle end portion of the plunger;

FIG. 50 illustrates a partial end view of the plunger taken along line 50—50;

FIG. 51 is a perspective view of an adapter constructed in accordance with a still further embodiment of the present invention;

FIG. 52 is an enlarged fragmentary cross-sectional view illustrating the adapter of FIG. 51 disposed in the distal end of the barrel;

FIG. 53 is a view similar to FIG. 52 illustrating a further form of the adapter;

FIG. 54 is a perspective view of one form of a tamperproof syringe constructed in accordance with the present invention;

FIG. 55 is an enlarged fragmentary cross-sectional view with parts broken out illustrating another form of a tamperproof syringe;

FIG. 56 is an enlarged side elevational view with parts broken out and illustrating the opposite ends of a syringe having a tamperproof coating according to the present invention;

FIG. 57 is a side elevational view of a syringe with the barrel end capped prior to use;

FIGS. 58 and 59 are enlarged side elevational views of two additional embodiments of caps for capping the end of the syringe barrel;

FIGS. 60–62 are side elevational views schematically illustrating the series of steps for re-applying the cap illustrated in FIG. 58 to the barrel end of the syringe after use of the syringe; and FIGS. 63 and 64 are side elevational views of a further form of syringe hereof and illustrating its manner of use.

Figure 68:
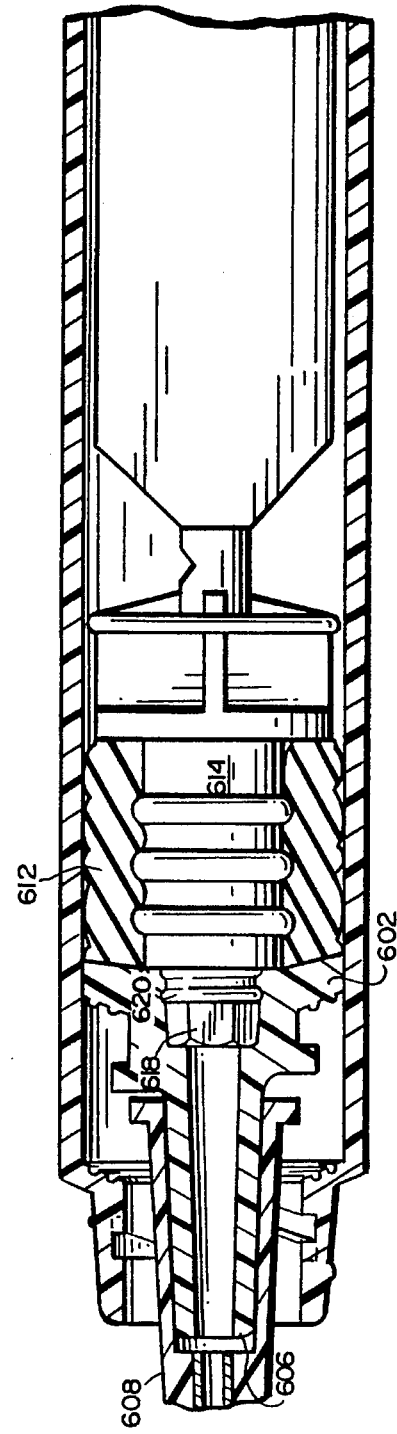
Figure 69:
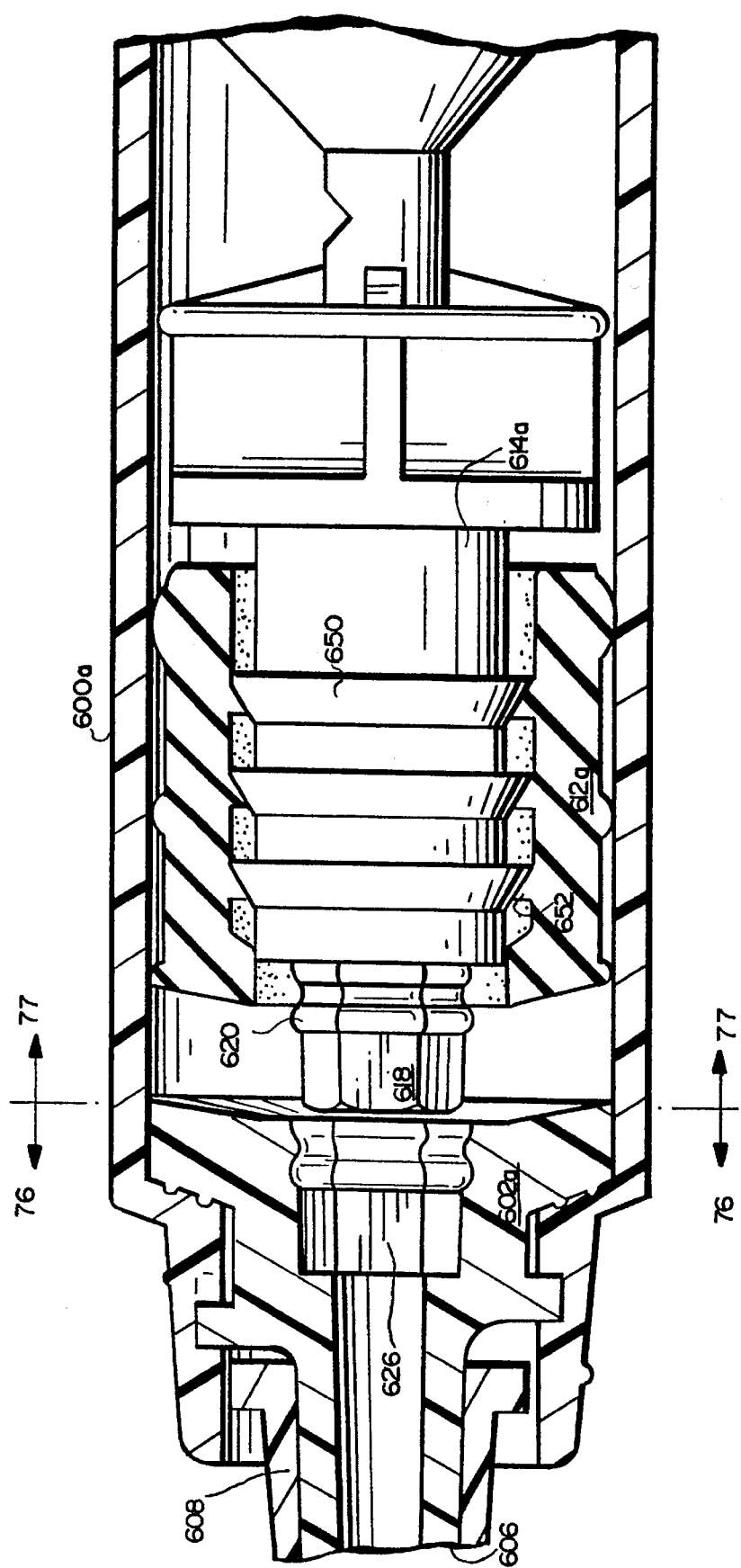
Figure 70:
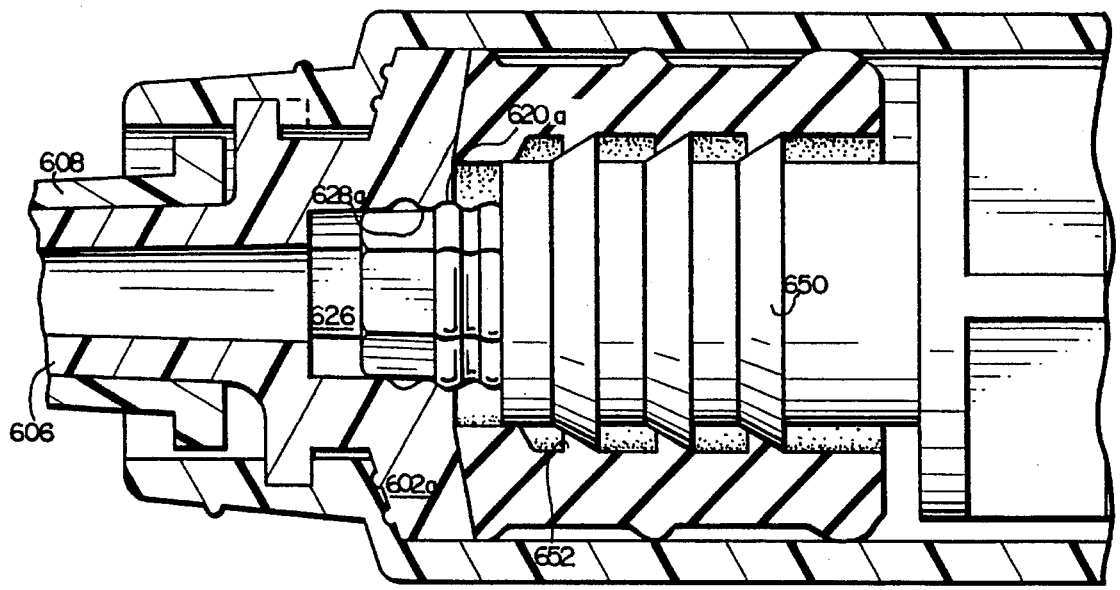
Figure 71:
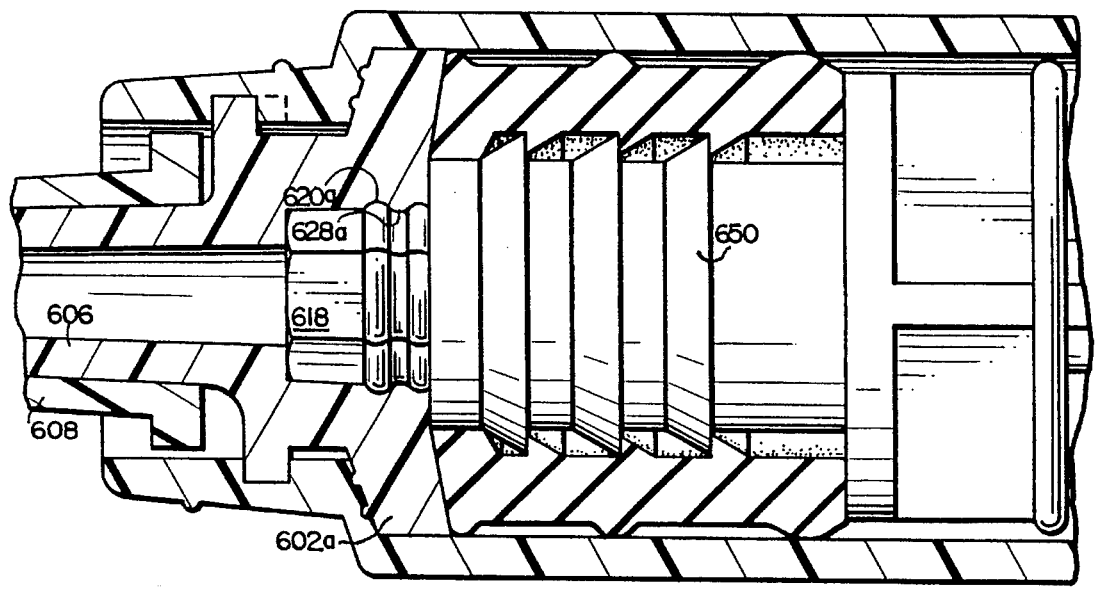
Figure 72:
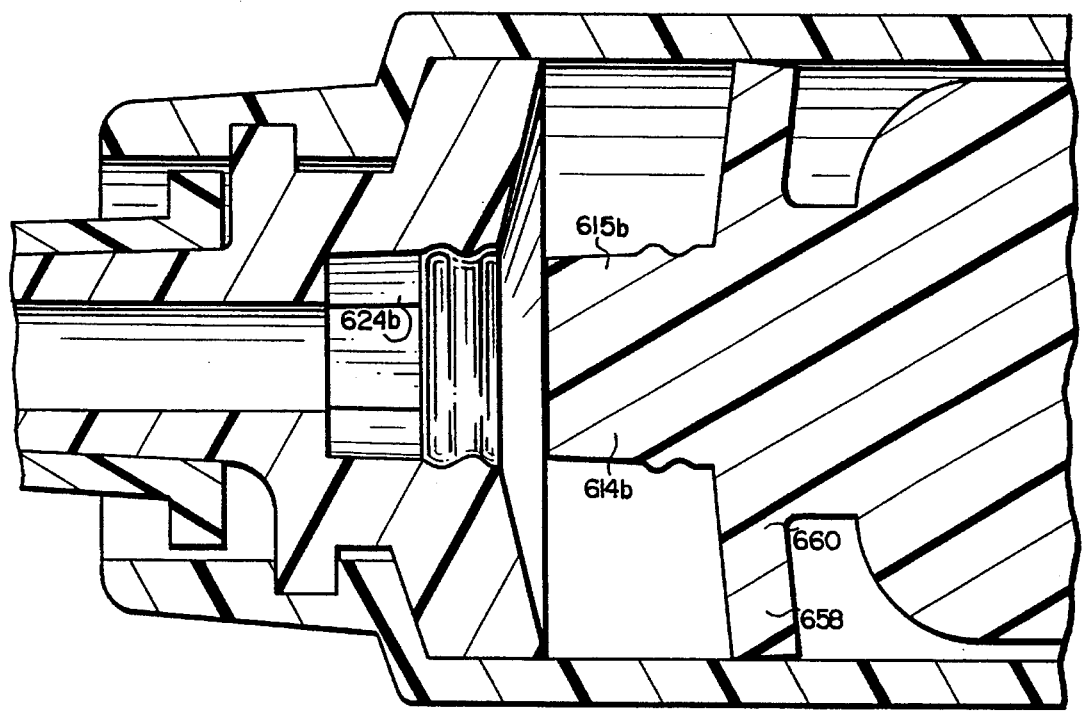
Figure 73:
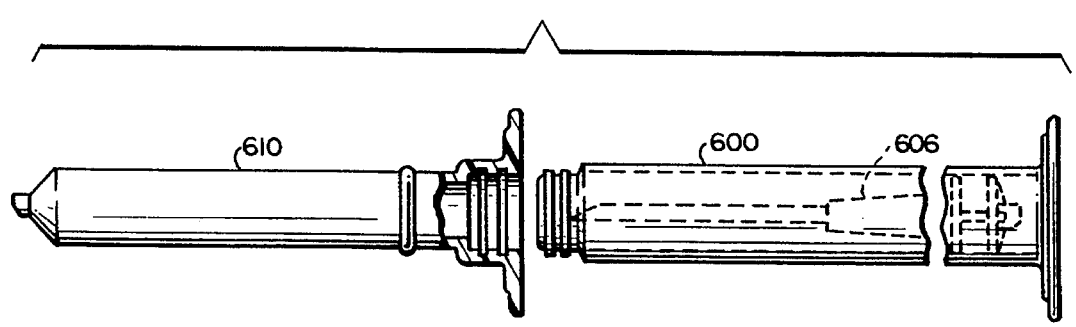
Figure 74:
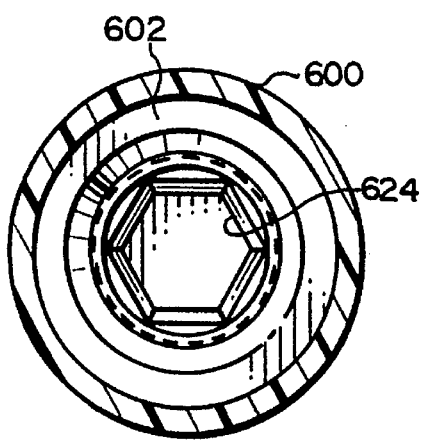
Figure 75:
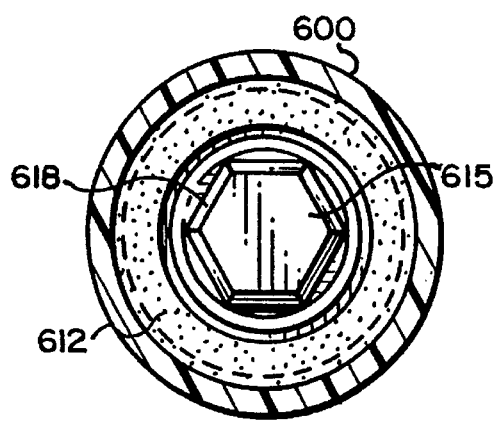

FIGS. 65–68 are fragmentary cross-sectional views of a still further embodiment of syringe hereof wherein the plunger is permanently locked to the adapter upon axial displacement of the plunger into final seated position relative to the adapter;

FIGS. 70 and 71 are enlarged views similar to the embodiments of FIGS. 65–69, illustrating a still further embodiment for permanently locking the plunger and adapter to one another;

FIG. 72 is a view similar to FIG. 70 illustrating a still further embodiment of the syringe hereof;

FIG. 73 is a schematic illustration of the coupling between the proximal end of the plunger and the distal end of the barrel once the adapter and needle have been withdrawn into the barrel;

FIGS. 74 and 75 are cross-sectional views of the embodiment of FIGS. 65–69 taken generally about on lines 74—74 and 75—75 in FIG. 65

Figure 76:
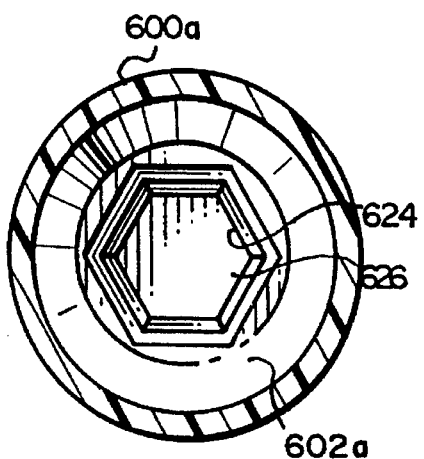
Figure 77:
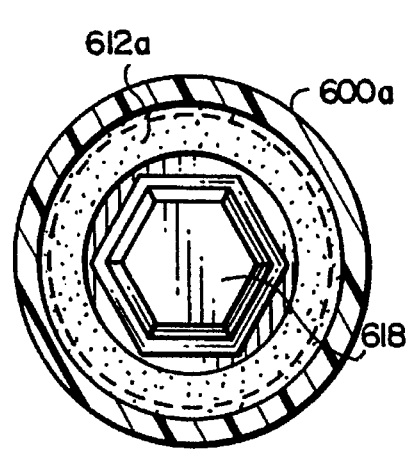

FIGS. 76 and 77 are views similar to FIGS. 74 and 75 taken generally about on lines 76—76 and 77—77 in FIG. 69;

FIG. 78 is a fragmentary cross-sectional view illustrating an adapter and plunger end combination in accordance with a further form of the present invention; and FIG. 79 is a view similar to FIG. 78 illustrating the adapter and plunger end in engagement with one another in the end of a syringe barrel.

DETAILED DESCRIPTION OF SPECIFIC EMBODIMENTS OF THE INVENTION

Most disposable syringes can be used with a variety of interchangeable needles with different diameter and length. The needles are connected by what is known as a Luer connector, which may be of two types. One is a simple conical device which accepts the needle base. This version is often described as a Luer tip. To detach the needle, it is simply pulled off. The other connector type is often described as a Luer lock. The Luer lock has a simple screw thread locking mechanism that permits the base of the needle to be screwed onto the syringe so that it cannot be pulled off without unscrewing. In this disclosure, the universal coupling mechanism connecting the needle to the syringe will be referred to as a Luer lock version of the Luer connector unless otherwise indicated. It should be recognized that the claims to the invention relate to both the plain Luer tip and the Luer lock mechanisms. The interchangeability capability of a Luer lock allows for the most appropriate needle to be used for syringe filling and patient injection. In many cases, to save time, a different larger needle is used to fill the syringe with fluid prior to injection. A needle of fine calibre to minimize pain to the patient, and tissue damage, is often used for intramuscular or subcutaneous injection. In addition, if the same needle is used to puncture a vial in order to fill the syringe with medication, there is a potential for contamination of that needle from the vial, if the vial stopper carries a contaminant. Under most circumstances, this would not pose a significant risk. However, if the patient has reduced immunity to infection, the ability to change to an entirely new sterile needle for patient injection may become important.

Although the prior art describes syringes which can protect the needle by a variety of means, including those which involve withdrawing the needle into the interior of the barrel of the syringe, such syringes do not allow for interchangeability of the needle or for the universal Luer lock coupling mechanism which is an important feature of the syringe. Most commercially available syringes employ a Luer lock. Since the subject invention is adapted for use with a Luer lock, it can directly replace syringes currently in use and requires no change in technique or procedure until after the syringe has been used. In addition, most currently produced needles can be used in the usual manner on this syringe.

After use, once the needle has been withdrawn into the barrel, the syringe plunger can be snapped off. It is designed so that it can be screwed onto the front of the syringe and thereby prevent any possibility of the needle within the barrel protruding through the front of the syringe again. This is an important factor for a health care worker using the syringe and also for any health care workers subsequently handling garbage which might contain a contaminated syringe.

This invention pertains to a syringe which, after being used by a health care worker or hazardous industries worker, or the like, to inject medication or fluid into a patient, or withdraw fluid from a patient, or in sampling toxic material, for example, in an industrial process, can be transformed by the worker to withdraw the needle into the barrel of the syringe for disposal purposes, thereby eliminating potentially harmful needle stick injuries among such workers. In industrial applications, the storage of a contaminated needle is similarly effected within the barrel to prevent further contamination of the environment or process.

With any one of the various embodiments of the basic syringe design, the needle is retracted by the user into the interior of the body of the syringe immediately after it is withdrawn, or during its withdrawal, from the patient's body tissue, or after exposure to hazardous situations. Thus, the needle is not exposed for accidental contact at any time after the needle has contacted the potentially hazardous patient's body fluids, or other hazardous materials. This retraction feature eliminates the possibility of potentially dangerous needle stick injuries occurring with contaminated needles.

The safety syringe of the invention is simple to operate and is only slightly more expensive to manufacture than presently used syringes. Another advantage is that the syringe design closely resembles currently used syringes and thus there should be no difficulty in obtaining good acceptance among workers such as medical institutional workers since: the syringe is hermetically sealed before and after use; redundancy of mechanisms allows safe disposal and protection from needle stick injuries and accuracy of reading calibration markings for filling of syringe is more precise. Moreover, the operation of the subject syringe is easy to teach to such workers and requires no unusual skills or manual dexterity.

Syringes that are in current commercial use normally consist of four components, a needle cap which is removed prior to use, a hollow needle which is mounted on a hub with a Luer lock, a barrel to which the hub is attached, and a plunger with a bung (piston) at the head end of the plunger. The plunger is inserted within the barrel head end first and can be pushed into the interior of the barrel in order to pump fluid contained in the barrel out through the interior of the hollow needle. The subject invention, in various embodiments, includes several basic modifications which do not dramatically change the appearance of the conventional syringe.

Figure 1A:
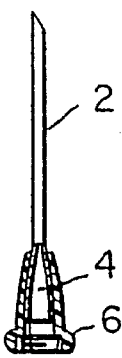
FIG. 1a illustrates a side elevation view of the needle and hub components of a first embodiment of the syringe.
Figure 1B:
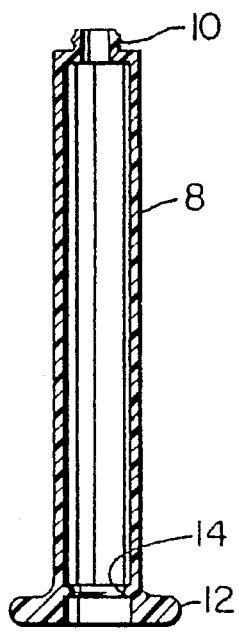
FIG. 1b illustrates a side elevation view of the barrel of a first embodiment of the syringe.
Figure 1C:
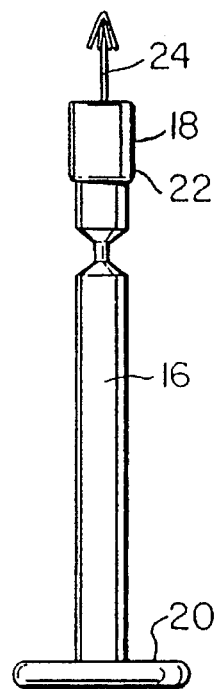
FIG. 1c illustrates a side elevation view of the plunger, bung and hook of a first embodiment of the syringe.
Figure 1D:
FIG. 1d illustrates an end elevation view of the hook.

Referring to the drawings, FIGS. 1a, 1b and 1c illustrate the three basic components which make up a first embodiment of the novel needle retractable syringe. FIG. 1a illustrates in side elevation partial section view the construction and interaction of the needle 2 and cup 4 which fits detachably within the interior of hub 6 of the syringe. Hub 6 has a female thread in the base of its interior. FIG. 1b illustrates in side elevation partial section view the construction interaction of the barrel 8, the partially closed threaded hub receiving end 10, which is located at the top of the barrel 8, and the barrel base 12 which is formed at the bottom of the barrel 8. A circular rim-like catch 14 is formed in the interior of the barrel 8 immediately above the barrel base 12 and provides a stop to deter full withdrawal of the plunger 16 from the interior of the barrel 8. Alternatively the needle may during manufacture be affixed integrally to the syringe base and be removable only during retraction into the barrel after the syringe has been used.

FIG. 1c illustrates the construction of the plunger 16, which includes a bung (piston) 18 which fits snugly against the interior of the barrel 8 and serves to force the liquid contents of the interior of the hollow barrel 8 (usually medication) out the interior of the hollow needle 2, and in a common situation into the body of a patient, when the plunger 16 is manually pushed into the interior of the barrel 8. A thumb or finger press 20 is formed at the base of the plunger 16, while the base 22 of the bung 18 serves to align the plunger 16 within the interior of the barrel 8, and deter full withdrawal of the plunger 16 from the barrel 8 by abutting catch 14. Affixed to the top central area of the bung 18 is a five tine metal hook 24.

Figure 2:
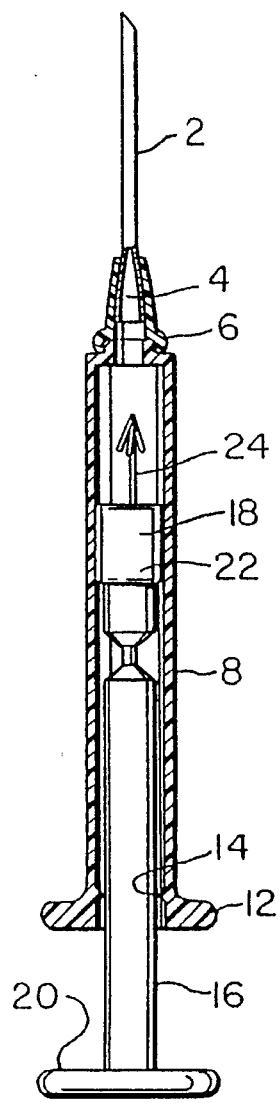
FIG. 2 illustrates a side elevation partial-section view of a first embodiment of the syringe assembly with the needle and hub secured to an end of the barrel, and the plunger and its bung and hook partially inserted into the interior of the barrel, prior to use of the syringe.
Figure 3:
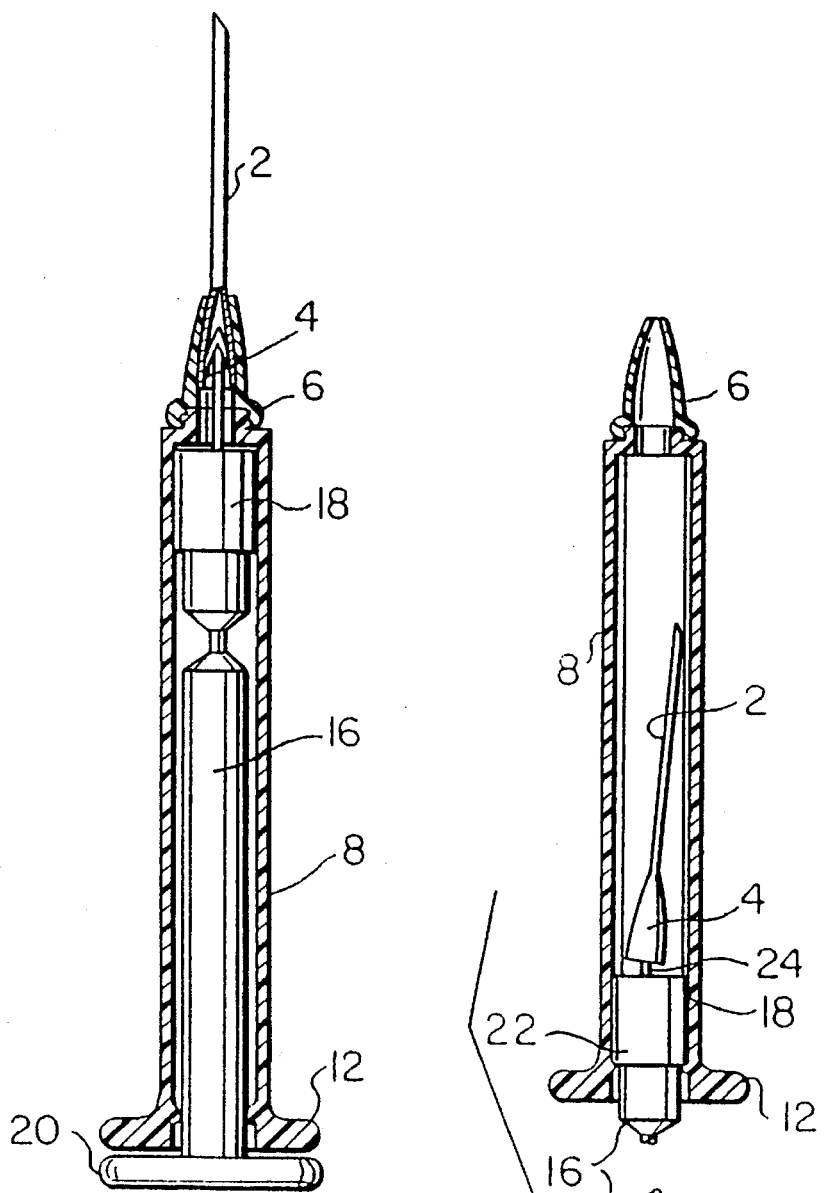
FIG. 3 illustrates a side elevation partial-section view of a first embodiment of the syringe assembly with the plunger and its bung and hook fully inserted into the interior of the barrel so that the hook extends into the interior of the hub.
Figure 4:
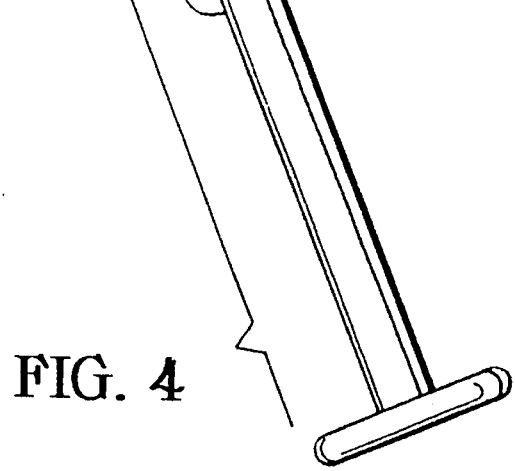
FIG. 4 illustrates a side elevation partial-section view of a first embodiment of the syringe with the plunger, bung, hook and needle fully withdrawn into the interior of the barrel and the distal end of the plunger broken-off from the bung end of the plunger.

FIGS. 2, 3 and 4 illustrate in sequential side elevation partial-section views, the syringe in assembled state, with the components in various positions. FIG. 2 illustrates the syringe assembly when it is charged with a fluid such as fluid medication, or the like, ready for use. The fluid is contained in the volume space immediately above the bung 18 and below the threaded hub receiving end 10. When the plunger 16 is fully pushed by the thumb or finger press 20 upwardly into the interior of the barrel 8, the fluid contents of the syringe are extruded by plunger 16 and bung 18 through the hollow interior of needle 2 and out the pointed end. At the same time, one or more of the tines of the hook 24 engages with the interior of cup 4 as illustrated in FIG. 3. Subsequently, as illustrated in FIG. 4, when the plunger 16 is almost fully withdrawn from the interior of barrel B, the hook 24 pulls the cup 4, and the attached needle 2, downwardly through the interior of hub 6, and into the interior of barrel 8. Thus all of the needle 2 is retracted into the interior of the barrel 8. If desired, the portion of the plunger 16 which extends beyond base 12 can be broken off at the weakened section, as illustrated in FIG. 4, and the two components disposed of in smaller pieces.

As seen in FIG. 1a, the metal of the needle is extended to form a bell shaped cup 4, which fits within the interior of and is affixed to the plastic hub 6. By using this construction, in this embodiment, the likelihood that a break will occur between the needle 2 and the cup 4 is minimized. The needle 2 and the cup 4 are formed in one piece, and since the metal is stronger than the plastic forming the hub 6, a break between the metal and the plastic is encouraged.

When the plunger 16 is fully depressed into the interior of the barrel 8, the one or more of the tines of hook 24 engage the interior of the cup 4, and then, when the plunger 16 is withdrawn, the hook 24 pulls on the interior of the cup 4 and causes it to break away from hub 6. Once a full break has been made, needle 2 and cup 4 are drawn into the interior of the barrel 8 by further withdrawing the plunger 16.

The syringe of the invention has a built-in safety feature in that the needle 2 can only be withdrawn into the interior of the barrel 8 up to the point that guide 22 abuts the catch 14 located around the interior rim of the base of the barrel 8. Thus, unless considerable effort is exerted, it is not possible to pull the needle 2, cap 4 and plunger 16 completely through the barrel 8. The catch 14 is designed so that when the components are assembled, it is easy to insert the bung 18, with the hook 24, and the guide 22 through the interior of the one-way catch 14, and into the interior of the barrel 8 but it is difficult to fully withdraw these components. Once the needle 2 is withdrawn into the barrel 8 by hook 24, it is not supported laterally and tips to one side against the barrel 8, thereby making it virtually impossible to push the needle 2 back through the hub 6. The tines of hook 24 are not necessarily of the same length, which encourages tipping of the needle 2 to one side. Breaking off the portion of the plunger 16 that extends beyond barrel base 12 ensures that the used needle 2 cannot be pushed back through hub 6, thereby exposing the sharp point of the needle 2 beyond hub 6. Also, it is usually easier to dispose of two smaller shorter components than one elongated one.

Figure 5:
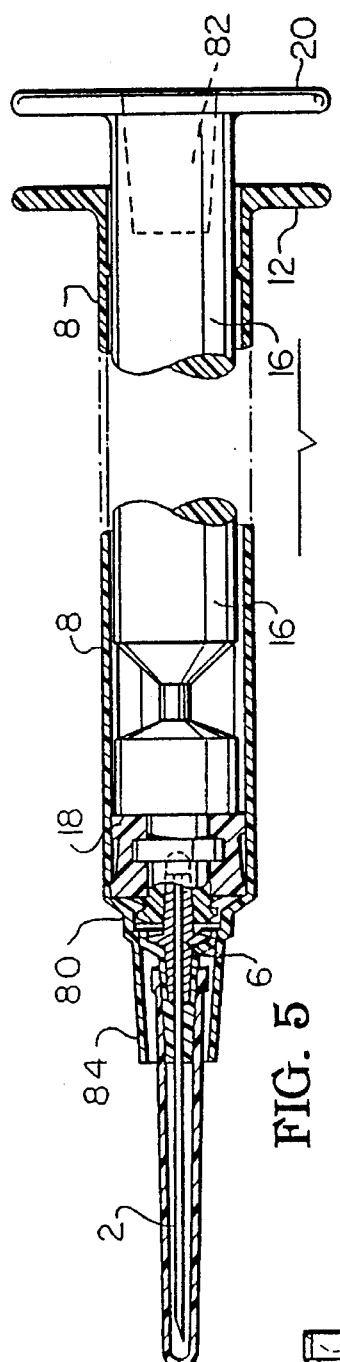
FIG. 5 illustrates a side elevation partial section view of an alternative embodiment of the syringe which has a double screw action needle and hub engagement mechanism and the end of the plunger away from the needle and hub engagement mechanism has therein a cavity which can fit over the opening in the end of the plunger after the needle and hub are withdrawn into the interior of the barrel.

FIG. 5 illustrates a side elevation partial section view of a preferred embodiment of the syringe which has a double screw action needle and hub engagement mechanism 80. The end of the plunger 16 away from the needle and hub engagement mechanism 80 has therein a cavity 82 which can fit over the cup 84 and opening in the end of the barrel 8 after the needle 2 and hub 6 are withdrawn into the interior of the barrel 8 (See FIG. 7).

Figure 6:
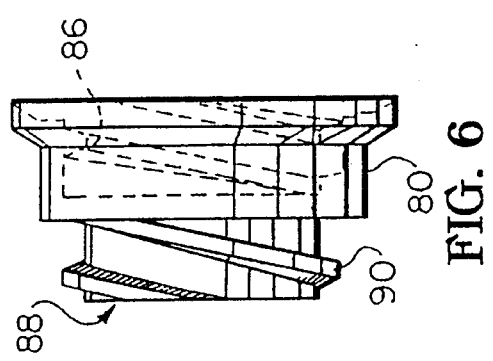
FIG. 6 illustrates a detail view of the double screw action needle and hub engagement mechanism.

FIG. 6 illustrates a detail view of the double screw action needle and hub engagement mechanism 80. The mechanism 80 is constructed so that it has right hand female threads 86 of one size diameter in a cup-like opening at one side, a right hand female thread 88 of a narrower side diameter in a cup-like opening in the opposite side, and a left-hand male thread 90 on the exterior of the mechanism 80 outside the interior female thread 88.

Hub 6 screws into female thread 88 and the syringe is used in this configuration for injecting medication into a patient. However after use, to operate the mechanism 80, to enable the needle to be withdrawn into the barrel 8, the head end of the plunger and bung 18 are screwed right handed into the female thread 86. Once fully engaged, then further right hand action on left-handed thread 90, unscrews thread 90. The entire mechanism 80 including the needle 2 can then be withdrawn into the interior of the barrel 8. The right hand and left hand threads can, of course, be reversed to operate in the reverse manner, if that is required.

Figure 7:
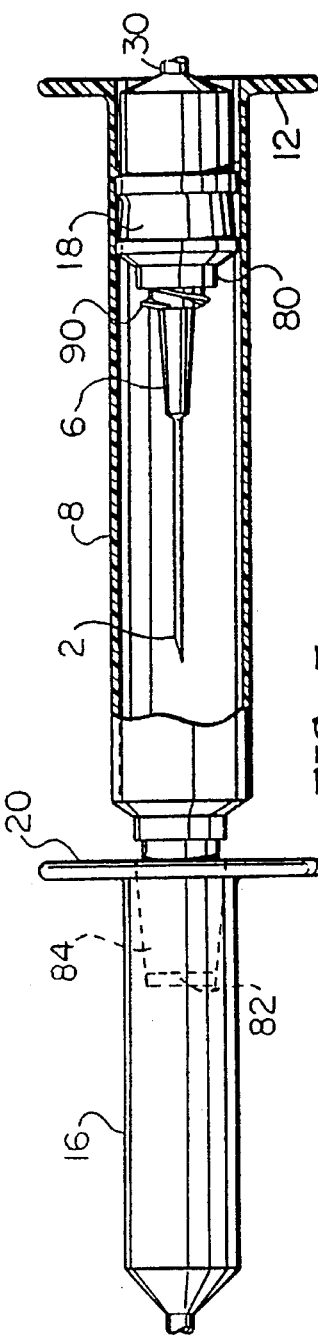
FIG. 7 illustrates a side elevation partial section view of the needle and hub withdrawn into the interior of the barrel and the broken away part of the plunger placed over the opening in the head end of the barrel.

FIG. 7 illustrates a side elevation partial section view of the needle 2 and hub 6 withdrawn into the interior of the barrel 8 and the cavity 82 of the broken away part of the plunger 16 placed over the opening and cup 84 in the head end of the barrel 8.

FIG. 8 illustrates a side elevation partial-section view of a second embodiment of the syringe which is constructed to have a screw-lock plunger-needle hub connection. As can be seen in FIG. 8, the barrel 8 has the syringe plunger 16 disposed therein. The plunger 16 carries at its frontal end (the left end as seen in FIG. 8) a piston 26 which is constructed of a resilient material such as resilient rubber so that it snugly engages the inner cylindrical surface of the barrel 8. The piston 26 is connected to the plunger 16 by means of a plunger flange 36. The frontal end of the plunger 16 is constructed to have therein a cylindrical cavity which has a female thread 28 formed in the wall of the cavity. The base of the hub 6 is constructed to have a male hub thread 34, which is formed to match and engage the female thread 28 formed in the opening in the front end of the plunger 16. FIG. 8 also illustrates piston stop 15 formed in the rear end of the interior of the barrel 8 (the right side as seen in FIG. 8). Piston stop 15 serves the same purpose as catch 14 as discussed in relation to FIGS. 1 to 4 above. A cap 32 protects the needle 2 and fits over the hub 6. Cap 32, when engaged after the needle 2 is withdrawn prevents exposure of the needle 2 if it is accidentally pushed back through the opening at the forward end of the syringe.

In use, the plunger 16 and piston 26 are disposed within barrel 8 as illustrated in FIG. 8. The cap 32 is removed and the pointed end of the needle 2 is inserted into the medication. At this time, female hub thread 34 is not engaged in male thread 28. The fluid medication is drawn into the interior of the barrel 8 by suction action created by withdrawing press 20 and plunger 16 from the interior or barrel 8, as is conventional. Once the desired quantity of medication has been drawn into the interior of the barrel 8, and air is eliminated, the sharp end of the needle 2 is inserted into an appropriate location on the patient. The medication that is held within the interior of barrel 8 is injected through the interior needle 2 into the patient by asserting thumb or finger pressure on press 20. Once the medication has been injected into the patient, the piston 26 has moved to the position illustrated in FIG. 8. It is then necessary to initiate the action which is ultimately used to withdraw the hub 6 and the needle 2 into the interior of the barrel 8. This is done by asserting a clockwise rotation on press 20, which engages male hub thread 34 in female thread 28 in the end of plunger 16 (assuming that threads 28 and 34 are right-hand threads). Hub 6 and plunger 16 are then intimately engaged by threads 34 and 28 interacting with each other. Press 20 can then be withdrawn to pull the plunger 16 from the interior of barrel 8. By this action, the hub 6 and needle 2 are pulled into the interior of barrel 8 until the rear end of piston 26 comes to rest against piston stop point 15. At this point, the plunger break point 30 has been withdrawn exterior of the barrel 8, and consequently plunger 16 can be broken into two parts at the plunger break point 30. The two parts of the syringe can then be disposed of with complete safety since the needle 2, which might have been exposed to harmful virus, or the like, has been withdrawn into the interior of barrel 8, while the part of the syringe 16 that has been broken away at break point 30, has not been exposed to any medicine and can be discarded without danger. It will be recognized that break point 30 is an option which need not necessarily be built into plunger 16. Breaking the syringe into two parts permits easy disposal whereas one elongated syringe, with the plunger withdrawn might be difficult to dispose of in certain instances.

FIG. 9 illustrates a detailed side elevation partial-section view taken along section line A—A of FIG. 11 of a first design of a piston 26 with a right-hand cam-lock rotation (rather than a thread configuration) to secure the forward end of the piston 26 to the needle hub 6 for withdrawing the needle 2 into the barrel of the syringe. The cam-lock option illustrated in FIG. 9 operates by asserting a right-hand rotation on the press 20, relative to the barrel 8. In this way, cam-lock ridge 42, which is formed in the base of hub 6, rotates into helical engagement with cam-lock groove 44. This combination replaces the male hub thread 34 and female thread 28 combination illustrated in FIG. 8, as discussed previously. Once the cam-lock ridge 42 is engaged snugly within cam-lock groove 44, the needle 2 and hub 6 can be withdrawn into the interior of the barrel 8.

FIG. 10 illustrates a detailed side elevation partial-section view of a second design of a plunger with a right-hand cam-lock rotation (similar to that illustrated in FIG. 9). However, the design shown in FIG. 10 also includes a second hub rim 38 which is formed in the base area of hub 6. The purpose of hub rim 38 is to engage left hand thread 40, which is formed in the interior of the barrel 8, which houses the hub 6. The alternative option illustrated in FIG. 10 includes the right-hand cam-lock ridge 42, cam-lock groove 44 combination, discussed in association with FIG. 9, but it has a second feature. A right-hand male hub rib 38 is formed in the exterior of hub 6 forward of cam-lock ridge 42. A matching right hand female thread 40 is formed in the interior of the forward end of barrel 8, that is, the end which surrounds hub 6. To operate the double action embodiment illustrated in FIG. 10, cam-lock ridge 42 is first engaged in cam-lock groove 44 by clockwise (right hand) rotating press 20 relative to barrel base 12 (see FIG. 8) and then, by means of a second right handed (counterclockwise) rotation, hub rim 38 is engaged within female left hand thread 40. The needle 2 and hub 6 are then double engaged by two right hand twists and can then be withdrawn into the interior of the barrel 8. The double-action engagement mechanism ensures proper secure engagement of the plunger and hub.

It should be recognized that the first and second options illustrated in FIGS. 9 and 10 respectively can be used in any of the alternative embodiments of the invention that are illustrated in FIGS. 11 through 23. It should also be recognized that the double-action locking mechanism illustrated in FIG. 10 can be right-right, left-left, right-left or left-right.

FIG. 11 illustrates an end elevation view of the needle end of the syringe illustrated in FIG. 8, and clearly illustrates the eccentric construction of right-hand cam-lock ridge 42. Ridge 42 is constructed generally in the form of an oval, the opposite ends of the oval being adapted to engage in the right-hand grooves of the cam-lock groove 44 (see FIG. 9 or 10).

FIG. 12 is a section view taken along section line B—B of FIG. 9 and illustrates the syringe barrel base 12 and the press 20 rotated clockwise 45° relative to one another. This clockwise action engages cam-lock ridge 42 in cam-lock groove 44.

Figure 13:
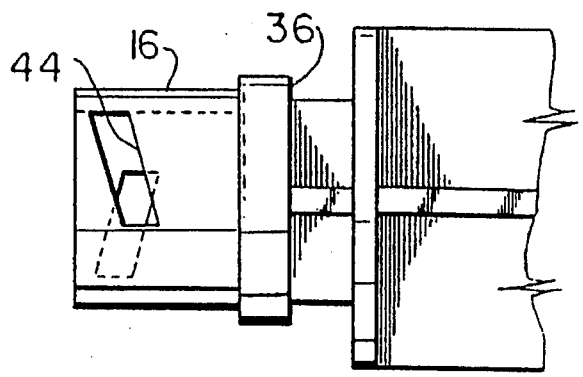
FIG. 13 illustrates a detailed side elevation partial-section view of side scoring on a plunger of a syringe with an oval flange cam lock.

FIG. 13 illustrates in detail a side elevation partial-section view of right-hand side scoring on the interior frontal opening a plunger of the syringe adapted for use with the oval flange cam-lock. As can be seen, by means of the helically angled right-hand groove 44, the right-hand oval shaped ridges 42, when they become mated in the interior of the pair of cam-lock grooves 44, rotate relative to one another in a helical fashion, thereby creating a secure fit.

FIG. 14 illustrates a detailed end view of the cam-lock mechanism of the embodiment of the syringe illustrated in FIG. 9. Barrel 8 and cam-lock ridge 42 are shown in solid lines. The dotted lines represent the cam-lock groove 44.

FIG. 15 illustrates a top elevation partial-section view of a plunger 16 which is equipped with an alternative design engaging mechanism, namely a snap-on socket type needle hub connection. FIG. 16 illustrates a side elevation view of the snap-on socket type needle hub connection illustrated in FIG. 15. As can be seen in these two illustrations, the forward end of the plunger 16 is constructed so that it has a "snap-on" fastener 46, which, when the plunger 16 is pushed strongly (in a leftwardly direction as seen in FIG. 16) snaps over and embraces the longitudinal knob-like end 48 that is formed in the base of hub 6. The snap-on fastener 46 and knob 48 engagement combination is an alternative embodiment which replaces the cam-lock ridge 42 and cam-lock groove 44 combination illustrated in FIGS. 9 through 14, as discussed previously. Unlike the thread combination 28, 34 (FIG. 8) and cam-lock combinations (FIGS. 9 to 14), no rotational action is required to engage fastener 46 and knob 48. Once snap-on fastener 46 has been pushed over snap-over knob 48, the hub 6 and needle 2 can be withdrawn into the interior of barrel 8 by pulling press 20 from the barrel 8.

FIG. 17 illustrates the snap-on fastener 46-snap over knob 48 embodiment discussed previously in relation to FIGS. 15 and 26, but includes the option a right-hand hub rim 38 and a right hand option thread 40 secondary engagement mechanism (as discussed in detail previously in association with FIG. 10).

FIG. 18 illustrates a section view of the syringe taken along section line A—A of FIG. 16. The rectangular construction of the snap-on fastener 46, which fits over snap over knob 48, can be readily seen. Also visible in FIG. 18 are the plunger flange 36 (shown in dotted lines), barrel 8, needle 2, and barrel base 12. FIGS. 15 to 18 illustrate a cylindrical embodiment. It should be understood that alternative shapes such as hexagonal or octagonal can be used. The advantage would be that such a configuration would allow for rotary movement to be transferred to the needle assembly and allow it to be broken away by rotation rather than by simple traction.

FIGS. 19 and 20 illustrate respectively side and top elevation partial-section views of a further alternative engaging mechanism, namely a bent needle hub engaging embodiment of the syringe. FIG. 19, which depicts the side elevation view, incorporates the first option (that is, without optional hub rim 38, and right hand thread 40 combination). FIG. 19 shows how the base end of the needle 2 is bent at right angles to form an upwardly projecting end 50. The end 50 fits into a slot and groove 52, which is formed in the forward end of the plunger 16. By rotating the plunger 16, and piston 26 about 90° relative to end 50, the end 50 engages in slot 52, thereby securely connecting the head end of plunger 16 with hub 6 and needle 2. This engagement allows the hub 6 and needle 2 to be withdrawn into the interior of the barrel 8, as described previously. FIG. 21 illustrates the bent needle embodiment that was discussed above in relation to FIGS. 19 and 20, but including the option of a hub rim 38, and right hand thread 40, formed in the hub 6 to provide a double engagement mechanism. As mentioned previously, either option 1 or option 2 (FIG. 9 or 10), can be utilized in all embodiments of the syringe as discussed.

FIGS. 22 and 23 illustrate a detailed end view of slot 52 and needle end 50, the slot 52 being formed in the head end of the plunger 16. The bent needle end 50 is first inserted in slot 52, as illustrated in FIG. 22, and then the end 50 is rotated 90° into a groove opening formed in the interior of the plunger 16, thereby engaging the base end of the needle 2 with the plunger 16.

FIG. 24 illustrates a side-elevation partial-section view of an embodiment of the syringe wherein the needle and hub are rotatably detachable from the barrel and the plunger threadedly engages the interior of the hub. The base of the needle 2 is threadedly and removably engageable with the hub 63 by threads 62. In turn the hub 63 is threadedly and removably engageable with the barrel 8 by thread 64. The head end of the plunger 16 can engage with the interior of the hub 63 by interior threads 65 and withdraw needle 2 and hub 63 into the interior of the barrel 8. The interior of the head end of barrel 8 is shaped like an "M". The angled ends deter the needle 2 from pushing back through the opening in the end of the barrel 8.

FIG. 25a illustrates a side elevation partial-section view of the syringe with the needle and hub drawn within the interior of the barrel and the remote end of the plunger that is broken away, formed with a hollow threaded cap-like opening and FIG. 25b illustrates a side-elevation partial-section view of the syringe With the broken away plunger portion threadedly engaged with the male threaded end of the hub at the top of the barrel.

As shown in FIG. 25a, the hub 6 can be formed so that it has male threads 70 around its circumference. Correspondingly, a mating cavity with mating female thread 72 can be formed in the thumb press end of plunger 16. If need be, the thumb press end of plunger 16 can be widened at location 74 in order to accommodate the cavity with the female thread 72.

With this embodiment, when the plunger 16 is broken away at break point 30, it can be used to cover the open end of syringe 8 by screwing female threads 72 onto male threads 70 of hub 6. In this way, both ends of the barrel 8 are closed, and there is no way that the potentially contaminated needle 2 can escape the interior of barrel 8.

Alternatively, once the plunger has been broken, the end distant from the thumb press and proximate to the fracture site can be fashioned to allow it to fit snugly or screw into the now open end of the barrel (from which the needle has now been withdrawn into the barrel). If required, a second fracture site (not shown) can be fashioned in the plunger. This permits the plunger to be broken off at either of the two fracture sites according to the performance of the user.

FIGS. 25c and 25d illustrate sequential side elevation views of an alternative design of syringe where the part of the plunger 16 adjacent the breakaway weak point 30 is threaded 78 and is screwed into female threads 76 of the opening in the end of the barrel 8 vacated by the needle 2 and hub when pulled into the barrel 8.

FIG. 26, illustrates a side elevation partial-section view of an embodiment of the syringe wherein the piston is adapted with a latch which snaps into place in an adapter (platform) after the piston is fully depressed and rotated clockwise. The embodiment illustrated in FIG. 26 depicts the needle 2 embedded in a Luer lock 100, associated with the constricted end 10 of syringe barrel B. The plunger 16 with a finger press 20 at the remote end thereof is positioned inside barrel 8. A stop clutch 14 prevents the plunger 16 from being totally withdrawn from the interior of the barrel 8. Bung 18, which provides a tight fit with the interior of barrel 8, is mounted on the end of plunger 16 opposite finger press 20.

The operative needle engagement and detachment mechanism illustrated in FIG. 26 is a combination of an adapter 102, which cooperates with Luer lock 100, the combination fitting into the narrow end 10 of barrel 8. The end of plunger 16 opposite finger press 20 has a latch mechanism 104 formed inside bung 18. A pair of prongs 106 are formed in latch 104 and engage into grooves 108 in adapter 102 when the plunger 16 is rotated in a clockwise direction. Once the pair of prongs 106 engage in the respective grooves 108 of the adapter 102, then the plunger 16 is rotated further clockwise which then, because of the left hand threads 110 engaging the interior of the narrow end 10, causes the adapter, and the needle with the Luer lock 100, to disengage from the narrow end 10. At this point, the needle 2, Luer lock 100, adapter 102, and bung 18 can be withdrawn into the interior of the barrel 8 by pulling finger press 20 away from the narrow end 10 of the syringe.

As can be recognized, the adapter 102 is an important feature of this embodiment of the invention. The adapter enables a standard Luer lock 100 to indirectly mate with latch 104 at the end of plunger 16. Moreover, the adapter 110 is designed so that it accommodates different sides of needle 2 and Luer lock 100.

FIG. 26 illustrates a narrow point in the plunger which assists in breaking the plunger in two. If required, or desirable, two or more additional narrow points can be included to permit breakage at alternative locations.

FIG. 27 illustrates in side elevation partial section view a preferred embodiment of the adapter 102. Nose 112 is adapted to fit inside the hollow of a standard Luer lock 100. The left hand thread 110 is also shown in FIG. 27. The adapter 102 has opposite the nose 112 a cup-like edge 114 which is formed to receive the front end of latch 104. Formed inside the rim of cup 114 is a protrusion 116 which has a pair of fast acting spiral male threads 118 formed thereon. Prong engaging grooves 108 are also formed in the interior of the protrusion 116 at the point where the protrusion 116 joins with the cup 114. The advantage of this adapter design is that with the fast acting spiral threads 118 force alignment without jamming. Full axial movement is possible with no rotation forced by the alignment threads. Then after full depression of the plunger, rotation will disengage the adapter 102 and allow the prongs 106 to engage in grooves 108. Rapid engagement between the prongs 106 in grooves 108 is achieved by minimal rotation of the plunger 16. At that point, further clockwise rotation of the plunger 16 by means of finger press 20 causes the threads 110 of adapter 102 to disengage from the interior narrow end 10. The needle 2 assembly can then be withdrawn into the interior of barrel 8.

FIG. 28 illustrates a section view taken along section lines C—C of FIG. 29. FIG. 28 depicts a detailed view of the construction of the latch 104 and prongs 106. In the embodiment illustrated in FIG. 28, the latch 104 has a pair of alignment ridges 120 formed in the interior of latch 104. These alignment ridges 120 assist engagement of the latch 104 with adapter 102.

FIG. 30, which illustrates a side view of an alternative design of adapter 102, and FIG. 31, which illustrates a partial cut-away section view of the adapter depicted in FIG. 30, illustrate flared grooves 122, which are adapted to receive ridges 120 of latch 104. The flare assists in enabling the ridges 120 to be received into grooves 122. In this embodiment, the adapter does not have the fast acting non-jamming spiral threads 118, depicted in the adapter design illustrated in FIG. 27.

The adapter 102 has a rim 124 which is designed to engage with the rim 126 of the Luer lock 100 to hold the two snugly together.

The embodiments of the invention depicted in FIGS. 26 to 31 have a number of advantages:

1. The preferred embodiment allows for universal coupling with all Luer lock needle connections.
2. Needle interchangeability during use of the syringe is possible, that is, different needles can be used for filling the vial and for injecting the patient.
3. The needle platform (adapter) design allows for compatibility of the syringe with other custom design needles or any subsequent needle design, merely by altering the outer needle connection configuration platform.
4. The syringe hub can be permanently closed after use of the syringe by screwing on the broken plunger stalk after withdrawal of the needle into the barrel.
5. The novel coupling mechanism between the platform and the plunger allows full axial movement of the plunger without the possibility of an inadvertent locking. But deliberate rotational action permits locking of the coupling device and withdrawal of the platform (adapter) with the attached needle in the barrel.

FIG. 32 illustrates a side elevation partial side section view of an embodiment of the invention related to that illustrated in FIGS. 26 to 30. The embodiment depicted in FIG. 32 shows an adapter 130 which extends partially from the front end of the barrel 132. A standard Luer lock 134 is formed in the front end of the barrel 132. The Luer lock has a standard right hand thread 135. The barrel 132 has a left hand thread 137 to release the adapter 130 for withdrawal inside the barrel 132, after the syringe is used. A needle hub 136 carrying needle 140 fits on the tapered front end of adapter 130 and screws into the right hand thread of the Luer lock 134. A given clearance 138 permits the needle hub 136 to be withdrawn into the interior of the barrel 132 after the adapter 130, hub 136, and needle 140 are unscrewed and withdrawn into the barrel 132 by rotation of the plunger and engagement of the plunger adapter connection mechanism. As described previously, a Luer tip may be a simple conical device which accepts the needle base. This design could also be used in this embodiment, thus eliminating the screw connection of the needle hub 136 and the Luer lock thread 135.

One advantage of the syringe design depicted in FIG. 32 is that the adapter 130, allows for longer needles to be accommodated. Another advantage is that by reducing the minimum diameter of the platform needle combination, a thinner barrel can be manufactured. For a given capacity of syringe, this will allow the length of the syringe to be longer and therefore a longer needle to be accommodated within it. By placing the Luer lock threads in the barrel of the syringe rather than on the platform, the outer diameter of the platform needle combination is defined by the width of the needle hub and not by the supporting outer plastic Luer lock mechanism. It is therefore possible to ensure as long a barrel as possible for a given capacity. The standard 3 cc syringe represents a main portion of the syringe market. A standard 3 cc syringe is often used with a 1½ inch needle for intramuscular injection. Accordingly, the barrel of a 3 cc syringe should be at least 2½ inches long to accommodate the withdrawn needle, adapter and plunger connector all within the barrel. This is done by the design as shown in FIG. 32.

The foregoing embodiments discuss various means of enabling the plunger to be connected securely to the hub 100 of the needle 2 in FIG. 26, for example, to enable the plunger 16, when withdrawn, to pull the hub 6 and needle 2 into the interior of the barrel 8. In some versions including the adapter, the adapter disengages if it (the plunger connector) is twisted in the wrong direction. This provides an over tightening safety feature. The adapter is released from the syringe if the correct rotation is used. It will be recognized that these are illustrative of specific embodiments and there are other possible ways to make a secure connection for the purpose of withdrawing the hub and needle into the interior of the barrel.

FIG. 33 shows a perspective view partially in phantom of another embodiment of a safety syringe which includes a plunger 154 within a barrel 152. The syringe additionally includes a needle hub 156 carrying a needle 155 which may be covered by a needle guard 151 that is affixed to the barrel by way of barrel threads 153 and the complementary threads of the guard.

As more clearly seen in the side elevation partial sectional view in FIG. 34, the plunger includes a circular cylindrical portion 154a having a threaded end portion 154b, a finger press plate 154c and an outer annular ridge 154d for providing a sealing engagement with groove 152a of barrel 152. The plunger additionally includes portion 154e for engaging the needle adapter 150 as well as the plunger bung 157.

The plunger 154 additionally includes a narrowed portion 154f including a weakened break point 154g, as well as a pair of resilient arms or prongs 154h. The details of these elements will become more apparent from a review of the expanded detailed drawings of FIGS. 41 and 42, for example.

Returning to the syringe as illustrated in FIG. 34, it will be noted that once sterilized and assembled as illustrated with the needle guard in place forming a sealing engagement with the threaded barrel, as well as with the plunger in the position shown forming a sealing engagement between elements 152a and 154d, the interior of the structure is sealed at both ends, thus maintaining sterile conditions. As to forming and maintaining the above noted seals, it will be recognized that other forms of seals may be used. For example, although the exemplary embodiment illustrated in FIG. 34 includes a threaded connection between the needle guard and the end of the barrel, other forms of sealing arrangements involving friction fits or the use of annular ridges and complementary grooves, as well as other sealing connections as illustrated in previous embodiments, may also be used. In this the regard, however, it will be noted that the threads 153 of the barrel are not only designed to accommodate a threaded connection with needle guard 151, but are also sized and designed to accommodate a threaded connection with complementary threads 154b of the hollow plunger portion 154a once this plunger portion is broken away and connected to the end of the barrel, as illustrated in FIGS. 38 and 39. Accordingly, any change in the connection elements of 151 and 152, as previously suggested, would require a corresponding change in the manner of connecting elements 152 and 154a.

Again returning to the embodiment as illustrated in FIG. 34, considered along with the enlarged element details illustrated in FIG. 40, it is evident that adapter 150 is connectable to plunger portion 154e by way of complementary surfaces 150a and 154i, as well as surfaces 150d and 154k. As may be seen from a consideration of FIG. 40, all of these surfaces engage when the plunger is fully inserted and due to the slopes of the surfaces produces only a unidirectional torque on the adapter when the plunger is rotated in the proper direction. Plunger rotation in the opposite direction causes surfaces 150d and 154k to separate and the plunger to be partially withdrawn. In operation withdrawal of the plunger and the attached bung 157 away from the adapter 150 is accomplished with relative ease since the adapter is securely attached to the barrel 152 by way of complementary threads 150b and 152b, as may be seen from a consideration of FIGS. 35 and 37. Adding to the ease of separation of the adapter and plunger-bung is the relatively large slope of the thread surfaces 150a and 154i which offer little or no resistance to separation. Moreover, although the resilient ridge 154j and groove 150c (FIG. 40) offer some resistance to separation, the combination does not prevent such separation or require more than a reasonable force to "unsnap" the connection when the adapter is affixed to the barrel. Ridge 154j may be partially or wholly annular as one manner of decreasing or increasing resistance to separation.

After use and with the adapter and plunger connected as illustrated in FIG. 34, the plunger may be rotated in the manner shown in FIG. 36 so as to disconnect the adapter from the interior threads at the distal end of the barrel by operation of the flat axial surfaces 150d and 154k. An important feature of this engagement mechanism is that once the adapter has been disconnected at its threaded connection with the barrel, it along with the remainder of the needle assembly remain attached to the plunger portion 154e through the snap connection formed by ridge 154j and groove 150c. Thereafter, the plunger and attached needle assembly may be withdrawn into the barrel in the manner illustrated in FIG. 37.

Clearly, retraction of the contaminated needle into the barrel prevents or substantially reduces the possibility of inadvertent needle stick injuries. Furthermore, as may be appreciated from a consideration of the connection illustrated in FIG. 40, it is another important feature of the engagement mechanism that once the adapter 150 has been disconnected from the distal end of the barrel 152, in the absence of extraordinary measures or the use of a special tool, the needle assembly and the adapter cannot be reassembled to the barrel and be reused. Thus, attempts to reattach the adapter to the barrel for subsequent use, illicit or otherwise, is effectively prevented since the spiral grooves and faces of the adapter-plunger connection are shaped in such a manner as to prevent adequate transfer of torque in the proper direction to attain reattachment of the adapter to the barrel by merely rotating the plunger in the direction opposite that illustrated in FIG. 36.

In use, the exemplary embodiment of syringes as illustrated in FIGS. 33 through 42 are bulk packaged, sterilized, assembled structures of the nature generally illustrated in FIG. 34. Initially, the needle guard 151 is removed, the plunger and attached bung are withdrawn, and the proper dosage of fluid within the syringe body is adjusted using calibration markings (not shown) on the barrel in combination with the straight radial forward edge of the bung 157 to obtain a rapid and highly accurate measured reading of the contents. In this regard it must be noted that on conventional syringes the calibration markings, as well as the bung are usually black, with the bung attached to a slightly opaque plunger that is normally of an X cross-section. Additionally, the leading edge of the bung is normally curved outwardly. Accordingly, neither rapid nor accurate readings are obtainable with such structure which includes two interfaces between the bung and the fluid contents and between the bung and the plunger. Such readings are additionally complicated by attempting to distinguish black calibration markings against a black bung.

As previously noted, the forward surface of the bung 157 albeit annular is straight in the radial direction. Moreover, the coloration of the bung and plunger elements are the same so as to obtain a single interface. Moreover, the colors of the materials, as well as the calibration markings, are selected to be contrasting so as to significantly improve the accuracy as well as the speed with which measurements may be taken. As an additional important feature pertaining to rapid and accurate measurements, the cylindrical plunger portion 154a is sized to be closely received in barrel 152, thus reducing diffraction and increasing visibility.

Presuming that the syringe has been used to inject fluid, the plunger is rotated in the manner shown in FIG. 36 and the plunger as well as the needle assembly including adapter 150 are withdrawn to the position illustrated in FIG. 37 where the ends of the resilient arms 154h register with annular groove 152a so as to retain the needle assembly and lower portion of the plunger in the position illustrated. Thereafter, cylindrical plunger portion 154a may be broken away at the plunger break point 154g in the manner illustrated in FIG. 38. Regarding the narrowed portion of the plunger 154f, it is to be noted that although illustrated as being circular in cross section in FIG. 41, it may also take other shapes such as oval in order to enhance the ease with which portion 154a may be broken away.

After portion 154a has been broken away, it may be attached to the threaded distal end of the barrel in the manner illustrated in FIG. 39.

Thus, subsequent to the intended use the needle assembly has been withdrawn into the barrel and locked in position by way of locking arm 154h, for example. Moreover, the bung and the raised edge of plunger portion 154e would serve to seal one end of the barrel, whereas portion 154a of the plunger may be attached to the threaded end of the barrel 152 by way of the illustrated threaded connection or by other well known snap-fit or friction-fit connections, for example. As illustrated in FIG. 39, not only is the needle withdrawn to a position eliminating inadvertent needle sticks, but the barrel is sealed at both ends thus effectively preventing the escape of any toxic or contagious contents a feature not seen in the known prior art.

As illustrated in FIGS. 33–39, the cylindrical plunger portion 154a constitutes a hollow cylindrical sleeve closed at its inner end by the narrowed portion 154f and open at its outer end terminating in the threads 154b. As a consequence, when the plunger portion 154a is disposed on the distal end of the barrel sealing the latter, the interior of portion 154a serves as a reservoir or receptacle open at its proximal end to the barrel of the syringe. Thus, in the unlikely event that the needle is not withdrawn the full distance, as illustrated in FIGS. 37–39, or should the adapter and needle be pushed axially inwardly along the barrel when the syringe is being handled or otherwise disposed, e.g., by other disposables bearing on the exposed end of the portion of the plunger left in the barrel, there is no danger that the needle can be pushed through the barrel or plunger or is otherwise exposed.

As will be appreciated by the artisan, the selection of materials, coloring, shapes, as well as the location and nature of the seals, used in the embodiment of FIG. 34, for example, may also find use in other disclosed embodiments. Moreover, it will also be appreciated by the artisan viewing the details of the embodiment of FIG. 34, for example, that since plunger element 154a is hollow and is made sufficiently long as to encapsulate the needle assembly in the position illustrated in FIG. 34, for example, should the adapter 150 malfunction and fail to separate from the barrel, the exposed needle assembly may nevertheless be covered by either needle guard 151 or by plunger portion 154a. In this regard it is to be noted that since the needle guard, as well as the hollow plunger portion, have been made of approximately the same diameter as the threaded end of the barrel, both the needle guard and the plunger portion 154a may more safely be installed on the exposed needle in comparison with needle guards of smaller diameter such as is found in the embodiment of FIG. 32. Accordingly, it will be seen that the design of the embodiment found in FIGS. 33 through 42 includes redundancy features whereby even if the needle assembly fails to disengage and retract after use, it may nevertheless be covered in at least two other ways as discussed above, thus incorporating additional safety features.

A still further embodiment, which is the presently preferred embodiment, is illustrated in FIGS. 43 through 47. This exemplary embodiment is similar in many respects to the previously recited embodiment as may be appreciated from a comparison of FIGS. 34 and 43. That is to say, barrel 162 of FIG. 43 is substantially identical to barrel 152 of the previous embodiment except for the elimination of the seal-locking arrangement formed by members such as 152a and 154d and the inclusion of elements 162a which, as illustrated in greater detail in FIG. 47, include two annular ridges and an intervening groove on the inside surface at the finger press end of the barrel. As will be seen in FIG. 47, the means 162a of the barrel are designed to cooperate with annular ridge 164d included in plunger portion 164a. As will be recognized by the artisan, the parts can be reversed. That is to say, elements 162a can be included on the plunger and element 164d can be included on the barrel. These elements cooperate when engaged to form an effective seal at one end of the barrel so as to prevent ingress or egress of materials to the central portion of the syringe body until it is used. This seal along with the use of a needle guard of the nature illustrated with the embodiment of FIG. 34, which may be affixed to the barrel 162 by way of threads 163, will completely seal both ends of the syringe body. Such sealing, as with the previous embodiment, will allow the syringe to be sterilized and then bulk packaged rather than individually packaged, but nevertheless retain internal sterility. Clearly, this feature will result in beneficial results such as reduced labor and material costs.

Returning to a consideration of FIG. 43, it may be seen that barrel 162 includes an annular groove formed at 162b which cooperates with the annular sealing ridge 160a included in adapter 160. This groove can be formed in the barrel during the manufacturing process or, preferably, is formed by the ridge 160a during assembly due to the resilience of the plastic barrel material. This sealing feature may be seen in greater detail in FIG. 46, wherein the sealing between the adapter and the barrel is clearly enhanced. The embodiment of FIG. 43 additionally includes modifications to plunger portion 164e which is substantially different than that of portion 154a illustrated in FIG. 34. This plunger portion which is shown in greater detail in both FIGS. 44 and 45 includes an outer circumferential lip 164h which is sufficiently reduced in diameter as to snap past barrel ridges 162a on assembly, but will be retained at the innermost ridge when the plunger and needle assembly are withdrawn into the barrel. Such withdrawal occurs in the same manner as was explained with regard to the embodiment of FIG. 34. That is to say the coupling means between the adapter 160 and the plunger portion 164 are of the same nature illustrated in FIG. 40, and the adapter is uncoupled from the barrel and withdrawn into it in the same manner as was previously explained with regard to the embodiment of FIG. 34, except that means 162a are used to retain element 164e in the withdrawn position.

Subsequent to withdrawing the plunger and needle assembly into the barrel, cylindrical plunger portion 164a may be broken away at the reduced break point or notch 164g of portion 164f. As with the previous embodiment, narrow portion 164f may be circular in cross section or have other shapes such as oval for aiding in breaking away plunger portion 164a.

After the plunger portion 164a has been removed, it may be joined to the distal threaded end of barrel 162 as in the previously described embodiment. As will be appreciated by the artisan, element 164 is designed to be attached to the distal barrel end, even if the adapter fails to disengage from the barrel and the needle fails to retract. Moreover, as with the embodiment of FIG. 34, those skilled in the art will recognize that threaded connections such as formed at 163 and 164b may be replaced with other connection means such as snap connections or friction fits of the nature previously described.

Additionally, as with the previously described embodiment, the bung 157 as well as the plunger portions may have similar coloration which additionally contrasts with the coloration of the calibration markings (not shown) on the barrel. Such coloration, as well as the radially linear forward surface 167a as detailed in FIG. 46, present a single fluid plunger interface with greatly enhanced visibility as well as accuracy for the reasons previously described.

Additionally, as with the previously described embodiment, due to the design of the adapter and plunger portion 164e and the connection between them, the plunger may be fully compressed without permanent attachment between the elements. That is to say, elements 164j, which may be resilient prongs or a resilient annular ridge, maintain the connection while engaged in groove 160c. As with the connection as shown in FIG. 40, the adapter when disconnected from the barrel is retained by the plunger portion 164e when withdrawn into the barrel. However, elements 164j will release the engagement with the adapter when the plunger is withdrawn without rotation, since the adapter and barrel remain engaged.

As previously indicated, the artisan will appreciate that the beneficial features of this embodiment, such as the coloration, sealing and locking arrangements, among others, may be adapted for use in still other embodiments previously disclosed. For example, the embodiment of FIG. 32 can obviously be modified to accommodate a full size needle guard connected to the exterior of the barrel and may be further modified to include a sealing arrangement of the nature illustrated in either FIG. 34 or FIG. 43 at the finger press end. Such modifications would result in preventing the entrance of contaminating materials within the syringe body. Furthermore, the plunger portion containing the threaded connection as illustrated in FIG. 32 can obviously be modified to be of a hollow circular cylindrical form so as to be usable at the distal end of the syringe barrel whether or not the needle assembly has been retracted into the barrel.

A further modification to the embodiment of FIG. 43 may be found in the further exemplary embodiment illustrated in FIGS. 48 through 50. This embodiment is similar in most respects to the embodiment of FIG. 43 except that the narrowed intermediate portion of the plunger (164f and 174f of the respective embodiments) includes as a substitute for the break point (164g) a connection means whereby the hollow cylindrical portion of the plunger may be unlatched or disconnected from the needle end portion and subsequently re-attached thereto. Such construction allows the hollow finger press portion of the plunger 174a to be used as a needle guard both before and after use, as well as a plunger portion during use.

As may be seen from a consideration of FIG. 43 and 48, the needle end plunger portions (164e and 174e, respectively) are substantially the same except that the narrowed intermediate portion 164f with break point 164g has been replaced with a rectilinear locking mechanism 174f having a rectangular shaped socket 174f with two resilient wings or side arms 174m that are slightly flared in the outward or radial direction.

The upper ends of these two arms include lips 174n which are arcuate and which have an internal groove 174o which is also arcuate.

The plunger portion 174a as in the embodiment of FIG. 43 is a hollow cylindrical cylinder in cross section. However, the needle end portion thereof has been modified as illustrated in FIGS. 48 and 49 to include a rectilinear portion 174k which is complementary to the rectilinear portion 174f. Accordingly, when these portions are joined, both portions 174a and 174e will rotate as a unit. Moreover, since the adapter/plunger engagement structure in this embodiment is the same as that found in the embodiment of FIG. 43, for example, unidirectional rotation of the adapter will be obtained in the previously described manner when the plunger is rotated.

As will be further noted from a comparison of FIGS. 43 and 49, for example, the same type of sealing at the finger press end of the syringe comprising complementary ridge arrangements are included in the embodiment of FIGS. 48 through 50. It will be noted, however, that the finger press end of the barrel 172 has been tapered so as to allow the arms 174m to flare outwardly and unlock or disengage from the complementary grooves included in plunger portion 174a.

In operation the sterilized syringe is supplied with cylindrical portion 174a connected over the needle and in sealing engagement with the distal end of the barrel 172. In this regard, although the sealing engagement is illustrated as a threaded connection, other connection means as previously described may be used. As supplied, the syringe would also include the adapter and needle assembly connected to the distal end of the barrel but with the plunger portions 174e and 174f along with bung 17 withdrawn into the barrel and in sealing engagement with the finger press end of the barrel in the same manner noted with regard to the embodiment of FIG. 43. Additionally, arms 174m would be positioned as illustrated in FIG. 49. Accordingly, as supplied, both ends of the syringe would be sealed, thus maintaining sterility as to the enclosed portions of the syringe body. Additionally, once the syringe is used the needle end portion of the plunger along with the adapter and needle assembly may be withdrawn and plunger portion 174a disconnected, as illustrated in FIG. 49. Thereafter, the disconnected plunger portion 174a may be reconnected as before to the distal needle end portion of the barrel so that both ends of the syringe are again sealed whereby toxic or contagious material within the syringe body cannot escape. Moreover, as with the embodiment illustrated in FIG. 43, plunger portion 174a may be re-attached to the barrel as a needle guard whether or not the needle assembly has been withdrawn into the barrel.

Clearly the modification illustrated in FIGS. 48 through 50 offers the advantage whereby a single element (174a) may be used both as a needle guard and as a portion of the plunger through the use of the disclosed rectilinear locking mechanism. Moreover, the previously described sealing and locking arrangements and their beneficial results may be maintained. Additionally, the previously described beneficial results to be obtained by the shape and coloration of the elements whereby visibility and accuracy of measurement of the syringe fluid contents may also be applied to the embodiment of FIGS. 48 through 50. Furthermore, the artisan will appreciate that the beneficial feature of this embodiment may be adapted for use in still other embodiments previously disclosed.

As will be recalled, a further feature of the present invention provides for a venting structure in the adapter for venting air from the interior of the barrel once the barrel has been substantially filled with fluid to be injected and prior to injection. It will be appreciated that in those embodiments hereof where the hub or adapter has structure which protrudes into the barrel from the distal end of the barrel, there is formed an annular space between such protrusion and the barrel. With the central passage through the adapter and needle terminating inwardly of the distal end of the barrel, there is the danger of entrapment of air within the annular space between the protrusion and the barrel adjacent the distal end of the barrel. The following is a description of a specific embodiment of the present invention which eliminates any such air and vents the entirety of the air in the barrel prior to injection. The concept and structure of this embodiment are applicable to the previous embodiments, for example, to the hub 6 of the embodiments of FIGS. 5, 8, 10, 15 and 17, the adapter 102 of the embodiments of FIGS. 26–32 and the adapter 150 of the embodiments of FIGS. 33–42, and the adapter 160 of the embodiment of FIG. 43.

Turning now to FIG. 51, there is illustrated an adapter 200 substantially identical to the adapter illustrated in FIG. 40, with the further improvement of the vent openings, as will now be described. Adapter 200, of course, has a central axial passageway 202 defined in part by the protrusion 204 of the adapter into the barrel and on which protrusion is mounted the spiral threads or surfaces 206, terminating in the annular groove 208, all as previously described. Adapter 200 is threaded into the end of the barrel, as illustrated in FIG. 52, similarly as the embodiment of FIG. 40.

In this form, however, there is provided at least one and preferably a pair of vent passages 210 extending radially from and in communication with the central axial passageway 202. These passages preferably extend in grooved portions 212 formed in the face of the flange facing the proximal end of the barrel. Additionally, that face is tapered radially inwardly in a direction toward the needle end of the barrel, for example, on the order of about 3°. Further, an annular trough or groove 211 is preferably formed in the tapered flange face about the base of protrusion 204. Groove 211 lies in communication with grooved portions 212 and vent passages 210. One or more additional annular grooves may also be provided including about the outer margin of the tapered flange base or at intermediate radial positions. By grooving the passageway portions 210 and groove(s) 211 in the face of the adapter 200 and tapering that face, the grooves 211, 212 and passage portions 210 will assume the most superior position within the interior of the barrel when the syringe is oriented vertically with the needle uppermost. Consequently, when the plunger is advanced toward the needle end to vent air from the interior of the barrel, any air trapped within the annular space 214 between the distal end of the barrel and protrusion 204 will vent through the grooves and openings into the central passageway. Hence, the interior of the barrel may be purged of any air prior to injection. It will be appreciated that there may be only a single vent passage 210, although preferably at least two such passages diametrically opposed to one another are provided. More than two such passages may also be provided, preferably equally spaced about the axis of the adapter.

Referring now to the embodiment of FIG. 53, the central passageway 202a terminates short of the distal end of the protrusion 204a. Consequently, the central passage 202a communicates only with the one or more radially extending passages 210a and grooves 211a, 212a. In this form, not only do the passageway portions 210a and grooves 211a, 212a form the superior positions when the syringe is oriented vertically with the needle uppermost to enable venting air from the barrel and particularly the annular space 214a between the barrel and protrusion 204a, but provide the sole passageway portions for egress of fluid from the interior of the barrel through the central passageway 202a during injection. The opening 216 in the end of protrusion 204a is in the form of a multi-sided opening, e.g., a hex-shaped opening, for purposes of receiving a tool for assembling the syringe. Thus, a tool may be inserted through the opposite end of the barrel and received in opening 216 to thread the adapter onto the barrel.

Referring now to the embodiments of the invention illustrated in FIGS. 54–56, three forms of syringes having tamperproof features are disclosed, respectively. In FIG. 54, there is illustrated a syringe having a barrel 300, a finger press 302 for the plunger, and a needle guard 304. The needle guard is, of course, screw-threaded or otherwise secured to the end of the barrel 300, for example, as illustrated in FIGS. 33 and 34. In this form of the invention, a strip 306 of paper or other material, such as plastic, having adhesive along one side thereof is applied along a side of the syringe. Particularly, the strip is applied along the side of the barrel 300 and onto the end of the needle guard 304 at its juncture with the barrel 300. The opposite end of the strip 306 is applied to the finger press 302 and preferably extends across the top of the finger press and partially down the opposite side to at least the cylindrical barrel portion. In this manner, the juncture between the finger press 302 and barrel is spanned by at least a portion of the strip 306. As a result, it will be appreciated that any inadvertent or attempted removal of the needle guard from the barrel or rotational or axial movement of the finger press 302 relative to the barrel will cause the strip 306 to tear or become twisted whereby the disruption of the seal at these junctures and possible tampering with the syringe will be indicated.

In FIG. 55, another form of tamperproof syringe is disclosed. In the embodiment illustrated in FIG. 55, the barrel, finger press and needle guard are indicated as in FIG. 54 with the suffix "a" applied thereto. In this form, thin-film plastic material 308 and 310, respectively, is applied, for example, by heat-shrinking, about each of the junctures between the needle guard 304a and barrel 300a on the one hand and the barrel 300a and finger press and plunger portion 302a, on the other hand. Once again, any rotary movement or other movement of the needle guard 304a relative to barrel 300a or rotary or axial movement of the finger press 302a relative to barrel 300a will be detected by the severing of the shrink-wrapped plastic material or its wrinkling whereby disruption of the seals at the opposite ends of the syringe or tampering with the syringe will be indicated. It will also be appreciated that the shrink-wrap of plastic material assists in maintaining the sterility of the syringe and that suitable tear strips may be provided along each of the shrink-wrapped portions to facilitate their removal and use of the syringe.

In FIG. 56, the like elements of the syringe are illustrated by like reference numerals as in FIGS. 54 and 55, followed by the suffix "b". In this form, the syringe is dipped into a melted plastic material whereby a thin-film coating of plastic 312 is applied about and completely envelops the syringe with the needle guard attached and plunger located in its axially innermost position. For example, the plastic coat 312 may comprise a clear chlorinated polyvinyl chloride coating (CPCV). The ingredients are vinyl chloride-vinyl acetate resin silicon dioxide (amorphus) with a methol isobutyl ketone base. This is an air dry coating. The drying can be accelerated by raising the temperature to 100° F. The melting temperature of the plastic material is, of course, less than the melting temperature of the plastic forming the syringe, and it will be appreciated that a clear plastic material should be used such that the gradations and other information on the syringe may be visualized through the thin-film plastic coating. Thus, any efforts to remove the needle guard 304b or displace the plunger will be immediately detectable by the break in the thin-film 12 of plastic material, hence indicating disruption of or tampering with the seals adjacent the opposite ends of the syringe. The coating material is, of course, sufficiently thin to enable the needle guard to be readily removed from the barrel and the plunger to be readily rotated to break the seal, hence permitting axial movement of the plunger relative to the barrel. Therefore, the plastic coating can be left on the syringe barrel during use, eliminating the need to physically strip it from the barrel and dispose of it separately.

Referring now to the embodiments hereof illustrated in FIGS. 57, 58 and 59, the barrel, plunger, and adapter are formed similarly as in previous embodiments, for example, as in the preferred embodiment hereof illustrated in FIGS. 33–40 using the adapter illustrated in FIGS. 51–53. The syringe is illustrated in FIG. 57 prior to use and before a ferrule with attached needle, e.g., as illustrated in FIGS. 33 and 48, is attached to the adapter. In this form, there is provided an end cap 400 having female threads for threadedly engaging corresponding male threads on the distal end of the barrel, for example, the male threads at the barrel end illustrated in FIGS. 33 and 48. In the previous embodiments, for example, with reference to FIGS. 35–39, upon withdrawal of the adapter and needle within the barrel, the proximal end of the plunger may be broken off and reapplied to the distal end of the barrel by screw-threading the plunger and barrel to one another. There is, however, the psychologically discomforting possibility of contacting an individual's hand with the barrel end, notwithstanding the withdrawal of the needle into the barrel, prior to the threaded attachment of the proximal plunger end portion to the distal end of the barrel. Consequently, for those syringes wherein the adapter carries a Luer lock male fitting which releasably receives the ferrule of the needle, i.e., the needle is not directly or integrally attached with the adapter, the syringe may be provided as illustrated in FIG. 57 with a cap 400 screw-threaded on the distal end of the barrel. As illustrated, the cap 400 has a flat external surface 402 opposite the otherwise open end of the cap.

In FIG. 58, the cap 400a is similarly provided with internal female threads at its open end for connection with the male threads at the distal end of the barrel. The closed opposite end of the cap 400a, however, has feathered edges 404 in conjunction with a concavity or recessed face 406 in the central portion of cap 400a.

A further form of cap is illustrated in FIG. 59. In FIG. 59, cap 400b has, as indicated previously, internal female threads about its open end for threadedly engaging the male threads on the end of the barrel. At its closed end, there is provided a ring 408, the outer surface 410 of which carries an adhesive, preferably a pressure-sensitive adhesive. Ring 408 may have adhesive along its opposite side for adhesively securing it to the closed end of barrel 400b. A release membrane or paper portion 412b may be provided along the outer surface of the ring overlying and protecting the pressure-sensitive adhesive 410.

Referring now to FIGS. 60–62, the use of the caps illustrated in FIGS. 57–59 will be described in conjunction with the illustrated use of the cap 58. Instead of passing the proximal plunger end portion broken from the plunger, as illustrated in FIGS. 3–4, 25a–25c, 38, 39 or 49, in front of the barrel for connection therewith or passing the user's hands or arms adjacent the barrel end after use of the syringe, a cap 400, 400a or 400b may be placed on a table or other flat surface with its open end facing upwardly. Note that once the cap is removed from the syringe prior to use, the cap is not contaminated by any body fluids. After use, the syringe may be applied to the cap. Thus, as illustrated in FIG. 60, the proximal end of the plunger may be broken from the plunger barrel, leaving that end of the barrel seated by the plunger bung. Instead of applying the broken-off plunger end to the distal end of the barrel, it may be discarded and the distal end of the barrel may be applied to the cap. Particularly, by inserting the distal end of the barrel into the open end of the cap and exerting downward pressure on the barrel, the first few threads of the barrel may ratchet past the female threads on the cap to engage the barrel and cap one to the other. Note that the user's hand or arm need not pass in front of the possibly contaminated barrel end in order to close the barrel end with the needle retracted into the barrel.

While this axial engagement of the barrel with the cap may be sufficient to secure and seal the barrel end, the barrel is preferably rotated relative to the cap to ensure a tight, snug sealing fit between the barrel and cap. When using the flat-ended cap 400 illustrated in FIG. 7, the cap, after its initial securement to the barrel end, may be grasped and rotated relative to the barrel. Alternatively, when using the cap illustrated in FIG. 58, the downward pressure of the barrel on the feathered edges 404 of the cap causes the cap to displace air between its recessed, closed end 406 and the flat surface whereby the cap serves as a suction cup releasably adhering the cap to the surface. Consequently, once the barrel has been applied to the cap, the barrel may be rotated with the suction effect tending to maintain the cap against rotation on the flat surface. Also, the suction effect prevents the cap from sliding laterally along the flat surface. Once the barrel and cap are secured one to the other by downward pressure and relative rotation, a slight rocking motion, as illustrated in FIG. 62, will dislodge the cap from the flat surface and break its suction grip therewith.

In the embodiment illustrated in FIG. 59, the cap 400b may have release paper 410 on the annular ring 408. By removing the release paper and releasably adhesively securing the cap 400b to the flat surface, the barrel can be applied thereto and rotated relative to the cap similarly as with the embodiment of FIG. 58. The rocking motion illustrated in FIG. 62 will also release the adhesive from the surface whereby the syringe with its capped and sealed end may be removed from the adjoining surface. Also in FIG. 59, it will be appreciated that the annular ring 408 may comprise a disk or discrete areas of adhesive. Further, instead of release paper, the plastic tamperproof packaging illustrated in FIGS. 54 to 56 may be used. For example, the strip of paper or other material illustrated in FIG. 54 may be enlarged at the lower end to overlie the pressure-sensitive adhesive such that the paper wrap or shrink wrap which affords a tamperproof feature may also serve as the release paper for the adhesive. The shrink wrap of FIG. 55 may also be employed as the release paper for the embodiment hereof illustrated in FIG. 59, the shrink wrap being illustrated in FIG. 59 at 412 and the portion thereof overlying the adhesive illustrated at 412b.

Referring now to the embodiment hereof illustrated in FIGS. 63 and 64, it is advantageous to preclude the needle from exposure after use, whereby the risk of needle stick injury may be entirely avoided. That is, if the needle can be removed from the injection site and into the barrel without exposing the thus contaminated needle, the risk of needle stick injury is substantially prevented.

In this embodiment of the invention, the syringe is virtually identical apart from the distal end of the barrel. In this form, the distal end of the barrel is elongated as illustrated at 500 in FIG. 63. The elongated end portion 50 of the barrel may be externally threaded to receive the cap of the previous embodiment or the female threads at the opposite end of the plunger once the latter is broken from the syringe as previously described. Also, while the needle 502 in this embodiment is illustrated as integrally attached to the adapter 504 (which may take the form of any one of the adapters previously described), the adapter may be provided with the Luer tip for receiving the hub of a standard Luer needle. In both cases, the end of the adapter or the hub of the Luer needle is recessed within and lies short of the end of the elongated barrel end portion 500. Only the needle 502 or a portion thereof is exposed through the barrel end.

With this arrangement and as illustrated in FIGS. 63 and 64, the needle penetrates the injection site, i.e., the individual's skin Sk. The end of the barrel is also brought into engagement with the skin as the needle penetrates further into the skin, as illustrated in FIG. 63. The plunger is then depressed, injecting the fluid through the needle into the individual. Following the injection and with the barrel end of the syringe still pressed against the skin, the plunger is rotated and coupled with the adapter, as previously described, and the adapter with the needle is withdrawn with the plunger within the barrel, as illustrated in FIG. 64. In this manner, the contaminated needle is never exposed to the risk of needle stick injury. After the barrel is removed from the skin, the cap or the broken plunger portion may be secured and seated to the elongated barrel end as previously described.

Referring now to the embodiment hereof illustrated in FIGS. 65–69, there is illustrated a syringe barrel 600 carrying an adapter 602 screw-threaded at 604 into the distal end of the barrel 600. The adapter 602 includes a Luer fit 606 for mounting the hub 608 of a needle, not shown in this drawing figure. Note in the drawing figures, the annular ridges 617 projecting from the forward face of the adapter along the inside face of the annular shoulder at the distal end of the barrel. These ridges assist in performing a sealing function when the adapter is screw-threaded into the distal end of the barrel. A plunger 610 is mounted for axial movement within the barrel and includes a bung 612 at its distal end in sealing engagement along the interior side walls of the syringe barrel. The plunger is, of course, mounted for axial sliding movement within the syringe barrel for injecting fluid from within the barrel through the adapter and Luer fit into and through the needle and for drawing fluid into the barrel, for example, from a vial, not shown. The bung is formed of a Santoprene compressible material and has a plurality of circumferentially extending ribs for forming sealing engagements with the interior walls of the barrel. The plunger 610 includes at its distal end a central portion or projection 614 carrying a plurality of axially spaced ribs 616 for engaging and sealing with interior wall surfaces of bung 612.

In this form of the invention, the central portion 614 includes an axially extending male projection 615 having a plurality of discrete angularly related axially tapered sides or faces 618. In the illustrated form, the projection 618 is hexagonal in cross-sectional configuration, with the sides being tapered toward the distal end of the barrel. Spaced axially from the tapered sides is a continuously circumferentially extending radially outwardly projecting rib 620 directly adjacent a continuous circumferentially extending radially inwardly directed groove 622. The surfaces 618, 620 and 622 comprise adapter engagement structure disposed at the distal end of the plunger for engagement with complementary or mating engagement structure carried by the adapter.

The inner face of the adapter 602 is tapered toward the central axis of the adapter and has a recess 624 substantially complementary in shape to the male projection 615 on the plunger. Specifically, the recess 624 includes a plurality of tapered sides or faces 626 complementary in shape or taper to the faces 618, as well as a continuous circumferentially extending radially inwardly directed rib 628 and a continuous circumferentially extending radially outwardly projecting groove 630.

The opposite end of the plunger 610 includes a radially outwardly projecting continuously circumferentially extending rib 634. A pair of radially inwardly projecting ribs 636 and 638 are formed about the inner surface of the proximal end of the barrel defining a continuous radially outwardly extending groove 640 therebetween.

Figure 67:
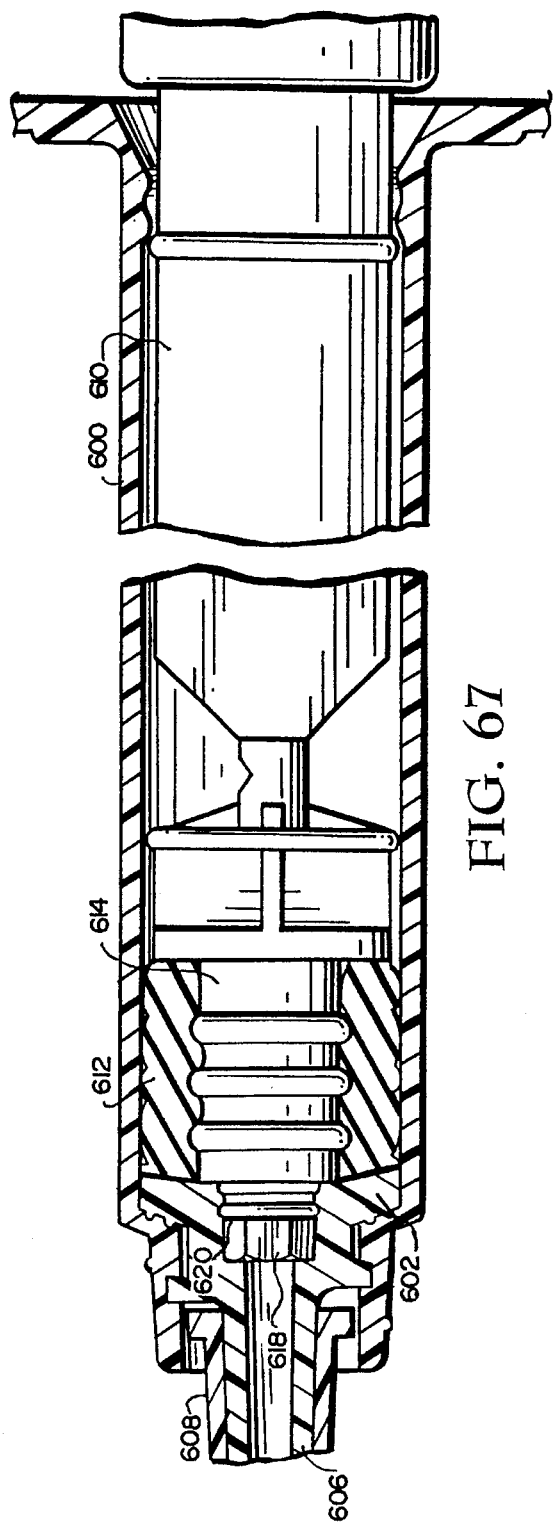

In this form of the invention, it is desirable to permanently or irreversibly lock the plunger and the adapter to one another when the plunger is finally seated in its axially innermost position within the syringe barrel such that the plunger and adapter act as a unit and cannot be axially disconnected one from the other. In this manner, the plunger and adapter can be locked permanently one to the other only with firm positive axial pressure intentionally exerted on the plunger relative to the barrel. This requires a deliberate strong axial force to be applied to the plunger to effect the locking action. It also makes it unnecessary for the user to maintain forward axial pressure on the plunger when rotating the plunger to unthread the adapter from the barrel. In use, the plunger is advanced toward the adapter such that the radially outwardly projecting rib 620 engages the inwardly projecting rib 628 on the adapter with the distal end of the plunger received in the recess of the adapter, as illustrated in FIG. 66. The user is thus able to recognize from this initial engagement and hence initial resistance to further axial movement of the plunger relative to the barrel that the plunger is just axially short of being finally seated and locked relative to the adapter. At this time, the user is thus signalled that the plunger and adapter will be permanently locked to one another upon further axial displacement of the plunger relative to the barrel. Upon such further forceful axial displacement and as illustrated in FIG. 67, the rib 620, due to the compressibility of the plastic materials principally of the plunger, slips past the rib 628 on the adapter and seats in the groove 630. Correspondingly, the radially inwardly directed rib 628 seats in the groove 622 of the adapter, thus permanently locking the plunger and adapter to one another. As the plunger is axially advanced from its position short of the finally seated position relative to the adapter, i.e., from the position illustrated in FIG. 66 to that of FIG. 67, toward the distal end of the barrel, the bung 612 compresses, as illustrated in FIG. 67. This ensures, once the plunger and adapter are retracted into a final position within the barrel, a further effective sealing action at the opposite end of the barrel. With the rib and groove engagement of the plunger and adapter, the plunger may be rotated to unscrew the adapter from the distal end of the barrel. Thus, by withdrawing the plunger from the barrel, as illustrated in FIG. 68, the adapter and needle carried thereby are withdrawn into the interior confines of the syringe barrel. By breaking the plunger off at its weakened portion, as previously described, the plunger may be threaded onto the distal end of the barrel, as illustrated in FIG. 73. With the plunger bung sealing the opposite end of the barrel and the plunger threaded on the distal end of the barrel, the barrel is sealed at its opposite ends.

Referring to the embodiment hereof illustrated in FIGS. 69–71, like reference numerals as in the prior embodiment are applied to like parts, followed by the suffix "a." In this embodiment, the bung 612a is releasably retained in a first axial position relative to the projecting portion 614a of the plunger as illustrated in FIGS. 69 and 70 and a second axial position spaced from the first axial position, illustrated in FIG. 71. To accomplish this, the projecting portion 614a of the plunger end carries a plurality of radially outwardly projecting axially spaced flared ribs 650 whereas the interior surface of the bung 612a carries a plurality of axially spaced complementary shaped circumferentially continuous tapered ribs 652. The ribs 650 and 652 are configured such that the complementary inclined surfaces thereof engage one another in the first or initial axially extended position of the bung 612a relative to the plunger, as illustrated in FIGS. 69 and 70. As the plunger is advanced to engage the ribs 620a and 628a to form the initial stop position, the annular end wall surface of bung 612*a* engages the interior axial face of the adapter 602*a*. Upon firm pressure being applied to the plunger to displace it axially into its final seated position, as previously described, this forceful axial pressure enables the plunger to slide relative to the bung such that the complementary inclined surfaces slide past one another and the radial surfaces of the projections 650 and 652 engage one another, as illustrated in FIG. 71. Thus, once the plunger and adapter are permanently locked one to the other as illustrated in FIG. 71, the plunger and adapter can be jointly rotated to unscrew the adapter from the barrel end for location of the adapter and needle carried thereby axially into the barrel, with the radial surfaces of the ribs 650 and 652 engaging one another to carry one the plunger bung axially with the plunger upon withdrawal of the plunger.

Referring now to the embodiment hereof illustrated in FIG. 72, wherein like parts as in the prior embodiments are illustrated with like reference numerals, followed by the suffix "b," there is provided a plunger having, instead of a bung, a radially outwardly directed flange 65*g* forming an interference fit with the interior wall of the barrel. The flange 658 is weakened at 660 to enable the flange to flex. Axially beyond the flange, the plunger includes the projecting portion 615*b* shaped similarly as previously described and complementary to the recess 624*b* in the adapter. Once the plunger has been advanced such that the ribs 620*b* and 628*b* initially engage one another, the flange bears against the inner face of the adapter. When final locking is desired, the plunger is advanced forwardly into its permanently seated and locking position relative to the adapter. The weakened portion 660 of the flange enables this final axial advancement of the plunger between the initial and final seated positions with the flange deforming at its weakened portion 660.

It will be appreciated that a reverse configuration of the male and female parts on the plunger and adapter, respectively, illustrated in FIGS. 65–72 may be employed, for example, with the type of plunger and adapter illustrated in FIG. 40. Thus, a radially outwardly projecting rib may be provided on the male projection of adapter 150 ahead of groove 150*c*. The initial engagement of the radially inwardly projecting rib 154 on the female end of the plunger with the radially outwardly projecting rib in advance of the groove 150*c* on adapter 150 provides the initial resistance or stop to finally locking the plunger and adapter to one another. By further forceful axial pressure on the plunger, the ribs slip past one another to finally lock the adapter and plunger to one another. Of course, the reverse of this arrangement may likewise be used, i.e., the rib and groove being located on the plunger and only a radial outwardly directed rib being located on the adapter.

It will also be appreciated that other types of permanent locking connections may be provided between the plunger and adapter. For example, complementary sawtooth ribs may be provided with their inclined surfaces engaged to provide the initial resistance and being movable past one another to engage the radial surfaces thereof to permanently lock the adapter and plunger to one another. Further, it will be appreciated that either of the male or female latching structures of the plunger and adapter, as the case may be, can have one or more axially extending slits to facilitate relative axial movement of the plunger and adapter toward their permanently locked position and without detracting from the ability of the rib and groove (or complementary sawteeth) to permanently engage one another. Also, the ancillary features of the present invention described herein such as the air venting feature of the adapter illustrated in FIGS. 51–53, the tamperproof features of FIGS. 54–56 and the cap arrangements of FIGS. 57–64 may be employed with the permanent locking feature of the embodiment of FIGS. 65–77.

Referring now to FIGS. 78 and 79, there is illustrated an arrangement of an adapter 700 and a plunger end 702 having a bung 704. The adapter 700 and plunger end 702 are similar to the adapter and plunger end illustrated in FIG. 40, except that the adapter 700 has a female recess 706 and the plunger end 702 has a male projection 708 generally complementary in shape to the female recess 706. That is, while the adapter and plunger end combination of FIG. 40 have the male and female parts on the adapter and plunger end, the adapter and plunger end illustrated in FIG. 78 have a reverse configuration and with similarly functioning elements. Thus, adapter 700 has external threads 710 for threaded engagement with the threads 712 (FIG. 79) at the barrel end of the syringe for sealing the barrel. The adapter flange 714 has a generally frustoconical shallow recess 716 opening into the recess 706. The base of recess 706 is provided with teeth 718 which have flats 720 and angled surfaces 722. Additionally, the recess 706 includes a projecting annular rib 724.

The male projection 708 on plunger end 702 is shaped for reception in the recess 706 and has complementary-shaped teeth 726. That is, teeth 726 have flats 728 and angled surfaces 730 which engage the flats 720 and angled surfaces 722 in the recess 706 of adapter 700 when the plunger is fully axially advanced in the syringe barrel. The male projection 708 also includes a radially inwardly directed annular groove 732.

The cooperation of the teeth and the rib and groove are similarly as previously described, particularly with respect to the embodiment of FIG. 40. For example, when the plunger is advanced in the barrel to engage the projection 708 in recess 706, the engagement structure enables the plunger to rotate relative to the adapter and barrel to bring the flat surfaces 728 into alignment with the flats 720 of the adapter. Once aligned, joint rotation of the plunger and adapter unthreads the adapter from the end of the syringe barrel. It will be appreciated as illustrated in FIG. 79 that when the plunger is axially advanced to its fullest extent, the rib 706 engages in the groove 732 to enable joint withdrawal of the plunger and adapter once the screw threads 710 are disengaged from the barrel threads 720. The rib-and-groove arrangement may, of course, be reversed with the groove located on the adapter and the rib on the plunger.

A particular feature of this arrangement is that the cost of materials for forming the adapter is substantially reduced. The adapter is preferably formed of a polycarbonate material and, by forming the female recess in the adapter, a significant reduction in material is achieved in comparison with the arrangement of the adapter illustrated in FIG. 4. Functionally, however, the cooperation of the male and female parts as illustrated in FIGS. 78 and 79 is the same as illustrated in FIG. 40.

While the invention has been described in connection with what is presently considered to be the most practical and preferred embodiment. It is to be understood that the invention is not to be limited to the disclosed embodiment, but on the contrary, is intended to cover various modifications and equivalent arrangements included within the spirit and scope of the appended claims.

What is claimed is:

1. A syringe comprising:

(a) a hollow, axially elongated barrel;

(b) an adapter carried by said barrel adjacent a distal end thereof and removable therefrom in response to rotation relative to said barrel, the adapter carrying a needle and providing fluid communication with the interior of said hollow barrel;

(c) a plunger axially movable in said barrel; and (d) adapter engagement structure disposed at the distal end of the plunger and engageable with a mating connection engagement structure on the adapter, said structures having respective drive and connective engagement surfaces, said drive surfaces being engageable with one another in response to axial movement of said plunger toward the distal end of said barrel and jointly movable upon engagement to enable rotation of the adapter relative to the barrel in response to relative rotation of the plunger and barrel to cause the adapter to part from the distal end of the barrel, said connective surfaces being engageable with one another to connect the plunger and adapter one with the other and enable said adapter, when parted from the end of the barrel in response to joint rotation of said adapter and said plunger relative to said barrel, to be withdrawn with the needle into the interior of the barrel in response to joint axial movement of said plunger and said adapter in a direction away from the distal end of the barrel.

2. A syringe according to claim 1 wherein said adapter engagement structure at the distal end of the plunger and said mating connection engagement structure on the adapter include respective surfaces cooperable to cause relative rotation of said plunger and said adapter in response to axial movement of the plunger toward the distal end of the barrel.

3. A syringe according to claim 2 wherein said respective surfaces are cooperable to cause relative rotation of said plunger and said adapter in response to axial movement of the plunger toward the distal end of the barrel prior to engagement of said drive surfaces with one another.

4. A syringe according to claim 2 wherein at least one of said respective surfaces is inclined relative to the axis of the barrel.

5. A syringe according to claim 1 wherein said adapter engagement structure at the distal end of the plunger and said mating connection engagement structure on the adapter include respective alignment surfaces different than said drive surfaces and cooperable to cause relative rotation of said plunger and said adapter in response to axial movement of the plunger toward the distal end of the barrel.

6. A syringe according to claim 1 wherein said plunger has a first portion projecting from a proximal end of the barrel and a second portion within the barrel when the adapter and needle are withdrawn into the barrel, said first portion being removable from said second portion.

7. A syringe according to claim 6 wherein the barrel includes a catch for preventing removal of said second portion from the proximal end of the barrel when the adapter and needle are withdrawn into the barrel.

8. A syringe according to claim 6 wherein said plunger is formed of a plastic material and includes a reduced portion of plastic material between said first and second plunger portions enabling the first portion to be broken from the second portion.

9. A syringe according to claim 6 wherein a proximal end of said first portion of said plunger and the distal end of said barrel have surfaces engageable with one another upon removal of the first plunger portion from the second plunger portion and engagement of those surfaces with one another to close the distal end of the barrel after withdrawal of the adapter and needle from the distal end of the barrel.

10. A syringe according to claim 9 wherein the surfaces on the proximal end of the first portion of the plunger and the distal end of the barrel comprise threaded surfaces.

11. A syringe according to claim 9 wherein the surfaces on the proximal end of the first portion of the plunger and the distal end of the barrel comprise female and male threads, respectively.

12. A syringe according to claim 11 wherein the proximal end of the first portion of the plunger has a recess in part defined by said female threads, the distal end of said barrel having a portion including the male threads for reception in the recess whereby the surfaces may be threadedly engaged.

13. A syringe according to claim 9 wherein said first portion of said plunger comprises a cylindrical sleeve open at said proximal end and closed at the distal end of said first portion, the interior of said sleeve forming a continuation of the interior of said barrel at the distal end thereof.

14. A syringe according to claim 1 wherein said plunger is movable in said barrel between retracted and extended positions relative to said barrel and including means connecting said barrel and said plunger in the retracted position of said plunger to indicate attempted movement of said plunger and said barrel relative to one another.

15. A syringe according to claim 1 including a pair of surfaces carried by said syringe cooperable to cause relative rotation of said plunger and said adapter in response to axial movement of the plunger toward the distal end of the barrel and thereby enable engagement of said drive surfaces.

16. A syringe according to claim 15 wherein said pair of surfaces cooperate with one another to cause said plunger to rotate relative to said adapter in the same rotational direction as the direction of rotation of the adapter relative to the barrel which enables the adapter to part from the end of the barrel.

17. A syringe according to claim 15 wherein said pair of surfaces are engageable with one another and enable said plunger to rotate relative to said adapter in an opposite rotational direction as the direction of rotation of the adapter relative to the barrel which enables the adapter to part from the end of the barrel.

18. A syringe according to claim 1 wherein said connective surfaces comprise a pair of radially directed latching elements engageable with one another with one element lying axially behind another of said elements enabling joint axial movement of the plunger and adapter in a direction away from the distal end of the barrel.

19. A syringe according to claim 18 including a pair of surfaces carried by said syringe cooperable to cause rotation of said plunger relative to said adapter in response to axial movement of the plunger toward the distal end of the barrel, said plunger rotation being in the same rotational direction as the direction of rotation of the adapter relative to the barrel which enables the adapter to part from the end of the barrel.

20. A syringe according to claim 1 wherein said plunger is movable between advanced and retracted positions relative to said barrel, a seal between said plunger and said barrel adjacent the proximal end of the barrel when the plunger lies in its advanced position, and a seal at the distal end of the barrel whereby the interior of the barrel is maintained sterile.

21. A syringe according to claim 1 wherein the adapter includes a fluid passage providing for fluid communication with the interior of said hollow barrel, said adapter having a proximal end within said barrel and a distal end, said adapter further including a fluid passage portion in communication with said fluid passage and opening into the interior of the barrel at a location between the proximal end of said adapter and the distal end of said barrel to enable air to be vented through said fluid passage upon receiving fluid into said barrel and moving said plunger toward the distal end of said barrel.

22. A syringe comprising:

(a) a hollow, axially elongated barrel;

(b) an adapter carried by said barrel adjacent a distal end thereof and removable therefrom in response to rotation relative to said barrel, the adapter having a hub for carrying a needle and providing fluid communication with the interior of said hollow barrel;

(c) a plunger axially movable in said barrel; and (d) adapter engagement structure disposed at the distal end of the plunger and engageable with a mating connection engagement structure on the adapter, said structures having respective drive and connective engagement surfaces, said drive surfaces being engageable with one another in response to axial movement of said plunger toward the distal end of said barrel and jointly movable upon engagement to enable rotation of the adapter relative to the barrel in response to relative rotation of the plunger and barrel to cause the adapter to part from the distal end of the barrel, said connective surfaces being engageable with one another to connect the plunger and adapter one with the other and enable said adapter, when parted from the end of the barrel in response to joint rotation of said adapter and said plunger relative to said barrel, to be withdrawn with any needle carried thereby into the interior of the barrel in response to joint axial movement of said plunger and said adapter in a direction away from the distal end of the barrel.

23. A syringe comprising:

(a) a hollow, axially elongated barrel having distal and proximal ends, said barrel at said distal end having interior female threads;

(b) an adapter carried by said barrel adjacent a distal end thereof and having male threads for threaded engagement with said female threads, said adapter being unthreadable and removable from the distal end of said barrel in response to rotation of said adapter relative to said barrel, said adapter having a central fluid opening and carrying a needle for providing fluid communication with the interior of said hollow barrel;

(c) a plunger axially movable in said barrel and projecting from said proximal end thereof terminating in a finger press external of said barrel; and (d) adapter engagement structure disposed at a distal end of the plunger and engageable with a mating plunger engagement structure on the adapter, said structures having respective drive and connective engagement surfaces, said drive surfaces being engageable with one another and jointly movable when engaged to enable rotation of the adapter relative to the barrel in response to relative rotation of the plunger and barrel to cause the adapter to unthread from the distal end of the barrel, said connective surfaces comprising a respective rib and groove engageable with one another in response to axial movement of said plunger toward said adapter to connect the plunger and adapter one with the other and enable said adapter, when unthreaded from the distal end of the barrel in response to joint rotation of said adapter and said plunger relative to said barrel, to be withdrawn with the needle into the interior of the barrel upon joint axial movement of said plunger and said adapter in a direction away from the distal end of the barrel.

24. A syringe according to claim 23 wherein said adapter engagement structure at the distal end of the plunger and said mating plunger engagement structure on the adapter include respective surfaces cooperable to cause relative rotation of said plunger and said adapter in response to axial movement of the plunger toward the distal end of the barrel.

25. A syringe according to claim 24 wherein at least one of the latter respective surfaces is inclined relative to the axis of the barrel.

26. A syringe according to claim 23 wherein said adapter engagement structure at the distal end of the plunger and said mating plunger engagement structure on the adapter include respective alignment surfaces different than said drive surfaces and cooperable to cause relative rotation of said plunger and said adapter in response to axial movement of the plunger toward the distal end of the barrel.

27. A syringe according to claim 23 wherein said plunger has a first portion projecting from the proximal end of the barrel and a second portion within the barrel when the adapter and needle are withdrawn into the barrel, said first portion being removable from said second portion.

28. A syringe according to claim 27 wherein the barrel includes a catch for preventing removal of said second portion of said plunger from the proximal end of the barrel when the adapter and needle are withdrawn into the barrel.

29. A syringe according to claim 27 wherein a proximal end of said first portion of said plunger and the distal end of said barrel have surfaces engageable with one another upon removal of the first plunger portion from the second plunger portion and engagement of those surfaces with one another to close the distal end of the barrel after withdrawal of the adapter and needle from the distal end of the barrel.

30. A syringe according to claim 29 wherein the surfaces on the proximal end of the first portion of the plunger and the distal end of the barrel comprise female and male threads, respectively, the proximal end of the first portion of the plunger having a recess in part defined by said female threads, the distal end of said barrel having a portion including said male threads for reception in the recess whereby the surfaces may be threadedly engaged.

31. A syringe according to claim 23 including a pair of alignment surfaces carried by adapter and said plunger and cooperable with one another to cause relative rotation of said plunger and said adapter in response to axial movement of the plunger toward the distal end of the barrel and thereby enable engagement of said drive surfaces, said pair of alignment surfaces being cooperable with one another to cause said plunger to rotate relative to said adapter in the same rotational direction as the direction of rotation of the adapter relative to the barrel when the adapter is unthreaded relative to the distal end of the barrel, said pair of alignment surfaces being engageable with one another and enabling said plunger to rotate relative to said adapter in an opposite rotational direction when said alignment surfaces are engaged.

32. A syringe comprising:

(a) a hollow, axially elongated barrel;

(b) an adapter carried by said barrel adjacent a distal end thereof and removable therefrom in response to rotation relative to said barrel, the adapter carrying a needle and providing fluid communication with the interior of said hollow barrel;

(c) a plunger axially movable in said barrel;

(d) adapter engagement structure disposed at the distal end of the plunger and engageable with a mating connection engagement structure on the adapter, said structures having respective drive and connective engagement surfaces, said drive surfaces being engageable with one another and jointly movable when engaged to enable rotation of the adapter relative to the barrel in response to relative rotation of the plunger and barrel to cause the adapter to part from the distal end of the barrel, said connective surfaces being engageable with one another to connect the plunger and adapter one with the other and enable said adapter, when parted from the end of the barrel in response to joint rotation of said adapter and said plunger relative to said barrel, to be withdrawn with the needle into the interior of the barrel in response to joint axial movement of said plunger and said adapter in a direction away from the distal end of the barrel; and (e) said plunger having a first portion projecting from the proximal end of the barrel and a second portion within the barrel when the adapter and needle are withdrawn into the barrel, said first portion being removable from said second portion, said barrel including a catch for preventing removal of said second portion of said plunger from the proximal end of the barrel when the adapter and needle are withdrawn into the barrel; a proximal end of said first portion of said plunger and the distal end of said barrel having surfaces engageable with one another upon removal of the first plunger portion from the second plunger portion and engagement of those surfaces with one another to close the distal end of the barrel after withdrawal of the adapter and needle from the distal end of the barrel.

33. A syringe according to claim 32 wherein the surfaces on the proximal end of the first portion of the plunger and the distal end of the barrel comprise female and male threads, respectively, the proximal end of the first portion of the plunger having a recess in part defined by said female threads, the distal end of said barrel having a portion including said male threads for reception in the recess whereby the surfaces may be threadedly engaged.

* * * * *